(12) United States Patent
Peters et al.

(10) Patent No.: US 9,458,113 B2
(45) Date of Patent: Oct. 4, 2016

(54) SUBSTITUTED BICYCLIC DIHYDROPYRIMIDINONES AND THEIR USE AS INHIBITORS OF NEUTROPHIL ELASTASE ACTIVITY

(71) Applicant: Boehringer Ingelheim International GmbH, Ingelheim am Rhein (DE)

(72) Inventors: Stefan Peters, Biberach an der Riss (DE); Ralf Anderskewitz, Laupheim (DE); Christian Gnamm, Biberach an der Riss (DE); Holger Hoesch, Biberach an der Riss (DE); Gerd Morschhaeuser, Biberach an der Riss (DE); Thorsten Oost, Biberach an der Riss (DE); Uwe Joerg Ries, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/809,314

(22) Filed: Jul. 27, 2015

(65) Prior Publication Data

US 2016/0031830 A1    Feb. 4, 2016

(30) Foreign Application Priority Data

Jul. 31, 2014  (EP) ..................... 14179259

(51) Int. Cl.
| | | |
|---|---|---|
| *C07D 239/70* | (2006.01) | |
| *C07D 401/10* | (2006.01) | |
| *C07D 403/10* | (2006.01) | |
| *C07D 405/12* | (2006.01) | |
| *C07D 413/10* | (2006.01) | |
| *C07D 417/10* | (2006.01) | |
| *A61K 31/517* | (2006.01) | |
| *A61K 31/5355* | (2006.01) | |

(52) U.S. Cl.
CPC ........... *C07D 239/70* (2013.01); *C07D 401/10* (2013.01); *C07D 403/10* (2013.01); *C07D 405/12* (2013.01); *C07D 413/10* (2013.01)

(58) Field of Classification Search
None
See application file for complete search history.

(56) References Cited

U.S. PATENT DOCUMENTS

| | | |
|---|---|---|
| 8,580,800 B2 | 11/2013 | Von Nussbaum et al. |
| 8,889,700 B2 | 11/2014 | Von Nussbaum et al. |
| 9,040,516 B2 | 5/2015 | Shiro et al. |
| 2009/0093477 A1 | 4/2009 | Ray et al. |
| 2010/0010024 A1 | 1/2010 | Von Nussbaum et al. |
| 2011/0034433 A1 | 2/2011 | Von Nussbaum et al. |
| 2012/0004203 A1 | 1/2012 | Von Nussbaum et al. |
| 2012/0094968 A1 | 4/2012 | Von Nussbaum et al. |
| 2013/0065913 A1 | 3/2013 | Blench et al. |
| 2014/0221335 A1 | 8/2014 | Gnamm et al. |
| 2014/0249129 A1 | 9/2014 | Gnamm et al. |

FOREIGN PATENT DOCUMENTS

| | | |
|---|---|---|
| CA | 2656307 A1 | 1/2008 |
| DE | 102006031314 A1 | 1/2008 |
| DE | 102007061766 A1 | 6/2009 |
| DE | 102009004197 A1 | 7/2010 |

(Continued)

OTHER PUBLICATIONS

Abstract in English for DE102007061766, Jun. 25, 2009.

(Continued)

*Primary Examiner* — Emily Bernhardt
(74) *Attorney, Agent, or Firm* — Michael P. Morris; Edward S. Lazer

(57) ABSTRACT

Substituted dihydropyrimidinones of formula 1

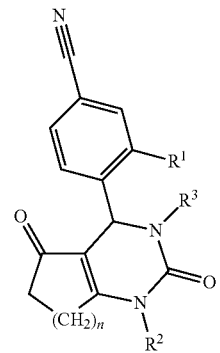

which are neutrophil elastase inhibitors and useful as medicaments for the treatment of, inter alia, COPD. Exemplary is

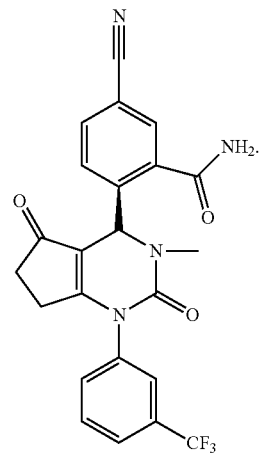

13 Claims, No Drawings

(56) References Cited

FOREIGN PATENT DOCUMENTS

| | | |
|---|---|---|
| GB | 2392910 A | 3/2004 |
| WO | 03053930 | 7/2003 |
| WO | 2004020410 A2 | 3/2004 |
| WO | 2004020412 A1 | 3/2004 |
| WO | 2004024700 A1 | 3/2004 |
| WO | 2004024701 A1 | 3/2004 |
| WO | 2005082863 A2 | 9/2005 |
| WO | 2005082864 A1 | 9/2005 |
| WO | 2006082412 A2 | 8/2006 |
| WO | 2006136857 A1 | 12/2006 |
| WO | 2007129060 A1 | 11/2007 |
| WO | 2008135537 A1 | 11/2008 |
| WO | 2009013444 A1 | 1/2009 |
| WO | 2009037413 A1 | 3/2009 |
| WO | 2009060158 A1 | 5/2009 |
| WO | 2009060203 A1 | 5/2009 |
| WO | 2009060206 A1 | 5/2009 |
| WO | 2009080199 A1 | 7/2009 |
| WO | 2009135599 A1 | 11/2009 |
| WO | 2010078953 A1 | 7/2010 |
| WO | 2010115548 A1 | 10/2010 |
| WO | 2011110858 A1 | 9/2011 |
| WO | 2011110859 A1 | 9/2011 |
| WO | 2012002502 A1 | 1/2012 |
| WO | 2013018804 A1 | 2/2013 |
| WO | 2014029830 A1 | 2/2014 |
| WO | 2014029831 A1 | 2/2014 |
| WO | 2014029832 A1 | 2/2014 |
| WO | 2014122160 A1 | 8/2014 |
| WO | 2014135414 A1 | 9/2014 |

OTHER PUBLICATIONS

Abstract in English for WO2012002502, May 1, 2012.
SJO et al., "Neutrophil elastase inhibitors: recent advances in the development of mechanism-based and nonelectrophilic inhibitors", Future Medicinal Chemistry, vol. 4, 2012, p. 651-660.
International Search Report and Written Opinion for corresponding application, PCT/EP2015/067497, date of mailing Oct. 5, 2015.

SUBSTITUTED BICYCLIC DIHYDROPYRIMIDINONES AND THEIR USE AS INHIBITORS OF NEUTROPHIL ELASTASE ACTIVITY

This invention relates to substituted bicyclic dihydropyrimidinones of formula 1

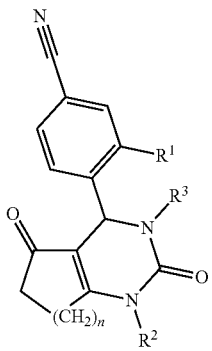

and their use as inhibitors of neutrophil elastase activity, pharmaceutical compositions containing the same, and methods of using the same as agents for treatment and/or prevention of pulmonary, gastrointestinal and genitourinary diseases, inflammatory diseases of the skin and the eye and other autoimmune and allergic disorders, allograft rejection, and oncological diseases.

BACKGROUND INFORMATION

The following references describe neutrophil elastase inhibitors with a monocyclic dihydro-pyrimidinone core: GB2392910, WO04024700, WO05082864, WO05082863, DE102006031314, U.S. Ser. No. 10/001,0024, WO10115548, WO09080199, DE102007061766, WO06136857, WO06082412, WO12002502.

The following references describe neutrophil elastase inhibitors with a bicyclic tetra-hydropyrrolopyrimidinedione core: WO07129060, WO08135537, U.S. Ser. No. 09/009,3477, WO09013444, WO09060206, WO09060203, WO09060158, U.S. Ser. No. 11/003,4433.

The following references describe neutrophil elastase inhibitors with core structures other than those herein before mentioned: WO04020412, WO04020410, WO03053930, WO10078953, WO09135599, DE102009004197, WO11110858, WO11110859, WO09060158, WO09037413, WO04024701, U.S. Ser. No. 13/006,5913, WO13018804, WO12002502, WO2014029831, WO2014029832 and WO2014029830.

For a review on various inhibitors of neutrophil elastase see: P. Sjö (*Future Med. Chem.* 2012, 4, 651-660).

BRIEF SUMMARY OF THE INVENTION

Neutrophil elastase (NE) is a 29 kDa serine protease. It is expressed in bone marrow precursor cells, stored in the granula of peripheral blood granulocytes at high concentrations and it is released upon cellular activation. To the substrates of NE belong major elements of the extracellular matrix: elastin, fibronectin, laminin, collagen and proteoglycans. Neutrophil elastase activity leads to ECM degradation, increases migration and chemotaxis of monocytes and vascular smooth muscle cells and directly affects components of the coagulation and fibrinolytic pathways (PAI-1 and TFPI). Increased activity of neutrophil elastase is associated with chronic inflammatory and fibrotic diseases of several organs. The potential of neutrophil elastase inhibitors as anti-inflammatory therapies has been reviewed by P. A. Henriksen in *Current Opinion in Hematology* 2014, 21, 23-28. Inhibitors of neutrophil elastase will therefore have an important role for the treatment of different diseases like COPD, idiopathic pulmonary fibrosis and other fibrotic diseases, cancer, acute lung injury, acute respiratory distress syndrome, bronchiectasis, cystic fibrosis, alpha1-antitrypsin deficiency and others.

The problem of the present invention is to prepare new compounds which on the basis of their pharmaceutical effectiveness as inhibitors of neutrophil elastase activity, may be used therapeutically, that is for the treatment of pathophysiological processes caused by increased activity of neutrophil elastase.

It has surprisingly been found that the compounds of the present invention have the following properties which are advantageous in view of the indications of the current invention.

The compounds according to the present invention, including the physiologically acceptable salts, are effective as inhibitors of neutrophil elastase and exhibit favourable inhibitory potency, as determined by the half maximal inhibitory concentration ($IC_{50}$), in an enzymatic inhibition assay.

Some compounds according to the present invention, including the physiologically acceptable salts, are additionally effective as inhibitors of neutrophil serin protease proteinase 3 and exhibit favourable inhibitory potency, as determined by the half maximal inhibitory concentration ($IC_{50}$), in an enzymatic inhibition assay. This inhibitory activity on a second neutrophil serin protease may be beneficial for pharmacological efficacy.

Some compounds according to the present invention, including the physiologically acceptable salts, exhibit favourable inhibitory potency, as determined by the half maximal effective concentration ($EC_{50}$), in a plasma or whole-blood assay, for instance as described in T. Stevens et al. (*J. Pharm. Exp. Ther.* 2011, 339, 313-320).

Some compounds according to the present invention, including the physiologically acceptable salts, exhibit favourable in vivo potency, as determined, for example, by the half maximal effective dose ($ED_{50}$), in models of human neutrophil elastase-induced lung injury in mouse or rat, for instance as described in Tremblay et al. (*Chest* 2002, 121, 582-588) or T. Stevens et al. (*J. Pharm. Exp. Ther.* 2011, 339, 313-320).

Some compounds according to the present invention, including the physiologically acceptable salts, exhibit favourable metabolic stability in an in vitro microsomal assay for metabolic stability as described in E. Kerns & L. Di (*Drug-like properties: concepts, structure design and methods: from ADME to toxicity optimization*, Elsevier, 1$^{st}$ ed, 2008), chapter 29 and references therein.

Some compounds according to the present invention, including the physiologically acceptable salts, exhibit favourable metabolic stability in an in vitro hepatocytes assay for metabolic stability as described in E. Kerns & L. Di (*Drug-like properties: concepts, structure design and methods: from ADME to toxicity optimization*, Elsevier, 1$^{st}$ ed, 2008), chapter 29 and references therein.

An improved metabolic stability in an in vitro test system is expected to translate into a reduced in vivo clearance (CL), because the metabolic conversion in the liver is reduced. Based on the pharmacokinetic equation $CL/F_{oral}=Dose/AUC$ ($F_{oral}$: oral bioavailability, AUC: area under the curve), a reduced in vivo clearance is expected to lead to higher dose-normalized systemic exposure (AUC) of the drug.

Some compounds according to the present invention, including the physiologically acceptable salts, exhibit favourable permeability in an in vitro Caco-2 cell layer method for permeability as described in E. Kerns & L. Di (*Drug-like properties: concepts, structure design and methods: from ADME to toxicity optimization*, Elsevier, 1st ed, 2008), chapter 26 and references therein. For an oral drug, improved permeability is expected to translate into a higher fraction of the drug absorbed in the intestinal tract, thus, resulting in higher dose-normalized systemic exposure (AUC).

Some compounds according to the present invention, including the physiologically acceptable salts, exhibit a favourable, that is low efflux ratio (permeability in the efflux direction divided by the permeability in the influx direction) in an in vitro Caco-2 or MDCK cell layer method as described in E. Kerns & L. Di (*Drug-like properties: concepts, structure design and methods: from ADME to toxicity optimization*, Elsevier, 1st ed, 2008), chapter 26 and 27 and references therein. For an oral drug, an improved, that is reduced efflux ratio is expected to translate into a higher fraction of the drug absorbed in the intestinal tract, thus, resulting in higher dose-normalized systemic exposure (AUC).

Some compounds according to the present invention, including the physiologically acceptable salts, exhibit favourable aqueous solubility in a kinetic or thermodynamic solubility method as described in E. Kerns & L. Di (*Drug-like properties: concepts, 15 structure design and methods: from ADME to toxicity optimization*, Elsevier, 1st ed, 2008), chapter 25 and references therein. For an oral drug, improved aqueous solubility is expected to translate into a higher fraction of the drug absorbed in the intestinal tract resulting in higher dose-normalized systemic exposure (AUC) and/or oral bioavailability ($F_{oral}$) and/or peak plasma concentration after administration ($C_{max}$). Furthermore, improved aqueous solubility is expected to reduce development challenges, such as expensive formulations, increased development time, high drug load.

Comparatively higher dose-normalized systemic exposure (AUC) can be advantageous in several ways: (1) If a certain systemic exposure (AUC) needs to be achieved for efficacy, the drug can be dosed in a lower amount. Lower dosages have the advantages of lower drug load (parent drug and metabolites thereof) for the patient causing potentially less side effects, and lower production costs for the drug product. (2) Comparatively higher dose-normalized systemic exposure (AUC) can lead to increased efficacy or prolonged duration of action of the drug when the same dose is applied.

Some compounds according to the present invention, including the physiologically acceptable salts, exhibit favourable metabolic stability, favourable permeability and favourable aqueous solubility. Accordingly, some compounds of the present invention are expected to exhibit favourable pharmacokinetic (PK) properties after oral dosing, in particular favourable systemic exposure (area under the curve, AUC), thus, leading to favourable efficacy in vivo. Some compounds according to the present invention, including the physiologically acceptable salts, exhibit favourable pharmacokinetic (PK) properties. The PK properties can be determined in pre-clinical animal species, for example mouse, rat, hamster, dog, guinea pig, mini pig, cynomolgus monkey, rhesus monkey. The PK properties of a compound can be described, for example, by the following parameters: Mean residence time (MRT), elimination half-live ($t_{1/2}$), volume-of-distribution ($V_D$), area under the curve (AUC), clearance (CL) and bioavailability after oral administration ($F_{oral}$), peak plasma concentration after administration ($C_{max}$), time to reach Cmax ($T_{max}$).

Some compounds according to the present invention and metabolites thereof are devoid of the hydrazine sub-structure that causes structural alerts for mutagenicity and carcinogenicity as described in Benigni et al. (*Chem. Rev.* 2011, 11, 2507-2536). Thus, compounds of the invention may bear the advantage of reduced genotoxic potential.

Some compounds according to the present invention, including the physiologically acceptable salts, exhibit favourable inhibition of cytochrome P450 (CYP) isozymes in corresponding in vitro assays for CYP isozyme inhibition as described in E. Kerns & L. Di (*Drug-like properties: concepts, structure design and methods: from ADME to toxicity optimization*, Elsevier, 1st ed, 2008), chapter 32 and references therein. Reduced inhibition of CYP isozymes is expected to translate into a reduced risk for undesirable drug-drug interactions which is the interference of one drug with the normal metabolic or pharmacokinetic behaviour of a co-administered drug.

Some compounds according to the present invention, including the physiologically acceptable salts, exhibit favourable, that is low, CYP induction potential. Cytochrome P450 (CYP) induction can affect the pharmacokinetics of a drug molecule upon multiple dosing, which can result in pharmacokinetic drug-drug interactions with co-administered drugs. CYP induction can lead to decreased exposure of the inducing compound (e.g. autoinduction) or decreased exposure of a co-administered compound metabolized by the induced enzyme. CYP induction can also lead to an increase in the metabolism of a drug causing changes in pharmacological (active metabolite) and toxicological (toxic metabolite) outcomes.

Some compounds according to the present invention, including the physiologically acceptable salts, exhibit favourable, that is low, inhibition of the hERG channel in a patch clamp assay as described in E. Kerns & L. Di (*Drug-like properties: concepts, structure design and methods: from ADME to toxicity optimization*, Elsevier, 1st ed, 2008), chapter 34 and references cited therein.

DETAILED DESCRIPTION OF THE INVENTION

A compound of formula 1

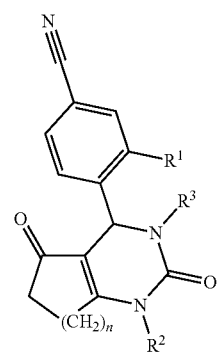

wherein

R$^1$ is selected from the group consisting of
—CO—R$^{1.1}$, R$^{1.11}$ and —CH$_2$—R$^{1.12}$, R$^{1.1}$ is selected from the group consisting of
—NH$_2$, —NH—C$_{1-4}$-alkyl, —NH—R$^{1.6}$, —NH—CH$_2$—R$^{1.6}$, —NH—CH(CH$_3$)—R$^{1.9}$, —NH—CH$_2$—CH$_2$—R$^{1.4}$, —NH—CH$_2$—CH$_2$—CH$_2$—R$^{1.7}$, —N(CH$_3$)—CH$_2$—CH$_2$—CH$_2$—R$^{1.8}$, —N(C$_{1-3}$-alkyl)$_2$, —N(C$_{3-6}$-cycloalkyl)(C$_{1-3}$-alkyl), —N(CH$_3$)—CH$_2$—CH$_2$—R$^{1.5}$, —N(CH$_3$)—CH$_2$—R$^{1.10}$, —NH—R$^{1.2}$, R$^{1.3}$, —OH, —OCH$_3$ and —NH—CH$_2$—C≡CH, R$^{1.2}$ is selected from the group consisting of
C$_{3-6}$-cycloalkyl and 4- to 6 membered heterocyclic ring, each ring optionally substituted by one or two C$_{1-3}$ alkyl, —NH2, —OH or =O, R$^{1.3}$ denotes a 4- to 10-membered heterocyclic or heteroaryl ring, containing one, two, three or four elements independently selected from among N and O, each of the rings optionally substituted with one or two substituents independently selected from among morpholinyl, —NHCOCH$_3$, —N(CH$_3$)COCH$_3$, —COCH$_3$, —OH, —NH$_2$, —N(CH$_3$)$_2$ and C$_{1-3}$ alkyl, R$^{1.4}$, R$^{1.5}$ are independently selected from the group consisting of morpholinyl, —NH$_2$, —OH, F, —N(CH$_3$)$_2$, —O—CH$_3$ and —SO$_2$—CH$_3$, R$^{1.6}$, R$^{1.9}$, R$^{1.10}$ are independently selected from the group consisting of —CO-morpholinyl, —CN, —CF$_3$, —CHF$_2$, —C(CH$_3$)$_2$OH, —C(CH$_3$)$_2$NH$_2$ and —C(CH$_3$)$_2$CN or are independently selected from the group consisting of phenyl and a 4- to 10-membered heterocyclic or heteroaryl ring, containing one to four elements independently selected from among N and O, each of the rings optionally substituted with C$_{1-3}$ alkyl or CN, R$^{1.7}$ is —OH, —O—CH$_3$, R$^{1.8}$ is —O—CH$_3$, R$^{1.11}$ denotes a 5- to 10-membered heterocyclic or 5- to 10-membered heteroaryl ring, containing one to four heteroatoms independently selected from among N, O and S, each of the rings optionally substituted with a group independently selected from among C$_{1-3}$ alkyl, C$_{1-3}$-cycloalkyl, OH, =O, —COO—C$_{1-4}$-alkyl, —O—C$_{1-3}$-alkyl, —O—C$_{1-3}$-cycloalkyl, —CN, halogen, —CO—C$_{1-3}$-alkyl, —CO—C$_{1-3}$-cycloalkyl and —N(CH$_3$)$_2$.

R$^{1.12}$ is selected from the group consisting of, —NH—R$^{1.13}$, —N(CH$_3$)—R$^{1.13}$, and
a 5- to 6-membered N-containing heterocyclic ring, bound via N-atom to the core structure, optionally containing additional to the N-atom one to 3 heteroatoms independently selected from among N, O and S, each of the rings optionally substituted with a group independently selected from among C$_{1-3}$ alkyl, C$_{1-3}$-cycloalkyl, OH, =O, —COO—C$_{1-4}$-alkyl, —O—C$_{1-3}$ alkyl, —O—C$_{1-3}$-cycloalkyl, —CN, halogen, —CO—C$_{1-3}$-alkyl, —CO—C$_{1-3}$-cycloalkyl, —N(CH$_3$)$_2$.

R$^{1.13}$ denotes a group selected from among C$_{3-6}$-cycloalkyl, C$_{1-4}$-alkyl, each optionally substituted by a group selected from among halogen and OH, and
a 6-membered heterocyclic ring, containing one to four heteroatoms independently selected from among N, O and S, optionally substituted by a group selected from among halogen, —OCH$_3$ and OH n is 1 or 2

R$^2$ is phenyl or pyridinyl, each substituted with CF$_3$, —CHF$_2$, C$_{1-4}$ alkyl and halogen R$^3$ is selected from the group consisting of R$^{3.1}$, R$^{3.1}$—CO—, R$^{3.1}$—O—CO—, R$^{3.1}$SO$_2$—, R$^{3.1}$R$^{3.2}$N—CO—, R$^{3.1}$R$^{3.2}$N—CO—CH$_2$—;

R$^{3.1}$ is selected from the group consisting of H, —C$_{1-4}$ alkyl, —C$_{3-6}$ cycloalkyl, —C$_{1-4}$-haloalkyl and —C$_{3-6}$-halocycloalkyl,
each optionally substituted with one substituent independently selected from the group consisting of OH, CN, NH$_2$, (C$_{1-4}$-alkyl)NH—, (C$_{1-4}$-alkyl)(C$_{1-4}$-alkyl)N—, azetidinyl, pyrrolidinyl, piperidinyl, piperazinyl, N—C$_{1-4}$-alkyl-piperazinyl, C$_{1-4}$-alkoxy, oxetanyl, tetrahydrofuranyl and tetrahydropyranyl, R$^{3.2}$ is selected from the group consisting of H and C$_{1-4}$-alkyl;

or, in case R$^3$ is selected from the group consisting of R$^{3.1}$R$^{3.2}$N—CO— and R$^{3.1}$R$^{3.2}$N—CO—CH$_2$—, R$^{3.2}$ and R$^{3.1}$ may form, together with the nitrogen atom to which they are bound, a ring independently selected from the group consisting of azetidine, pyrrolidine, piperidine, piperazine and N—C$_{1-4}$-alkyl-piperazine;

or optical and geometrical isomers, solvates, hydrates or salts, preferably pharmaceutically acceptable salts, thereof.

USED TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, C$_{1-6}$-alkyl means an alkyl group or radical having 1 to 6 carbon atoms.

In general in single groups like HO, H$_2$N, S(O), S(O)$_2$, NC (cyano), HOOC, F$_3$C or the like, the skilled artisan can see the radical attachment point(s) to the molecule from the free valences of the group itself. For combined groups comprising two or more subgroups, the first or last named subgroup, where the free valence is indicated, for example, the substituent "aryl-C$_{1-3}$-alkyl-" means an aryl group which is bound to a C$_{1-3}$-alkyl-group, the latter of which is bound to the core or to the group to which the substituent is attached.

In case a compound of the present invention is depicted in form of a chemical name and as a formula in case of any discrepancy the formula shall prevail. An asterisk or a broken line may be used in sub-formulas to indicate the bond which is connected to the core molecule as defined.

For example, the term "3-carboxypropyl-group" represents the following substituent:

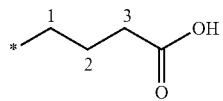

wherein the carboxy group is attached to the third carbon atom of the propyl group. The terms "1-methylpropyl-", "2,2-dimethylpropyl-" or "cyclopropylmethyl-" group represent the following groups:

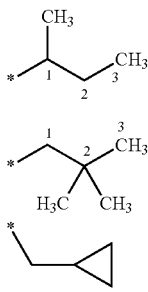

The asterisk may be used in sub-formulas to indicate the bond which is connected to the core molecule as defined.

Many of the followings terms may be used repeatedly in the definition of a formula or group and in each case have one of the meanings given above, independently of one another.

The term "substituted" as used herein, means that any one or more hydrogens on the designated atom is replaced with a selection from the indicated group, provided that the designated atom's normal valence is not exceeded, and that the substitution results in a stable compound.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

All isomeric forms (especially all stereoisomeric forms, e.g. all chiral, enantiomeric, diastereomeric and racemic forms, all tautomeric and all geometric isomeric forms) of a compound of the present invention are intended with this invention, unless the specific isomer is specifically indicated. Obviously, the isomer which is pharmacologically more potent and/or more efficacious is preferred.

It will be appreciated that the compounds of the present invention contain at least one asymmetrically substituted carbon atom, and may therefore be isolated as pure enantiomers or as a racemic or non-racemic mixture of both enantiomers. It will be appreciated that some of the compounds of the present invention contain more than one stereogenic center, that is more than one asymmetrically substituted carbon or sulfur atom, and may therefore be isolated as pure diastereomers or as diastereomeric mixtures, both in optically active or racemic forms.

The invention contemplates all conceivable stereoisomers, particularly the diastereomers and enantiomers mentioned herein, e.g. in substantially pure form, in enriched form (e.g. substantially free of any or all other undesired enantiomers and/or diastereomers and/or in any mixing ratio, including the racemic forms, as well as the salts thereof.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by enantioselective crystallization from a conglomerate of enantiomorphous crystals under suitable conditions; or by (fractional) crystallization from a suitable solvent in the presence of an optically active chiral auxiliary.

The term halogen generally denotes fluorine, chlorine, bromine and iodine.

As used herein the term "prodrug" refers to (i) an inactive form of a drug that exerts its effects after metabolic processes within the body converting it to a usable or active form, or (ii) a substance that gives rise to a pharmacologically active metabolite, although not itself active (that is an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound, for example, by hydrolysis in blood or by activation via oxidation as in case of thioether groups. Most common prodrugs include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris-(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamidobenzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

The term "$C_{1-n}$-alkylene" wherein n is an integer 2 to n, either alone or in combination with another radical, denotes an acyclic, straight or branched chain divalent alkyl radical containing from 1 to n carbon atoms. For example the term $C_{1-4}$-alkylene includes —CH$_2$—, —CH$_2$—CH$_2$—, —CH (CH₃)—, —CH₂—CH₂—CH₂—, —C(CH₃)₂—, —CH(CH₂CH₃)—, —CH(CH₃)—CH₂—, —CH₂—CH(CH₃)—, —CH₂—CH₂—CH₂—CH₂—, —CH₂—CH₂—CH(CH₃)—, —CH(CH₃)—CH₂—CH₂—, —CH₂—CH(CH₃)—CH₂—, —CH₂—C(CH₃)₂—, —C(CH₃)₂—CH₂—, —CH(CH₃)—CH(CH₃)—, —CH₂—CH(CH₂CH₃)—, —CH(CH₂CH₃)—CH₂—, —CH(CH₂CH₂CH₃)—, —CH(CH(CH₃))₂— and —C(CH₃)(CH₂CH₃)—.

The term "C₃₋ₙ-cycloalkyl", wherein n is an integer from 4 to n, either alone or in combination with another radical denotes a cyclic, saturated, unbranched hydrocarbon radical with 3 to n C atoms. For example the term C₃₋₇-cycloalkyl includes cyclopropyl, cyclobutyl, cyclopentyl, cyclohexyl and cycloheptyl.

By the term "halo" added to a "alkyl", "alkylene" or "cycloalkyl" group (saturated or unsaturated) is such a alkyl or cycloalkyl group wherein one or more hydrogen atoms are replaced by a halogen atom selected from among fluorine, chlorine or bromine, preferably fluorine and chlorine, particularly preferred is fluorine. Examples include: HFC—, HFC—, F₃C—.

The term "aryl" as used herein, either alone or in combination with another radical, denotes a carbocyclic aromatic monocyclic group containing 6 carbon atoms which may be further fused to a second five- or six-membered, carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" means a saturated or unsaturated mono- or polycyclic-ring system including aromatic ring system containing one or more elements selected from N, O, S, S(O) or S(O)₂, consisting of 3 to 14 ring atoms wherein none of the heteroatoms is part of the aromatic ring. The term "heterocyclyl" is intended to include all the possible isomeric forms; thus, the term "heterocyclyl" includes the following exemplary structures which are not depicted as radicals as each form may be attached through a covalent bond to any atom so long as appropriate valences are maintained:

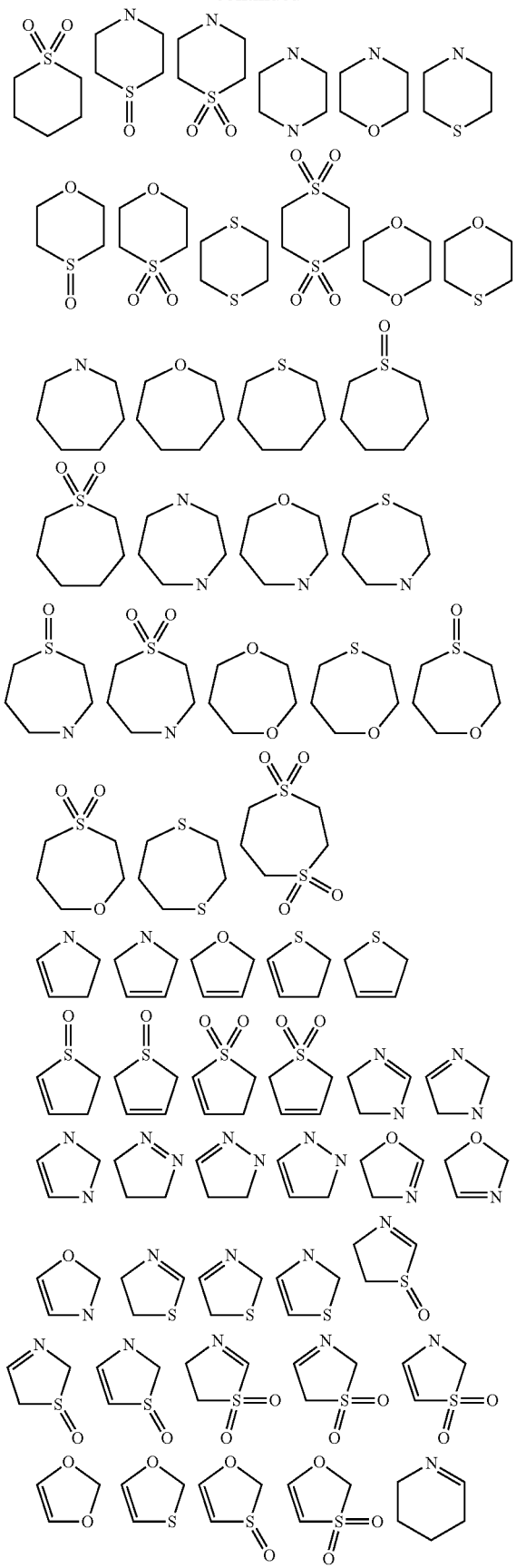

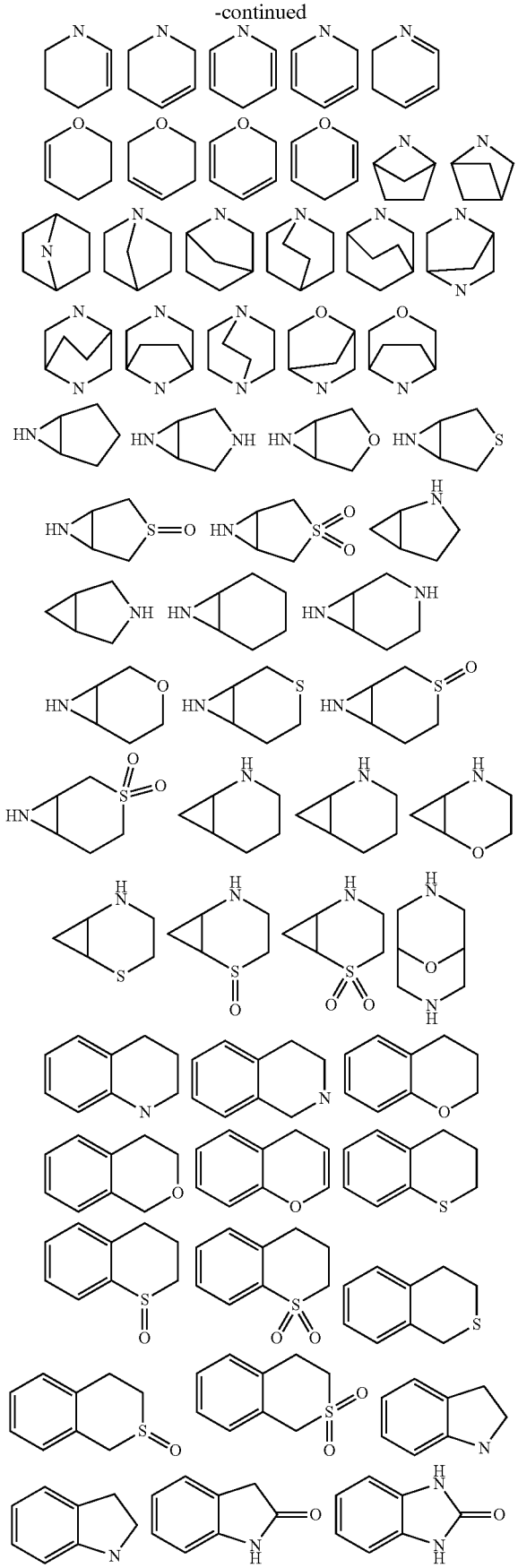
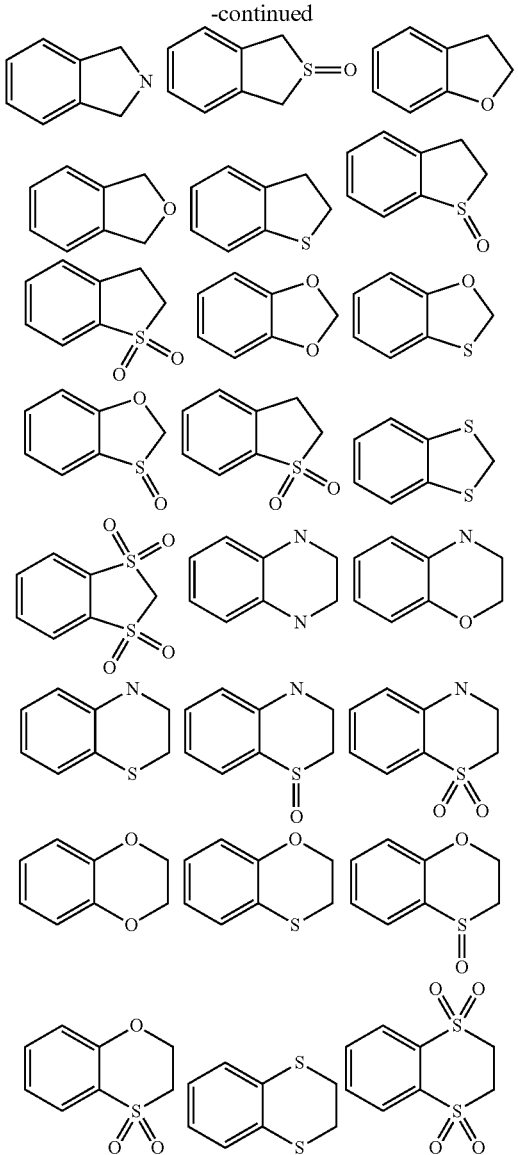

The term "heteroaryl" means a mono- or polycyclic-ring systems containing one or more elements selected from N, O, S, S(O) or S(O)$_2$, consisting of 5 to 14 ring atoms wherein at least one of the heteroatoms is part of aromatic ring. The term "heteroaryl" is intended to include all the possible isomeric forms; Thus, the term "heteroaryl" includes the following exemplary structures which are not depicted as radicals as each form may be attached through a covalent bond to any atom so long as appropriate valences are maintained:

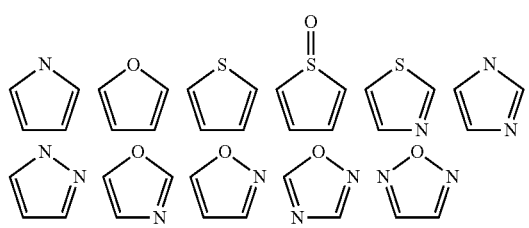

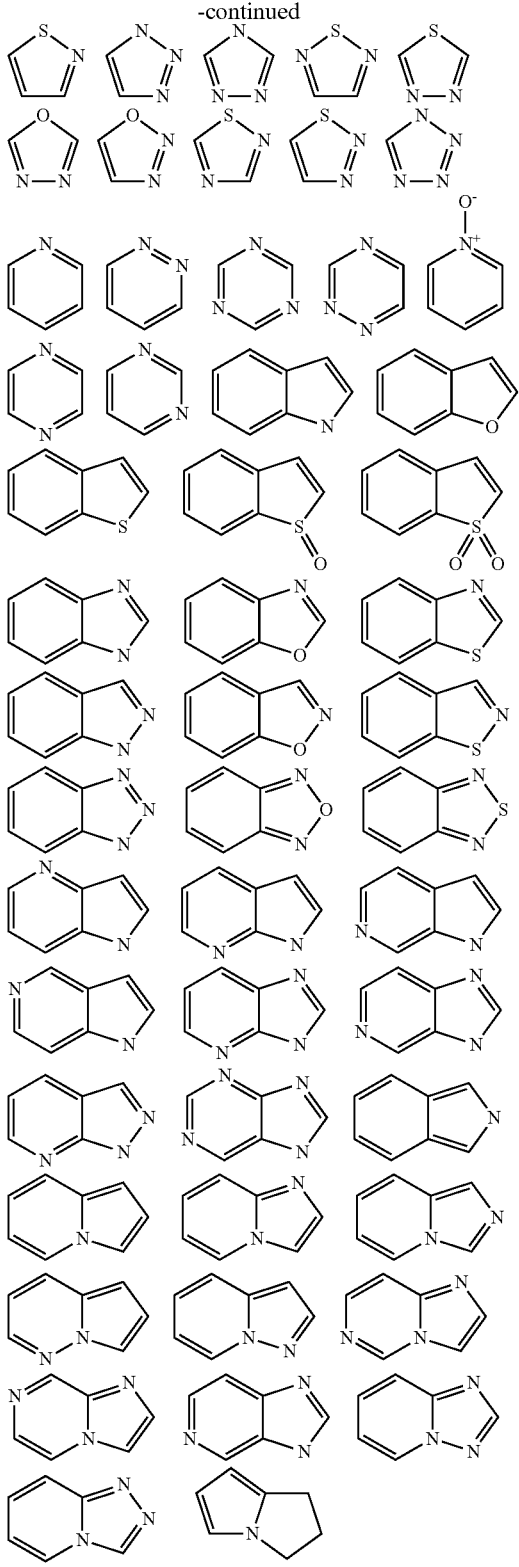

$R^{1.1}$ is selected from the group consisting of
—$NH_2$, —NH—$C_{1-4}$-alkyl, —NH—$CH_2$—$R^{1.6}$, —NH—CH($CH_3$)—$R^{1.9}$, —NH—$CH_2$—$CH_2$—$R^{1.4}$, —NH—$CH_2$—$CH_2$—$CH_2$—$R^{1.7}$, —NH—$CH_2$—$CH_2$—$CH_2$—$CH_2$—$R^{1.8}$, —N($C_{1-3}$-alkyl)$_2$, —N($CH_3$)—$CH_2$—$CH_2$—$R^{1.5}$, —N($CH_3$)—$CH_2$—$R^{1.10}$, —NH—$R^{1.2}$, $R^{1.3}$, —OH, —$OCH_3$ and —NH—$CH_2$—C≡CH, $R^{1.2}$ is selected from the group consisting of
$C_{3-6}$-cycloalkyl and 4- to 6 membered heterocyclic ring, each ring optionally substituted by $C_{1-3}$ alkyl, —OH or =O, $R^{1.3}$ denotes a 4- to 6-membered heterocyclic or heteroaryl ring, containing one, two or three elements independently selected from among N and O, each of the rings optionally substituted with one or two substituents independently selected from among morpholinyl, —$NHCOCH_3$, —N($CH_3$)$COCH_3$, —$COCH_3$, —OH, —$NH_2$, —N($CH_3$)$_2$ and $C_{1-3}$ alkyl, $R^{1.4}$ is selected from the group consisting of
morpholinyl, —$NH_2$, —OH, F, —NH—$CH_3$, —N($CH_3$)$_2$, —O—$CH_3$ and —$SO_2$—$CH_3$, $R^{1.5}$ is selected from the group consisting of
morpholinyl, —$NH_2$, —OH and —NH—$CH_3$, $R^{1.6}$, $R^{1.9}$, $R^{1.10}$ are independently selected from the group consisting of —CO-morpholinyl, —CN, —$CF_3$, $CHF_2$, —C($CH_3$)$_2$OH and —C($CH_3$)$_2NH_2$ or are independently selected from the group consisting of phenyl and a 4- to 6-membered heterocyclic or heteroaryl ring, containing one, to four elements independently selected from among N and O, each of the rings optionally substituted with $C_{1-3}$ alkyl or CN, $R^{1.7}$ is —OH, —O—$CH_3$ $R^{1.8}$ is —O—$CH_3$, $R^{1.11}$ denotes a 5- to 6-membered heterocyclic or 5- to 6-membered heteroaryl ring, containing one to four heteroatoms independently selected from among N, O and S, each of the rings optionally substituted with a group independently selected from among $C_{1-3}$ alkyl, =O and —COO—$C_{1-4}$-alkyl, $R^{1.12}$ is selected from the group consisting of —NH—$C_{1-4}$-alkyl, —NH—$R^{1.13}$ and
a 6-membered N-containing heterocyclic ring, bound via N-atom to the core structure, optionally containing additional to the N-atom one to 3 heteroatoms independently selected from among N, O and S, $R^{1.13}$ denotes a 6-membered heterocyclic ring, containing one to four heteroatoms independently selected from among N, O and S, n is 1 or 2

$R^2$ is phenyl or pyridinyl, each substituted with $CF_3$ or $CHF_2$, $R^3$ is H or methyl, or a pharmaceutically acceptable salt thereof.

Embodied are the above compounds of formula 1, wherein $R^1$ is selected from the group consisting of
—CO—$R^{1.1}$, $R^{1.11}$ and —$CH_2$—$R^{1.12}$, $R^{1.1}$ is selected from the group consisting of
—$NH_2$, —NH—$C_{1-4}$-alkyl, —NH—$R^{1.6}$, —NH—$CH_2$—$R^{1.6}$, —NH—CH($CH_3$)—$R^{1.9}$, —NH—$CH_2$—$CH_2$—$R^{1.4}$, —NH—$CH_2$—$CH_2$—$CH_2$—$R^{1.7}$, —NH—$CH_2$—$CH_2$—$CH_2$—$R^{1.8}$, —N($CH_3$)—$CH_2$—$CH_2$—$CH_2$—$R^{1.8}$, —N($CH_3$)$_2$—N($CH_3$)—$CH_2$—$CH_2$—$R^{1.5}$, —N($CH_3$)—$CH_2$—$R^{1.10}$, —NH—$R^{1.2}$, $R^{1.3}$, —OH, —$OCH_3$ and —NH—$CH_2$—C≡CH,

EMBODIMENTS

Embodied are the above compounds of formula 1, wherein
$R^1$ is selected from the group consisting of —CO—$R^{1.1}$, $R^{1.11}$ and —$CH_2$—$R^{1.12}$ $R^{1.2}$ is selected from the group consisting of Formulas a.1 to a.14
$R^{1.3}$ is selected from the group consisting of formulas b.1 to b.37
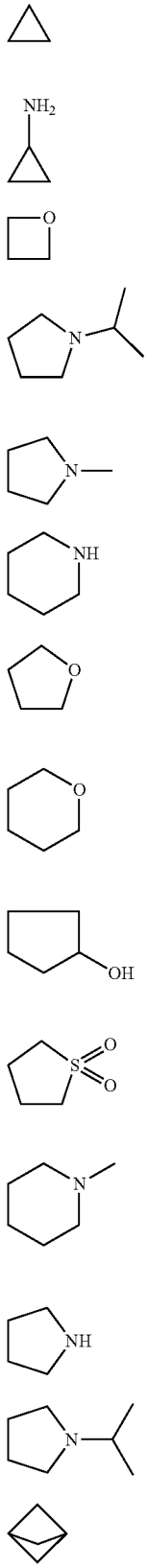
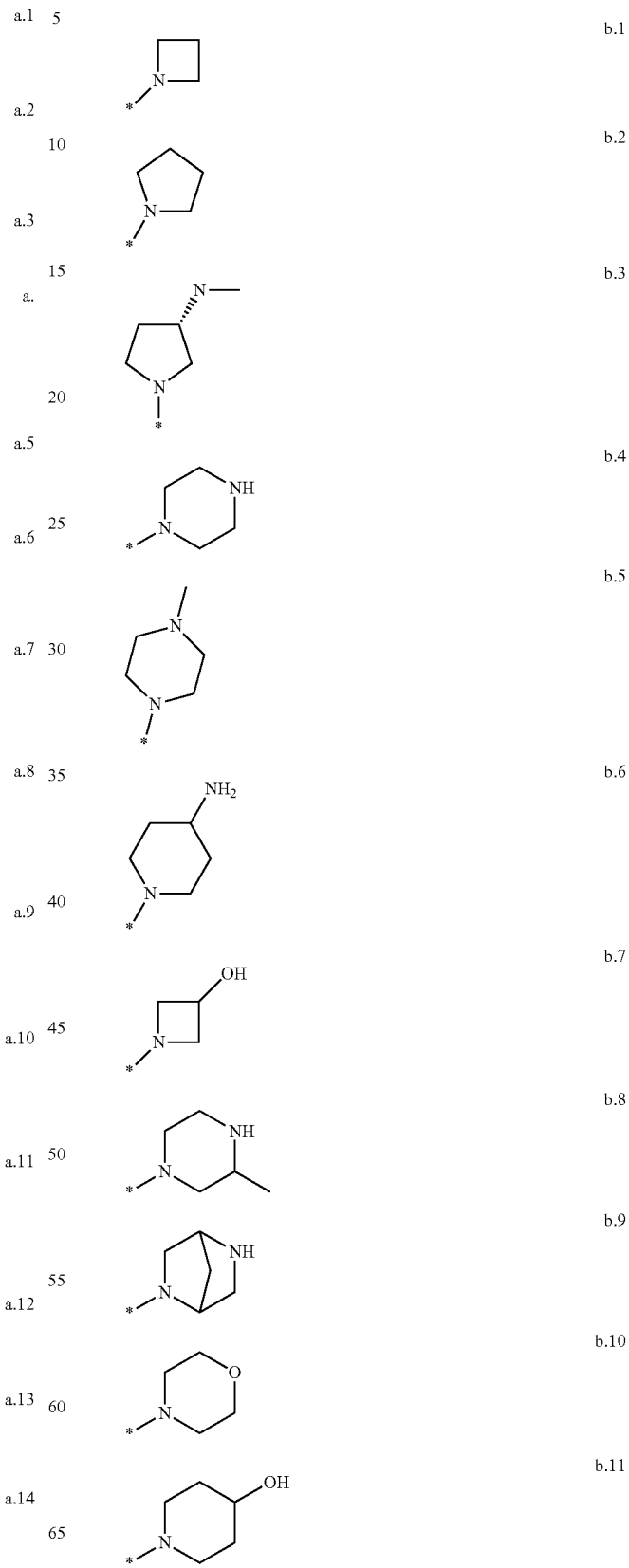

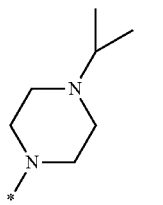 b.12
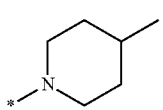 b.13
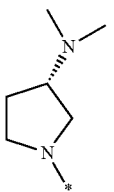 b.14
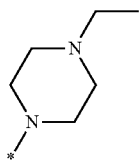 b.15
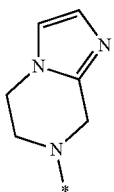 b.16
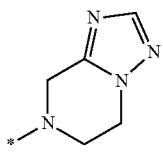 b.17
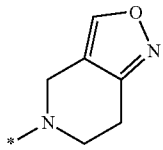 b.18
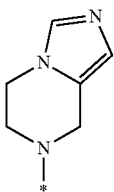 b.19
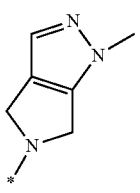 b.20
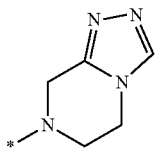 b.21
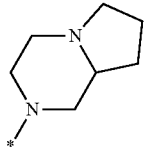 b.22
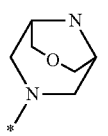 b.23
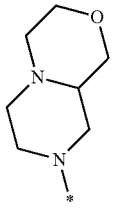 b.24
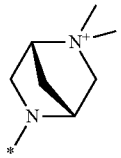 b.25
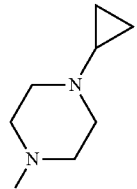 b.26
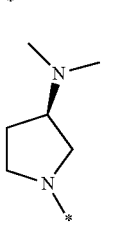 b.27
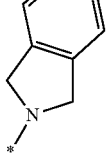 b.28
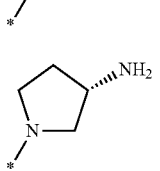 b.29

-continued

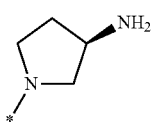
b.30

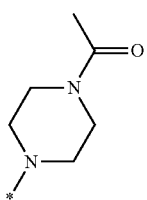
b.31

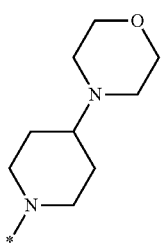
b.32

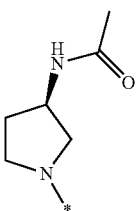
b.33

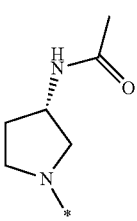
b.34

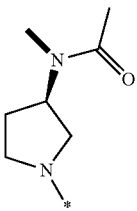
b.35

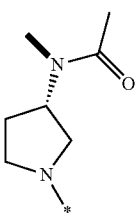
b.36

-continued

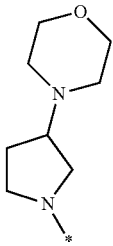
b.37

$R^{1.4}$ is selected from the group consisting of morpholinyl, —NH$_2$, —OH, F, —NH—CH$_3$, —N(CH$_3$)$_2$, —O—CH$_3$ and —SO$_2$—CH$_3$, $R^{15}$ is selected from the group consisting of morpholinyl, NH$_2$, —OH, —NH—CH$_3$ and —N(CH$_3$)$_2$, $R^{1.6}$ is selected from the group consisting of —CO-morpholinyl,
—CN, —CF$_3$, CHF$_2$, —C(CH$_3$)$_2$OH, —C(CH$_3$)$_2$CN and —C(CH$_3$)$_2$NH$_2$ or is selected from the group consisting of formulas c.1 to c.12

c.1

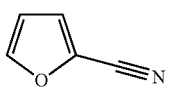
c.2

c.3

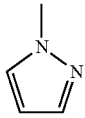
c.4

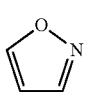
c.5

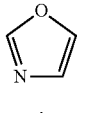
c.6

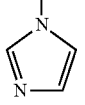
c.7

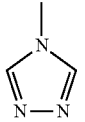
c.8

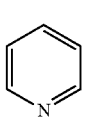
c.9

-continued c.10

c.11
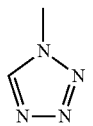

c.12

$R^{1.7}$ is —OH, —O—CH$_3$,
$R^{1.8}$ is —O—CH$_3$,
$R^{1.9}$ is formula c.1,
$R^{1.10}$ is selected from the group consisting of formulas c.3, c4, c.5, c.7, c8, and c.9,
$R^{1.11}$ denotes a 5- to 10-membered heterocyclic or 5- to 10-membered heteroaryl ring, containing one to four heteroatoms independently selected from among N, O and S, each of the rings optionally substituted with a group independently selected from among $C_{1-3}$ alkyl, =O, —COO—$C_{1-4}$-alkyl and —O—$C_{1-3}$alkyl,
n is 1 or 2,
$R^2$ is phenyl or pyridinyl, each substituted with CF$_3$,
$R^3$ is H or methyl
or a pharmaceutically acceptable salt thereof.

Embodied are the above compounds of formula 1, wherein
$R^{1.1}$ is selected from the group consisting of —NH$_2$, —NH—CH$_3$, —N(CH$_3$)$_2$ and $R^{1.3}$,
$R^{1.3}$ is a residue of formula b.10,
n is 1
$R^2$ is phenyl substituted with CF$_3$,
or a pharmaceutically acceptable salt thereof.

Embodied are the above compounds of formula 1, wherein
$R^2$ is a residue of formula d.1 or d.2 d.1
d.2
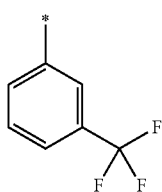

or a pharmaceutically acceptable salt thereof.
Embodied are the above compounds of formula 1, wherein
$R^1$ is —CO—$R^{1.1}$
or a pharmaceutically acceptable salt thereof.

Embodied are the above compounds of formula 1, selected from the group consisting of compounds 1.a to 1.q, 1.a
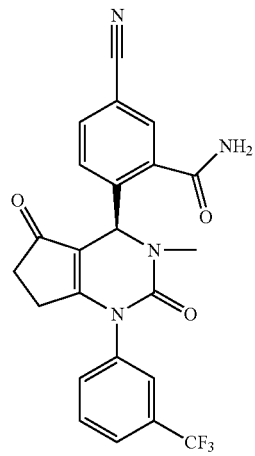

1.b
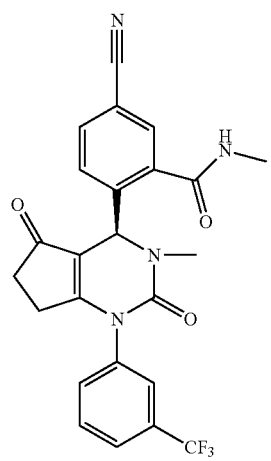

1.c
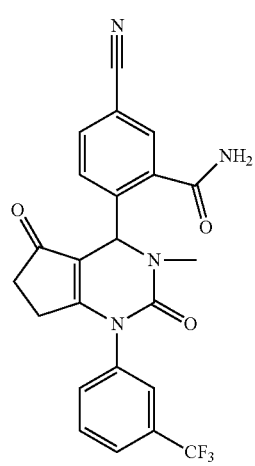

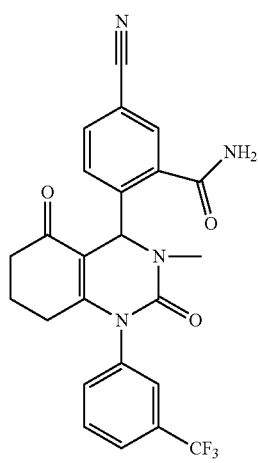
1.d
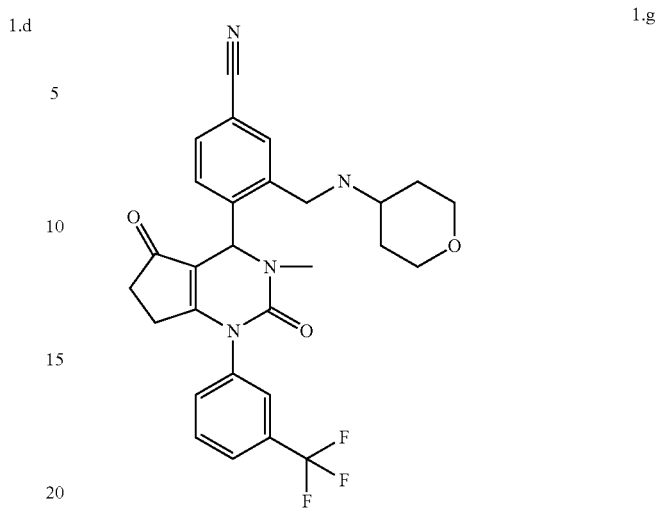
1.e
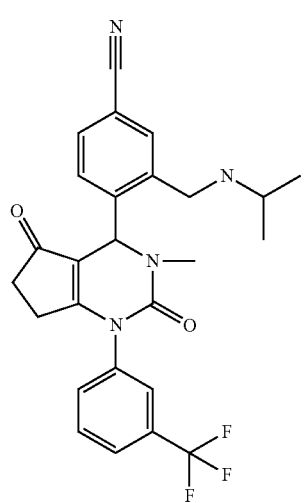
1.f
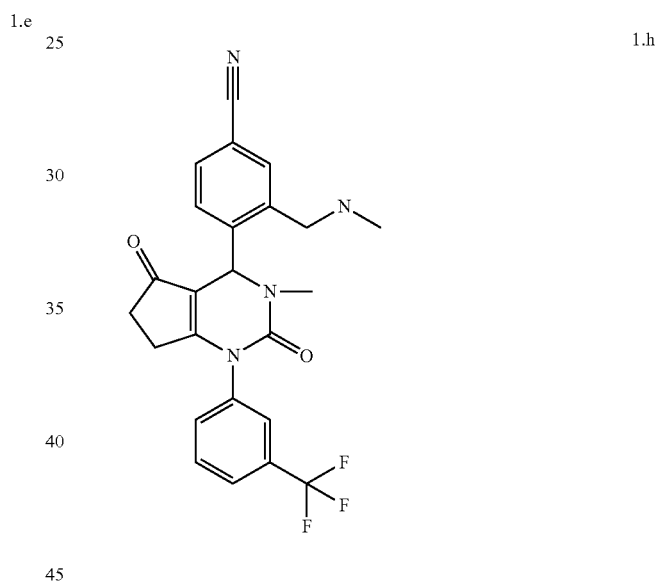
1.g
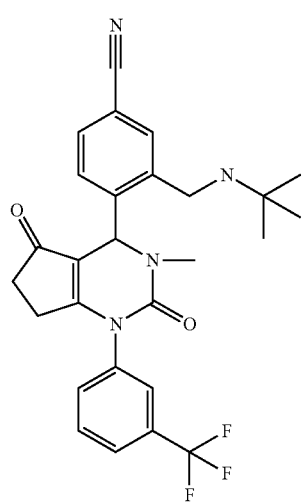
1.h
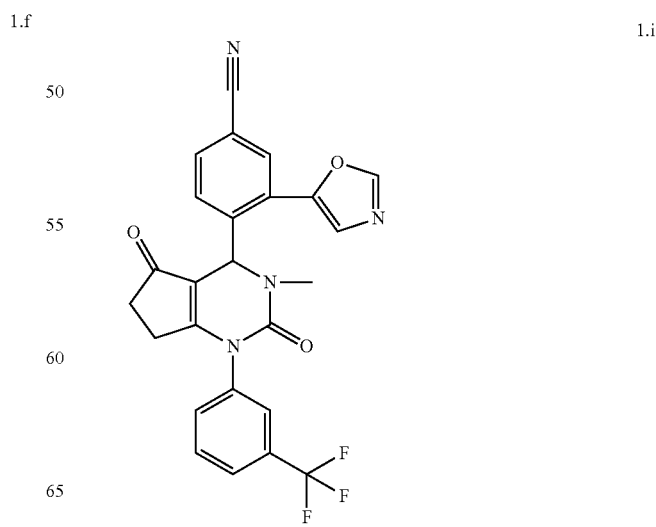
1.i

| | |
|---|---|
| 1.j 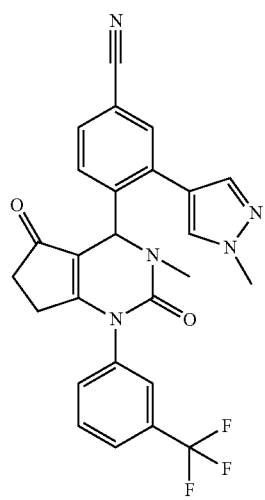 | 1.m 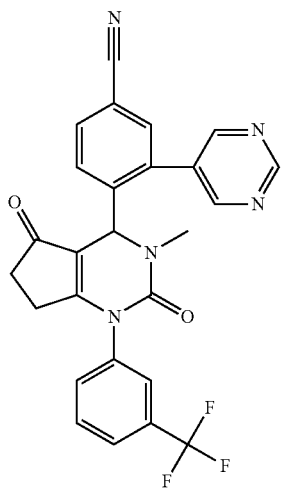 |
| 1.k 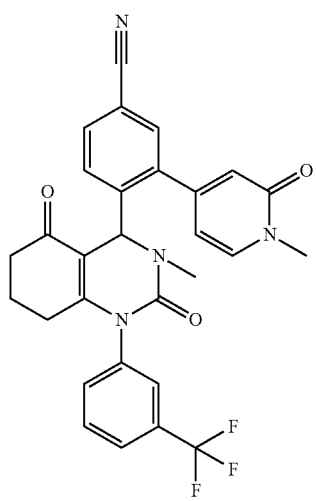 | 1.n 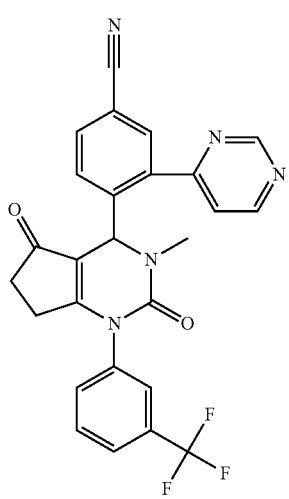 |
| 1.l 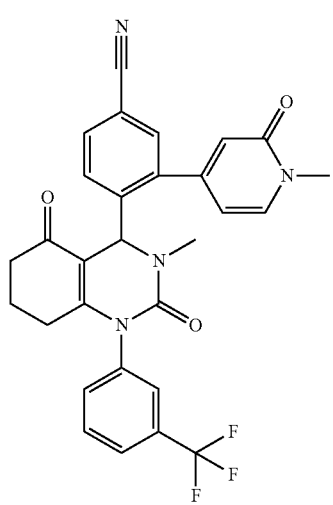 | 1.o 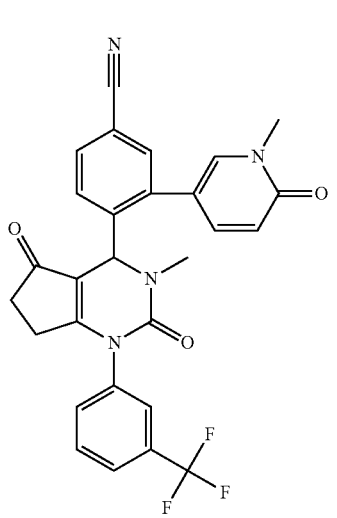 |

-continued 1.p

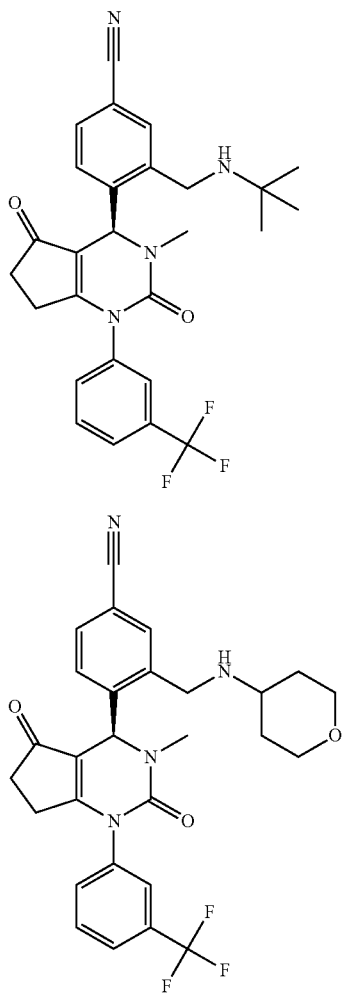

1.q or a pharmaceutically acceptable salt thereof.

Embodied are the above compounds of formula 1, wherein
R$^1$ is R$^{1.11}$
or a pharmaceutically acceptable salt thereof.

Embodied are the above compounds of formula 1, wherein
R$^{1.11}$ is selected from the group consisting of f.1 to f.17, optionally substituted with one or two groups independently selected from among —CH$_3$, =O, —O—C$_{1-3}$-alkyl, and —COO—C$_{1-4}$-alkyl

f.1

f.2

f.3

f.4

f.5

f.6

f.7

f.8

f.9

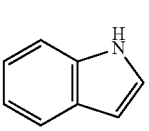
f.10

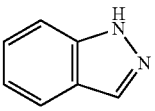
f.11

f.12

f.13 f.14 f.15 f.16 f.17 or a pharmaceutically acceptable salt thereof.

Embodied are the above compounds of formula 1, wherein
R$^1$—CH$_2$—R$^{1.12}$
or a pharmaceutically acceptable salt thereof.

Embodied are the above compounds of formula 1A,

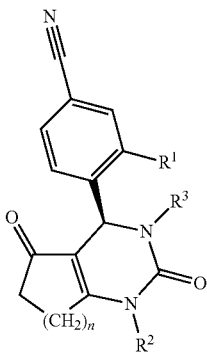

or a pharmaceutically acceptable salt thereof.

Another embodiment of the current invention are the above compounds of formula 1 for use as a medicament.

Another embodiment of the current invention are the above compounds of formula 1 for use as a medicament for the treatment of asthma and allergic diseases, gastrointestinal inflammatory diseases, glomerulonephritis, eosinophilic diseases, chronic obstructive pulmonary disease, infection by pathogenic microbes and rheumatoid arthritis.

Another embodiment of the current invention are the above compounds formula 1 for use as a medicament for the treatment of neutrophilic diseases, cystic fibrosis (CF), non-cystic fibrosis, idiopathic pulmonary fibrosis, bronchiectasis, ANCA-associated vasculitis, lung cancer, bronchiectasis, emphysema, chronic bronchitis, acute lung injury (ALI), acute respiratory distress syndrome (ARDS), pulmonary hypertension, pulmonary arterial hypertension (PAH) and Alpha-1-antitrypsin deficiency (AATD).

Another embodiment of the current invention are the above compounds formula 1 for use as a medicament for the treatment of obesity and related inflammation, insulin resistance, diabetes, fatty liver and liver steatosis.

A further embodiment of the present invention is a compound of formula 1, for use as a medicament for the treatment of traumatic brain injury, abdominal aortic aneurism and Graft vs. Host Disease (GvHD).

Another embodiment of the current invention is a method of treatment or prevention of diseases in which neutrophil elastase inhibitors have a therapeutic benefit, which method comprises administration of a therapeutically or preventively effective amount of a compounds of formula 1 to a patient in need thereof.

Another embodiment of the current invention is a pharmaceutical composition containing one or more compounds of formula 1 or a pharmaceutically active salt thereof.

A pharmaceutical composition comprising additionally to a compound of formula 1, a pharmaceutically active compound selected from the group consisting of betamimetics, anticholinergics, corticosteroids, PDE4-inhibitors, LTD4-antagonists, EGFR-inhibitors, Cathepsin C inhibitors, CRTH2 inhibitors, 5-LO-inhibitors, Histamine receptor antagonists and SYK-inhibitors, but also combinations of two or three active substances.

Embodied is a compound of formula 1, wherein $R^1$ is $R^{1.a}$ and $R^{1.a}$ is phenyl,
  substituted with CN and —CO—$R^{1.1}$.

Embodied is a compound of formula 1, wherein $R^1$ is phenyl,
  substituted with CN and $R^{1.11}$, Embodied is a compound of formula 1, wherein $R^1$ is phenyl,
  substituted with CN and —CH$_2$—$R^{1.12}$.

Embodied is a compound of formula 1, wherein $R^{1.1}$ is selected from the group consisting of
—NH$_2$, —NH—C$_{1-4}$-alkyl, —NH—$R^{1.6}$, —NH—CH$_2$—$R^{1.6}$, —NH—CH(CH$_3$)—$R^{1.9}$, —NH—CH$_2$—CH$_2$—$R^{1.4}$, —NH—CH$_2$—CH$_2$—CH$_2$—$R^{1.7}$, —NH—CH$_2$—CH$_2$—CH$_2$—$R^{1.8}$, —N(CH$_3$)—CH$_2$—CH$_2$—CH$_2$—$R^{1.8}$, —N(CH$_3$)—N(CH$_3$)—CH$_2$—CH$_2$—$R^{1.5}$, —N(CH$_3$)—CH$_2$—$R^{1.10}$, —NH—$R^{1.2}$, $R^{1.3}$, —OH, —OCH$_3$ and —NH—CH$_2$—C≡CH.

Embodied is a compound of formula 1, wherein $R^{1.1}$ is selected from the group consisting of
—NH$_2$, —NH—C$_{1-4}$-alkyl, —N(CH$_3$)$_2$ and $R^{1.3}$, Embodied is a compound of formula 1, wherein $R^{1.2}$ is selected from the group consisting of
Formulas a.1 to a.14

a.1

a.2

a.3

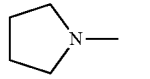

a.

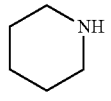

a.5

a.6

a.7

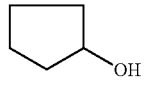

a.8

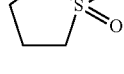

a.9

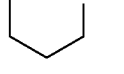

a.10

a.11 a.12

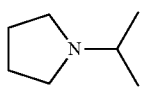
a.13
a.14
Embodied is a compound of formula 1, wherein $R^{1.3}$ is selected from the group consisting of formulas b.1 to b.37
b.1
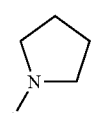
b.2
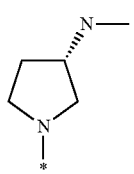
b.3
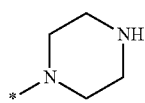
b.4
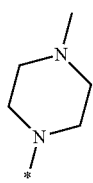
b.5
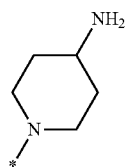
b.6
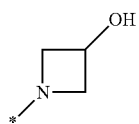
b.7
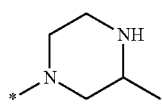
b.8
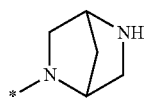
b.9
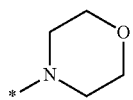
b.10
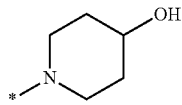
b.11
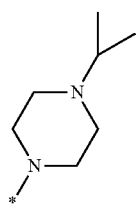
b.12
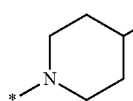
b.13
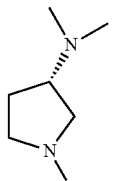
b.14
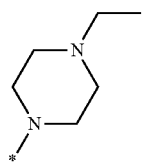
b.15
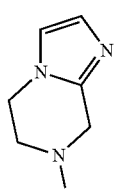
b.16
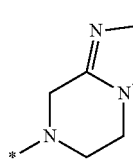
b.17
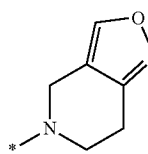
b.18
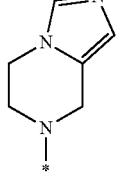
b.19

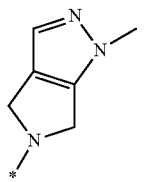 b.20
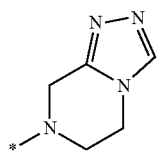 b.21
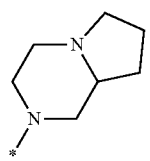 b.22
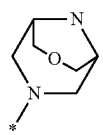 b.23
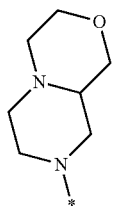 b.24
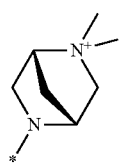 b.25
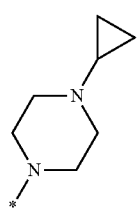 b.26
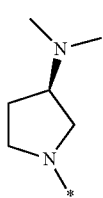 b.27
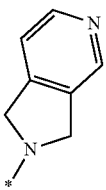 b.28
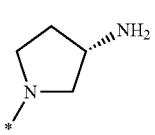 b.29
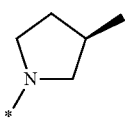 b.30
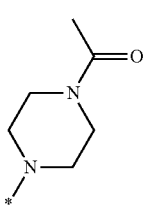 b.31
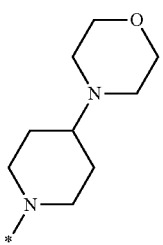 b.32
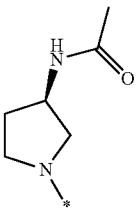 b.33
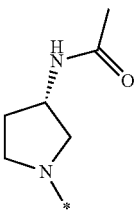 b.34
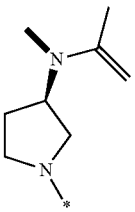 b.35

-continued

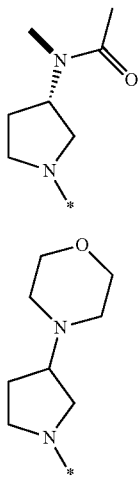

b.36 b.37

Embodied is a compound of formula 1, wherein
$R^{1.3}$ is a group of formula b.10.

Embodied is a compound of formula 1, wherein
$R^{1.4}$ is selected from the group consisting of morpholinyl, —$NH_2$, —OH, F, —NH—$CH_3$, —N($CH_3$)$_2$, —O—$CH_3$ and —$SO_2$—$CH_3$ Embodied is a compound of formula 1, wherein
$R^{1.5}$ is selected from the group consisting of morpholinyl, $NH_2$, —OH, —NH—$CH_3$ and —N($CH_3$)$_2$.

Embodied is a compound of formula 1, wherein
$R^{1.6}$ is selected from the group consisting of —CO-morpholinyl,
—CN, —$CF_3$, $CHF_2$, —C($CH_3$)$_2$OH, —C($CH_3$)$_2$CN and —C($CH_3$)$_2$NH$_2$
or is selected from the group consisting of formulas c.1 to c.12

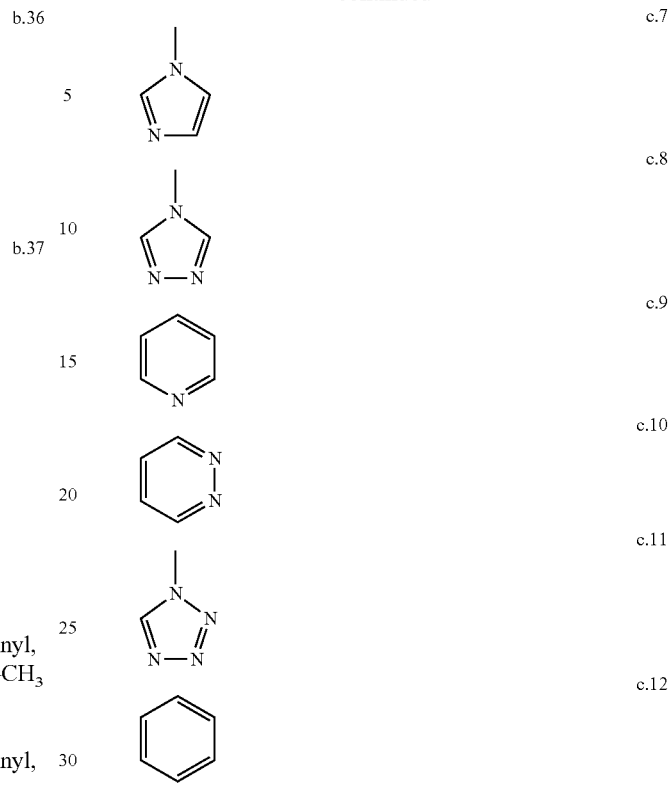

-continued

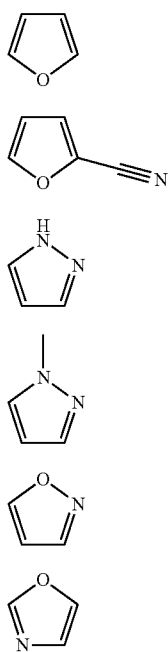

Embodied is a compound of formula 1, wherein
$R^{1.6}$ is selected from the group consisting of —CO-morpholinyl,
—CN, —$CF_3$, $CHF_2$, —C($CH_3$)$_2$OH, —C($CH_3$)$_2$CN and —C($CH_3$)$_2$NH$_2$ embodied is a compound of formula 1, wherein
$R^{1.6}$ is selected from the group consisting of formulas c.1 to c.12.

Embodied is a compound of formula 1, wherein
$R^{1.7}$ is —OH or —O—$CH_3$.

Embodied is a compound of formula 1, wherein
$R^{1.8}$ is —O—$CH_3$.

Embodied is a compound of formula 1, wherein
$R^{1.9}$ is selected from the group consisting of formulas c.1.

Embodied is a compound of formula 1, wherein
$R^{1.10}$ is selected from the group consisting of formulas c.3, c4, c.5, c.7, c8, and c.9.

Embodied is a compound of formula 1, wherein
$R^{1.11}$ is selected from the group consisting of formulas f.2, f.6, f.7, f.9 and f.10 each of the rings optionally substituted with a group independently selected from among $C_{1-3}$ alkyl, =O, —COO—$C_{1-4}$-alkyl and —O—$C_{1-3}$ alkyl.

Embodied is a compound of formula 1, wherein
$R^{1.11}$ is selected from the group consisting of formulas e.1 to e.9 each of the rings optionally substituted with a group independently selected from among $C_{1-3}$ alkyl, =O, —COO—$C_{1-4}$-alkyl and —O—$C_{1-3}$alkyl.

e.1

-continued

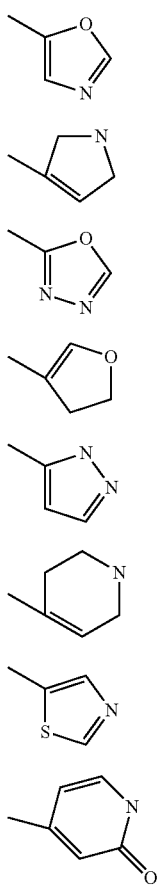

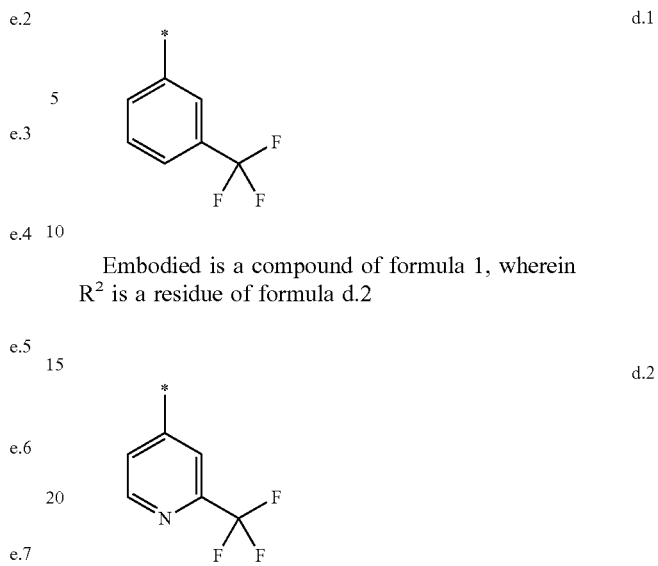

Embodied is a compound of formula 1, wherein $R^{1.11}$ is selected from the group consisting of formulas e.2, e.6, e.7 and e.9, each of the rings optionally substituted with a group independently selected from among $C_{1-3}$ alkyl, =O, —COO—$C_{1-4}$-alkyl and —O—$C_{1-3}$alkyl.

Embodied is a compound of formula 1, wherein $R^{1.12}$ is selected from the group consisting of —NH—$C_{1-4}$-alkyl, —NH—$R^{1.13}$ and a 6-membered N-containing heterocyclic ring, bound via N-atom to the core structure, optionally containing additional to the N-atom one to 3 heteroatoms independently selected from among N, O and S.

Embodied is a compound of formula 1, wherein $R^{1.12}$ is selected from the group consisting of —NH—$C_{1-4}$-alkyl, morpholinyl and tetrahydropyranyl.

Embodied is a compound of formula 1, wherein $R^{1.13}$ denotes a 6-membered heterocyclic ring, containing one to four heteroatoms independently selected from among N, O and S.

Embodied is a compound of formula 1, wherein $R^2$ is phenyl or pyridinyl, each substituted with $CF_3$ or $CHF_2$.

Embodied is a compound of formula 1, wherein $R^2$ is phenyl or pyridinyl, each substituted with $CF_3$.

Embodied is a compound of formula 1, wherein $R^2$ is phenyl substituted with $CF_3$.

Embodied is a compound of formula 1, wherein $R^2$ is a residue of formula d.1

Embodied is a compound of formula 1, wherein $R^2$ is a residue of formula d.2

Embodied is a compound of formula 1, wherein $R^3$ is H or methyl.

Embodied is a compound of formula 1, wherein $R^3$ is methyl.

Embodied is a compound of formula 1, wherein $R^3$ is hydrogen.

Embodied is a compound of formula 1, wherein n is 1.

Embodied is a compound of formula 1, wherein n is 2.

Embodied are the compounds of formula 1, wherein the compounds are selected from the group consisting of examples 2, 2.1, 11.2, 13.1, 15.8, 20.b, 21, 22, 23, 24 and 25.

Embodied are the compounds of formula 1, wherein the compounds are selected from the group consisting of examples 2, 2.1, 11.2, 13.1, 20.b, 21, 22, 23, 24 and 25.

Embodied are the compounds of formula 1, wherein the compounds are selected from the group consisting of examples 2, 20.b, 21, 22, 23, 24 and 25.

Embodied are the compounds of formula 1, wherein the compounds are selected from the group consisting of examples 2, 20.b, 21, 22, 23 and 24.

Any and each other of the definitions of $R^1$, $R^2$, $R^3$, n, $R^{1.1}$ to $R^{1.13}$, $R^{3.1}$ and $R^{3.2}$ may be combined with each other.

Preparation

The compounds according to the present invention and their intermediates may be obtained using methods of synthesis which are known to the one skilled in the art and described in the literature of organic synthesis. Preferably, the compounds are obtained in analogous fashion to the methods of preparation explained more fully hereinafter, in particular as described in the experimental section. In some cases, the order in carrying out the reaction steps may be varied. Variants of the reaction methods that are known to the one skilled in the art but not described in detail here may also be used. The general processes for preparing the compounds according to the invention will become apparent to the one skilled in the art studying the following schemes. Starting materials are commercially available or may be prepared by methods that are described in the literature or herein, or may be prepared in an analogous or similar manner. Any functional groups in the starting materials or intermediates may be protected using conventional protecting groups. These protecting groups may be cleaved again at a suitable stage within the reaction sequence using methods familiar to the one skilled in the art.

Intermediates VI are accessible using the synthetic route illustrated in Scheme 1; $R^1$ and $R^2$ have the meanings as defined hereinbefore and hereinafter. n has the meaning 1 or 2.

Alternatively, intermediate III can be prepared as described in Jochims et al. (*Chem. Ber.* 1982, 115, 860-870) by α-halogenation of aliphatic isocyanates, for example benzyl iso-cyanate, using for example a bromination agent, for example N-bromosuccinimide Isocyanates can be synthesized as described in U.S. Pat. No. 6,207,665 and in Scheme 1

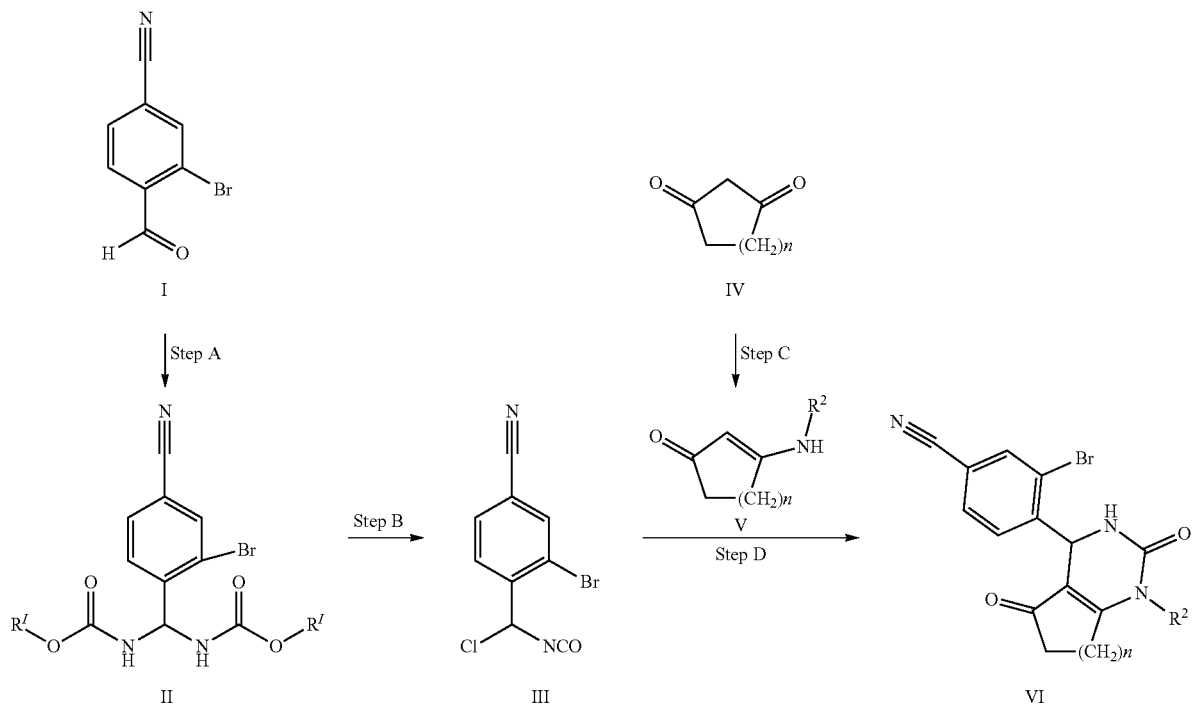

Intermediate II (Step A, intermediate I→intermediate II) can be prepared as described in Vovk et al. (*Synlett* 2006, 3, 375-378) or in PL2004/369318, by heating an aliphatic or aromatic aldehyde I with a carbamate, for example methyl carbamate ($R^1$=H), ethyl carbamate $R^1$=Et) (urethane) or benzyl carbamate ($R^1$=Bzl) in the presence of a strong Brønsted or a Lewis acid, for example sulfuric acid, hydrogen chloride, p-toluenesulfonic acid, Amberlyst 15, tetrafluoroboric acid, trifluoroacetic acid or boron trifluoride, either without solvent as a melt or in a suitable solvent, such as benzene, toluene, acetonitrile, diethyl ether, chloroform, acetic anhydride or mixtures thereof. The reaction takes place within 1 to 24 hours. Preferred reaction temperatures are between room temperature and 160° C., or the boiling point of the solvent, respectively. Preferably the reaction is done with molten ethyl carbamate as reactant and a catalytic amount of concentrated sulfuric acid at temperatures of 140-160° C. without any additional solvent.

The chlorination (Step B, intermediate II→intermediate III) can be done as described in Vovk et al. (*Synlett* 2006, 3, 375-378) and Sinitsa et al. (*J. Org. Chem. USSR* 1978, 14, 1107) by heating intermediate II together with a chlorinating agent, for example phosphorous pentachloride, phosphoryl chloride or sulfuryl chloride in an organic solvent, for example benzene or toluene. The reaction takes place within 1 to 24 hours. Preferred reaction temperatures are between 50° C. and 150° C.

Charalambides et al. (*Synth. Commun.* 2007, 37, 1037-1044), by reacting an amine precursor with phosgene.

Intermediates V (Step C, intermediate IV→intermediates V) can be prepared as described in Chen et al. (*Synth. Commun.* 2010, 40, 2506-2510) and Tietcheu et al. (*J. Heterocyclic Chem.* 2002, 39, 965-973) by reacting cyclopentane-1,3-dione (IV, n=1) or cyclohexane-1,3-dione (IV, n=2) and an aliphatic or aromatic amine in the presence of a catalyst, for example Ytterbium triflate[Yb(OTf)$_3$] or an acid, for example hydrogen chloride or p-toluenesulfonic acid, optionally in a solvent, for example water, acetic acid, acetonitrile, benzene, toluene. The reaction takes place within 1-24 hours. Preferred reaction temperatures are between room temperature and 120° C., most preferred room temperature.

Alternatively, intermediates V can be prepared as described in Scott et al. (*J. Med. Chem.* 1993, 36, 1947-1955) by direct condensation of the 1,3-dicarbonyl compound with an amine under reflux in a suitable solvent, for example benzene or toluene with azeotropic removal of water. Alternatively, intermediates V can be prepared as described in Mariano et al. (*J. Org. Chem.* 1984, 49, 220-228) by reacting an amine with 3-chloro-2-cyclopenten-1-one, which can be prepared from cyclopentane-1,3-dione.

Intermediates VI (Step D, intermediate III→intermediates VI) can be prepared as described in Vovk et al. (*Synlett* 2006, 3, 375-378), Vovk et al. (*Russ. J. Org. Chem.* 2010, 46, 709-715) and Kushnir et al. (*Russ. J. Org. Chem.* 2011, 47, 1727-1732) by reacting intermediate III with intermediates V in an organic solvent, for example dichloromethane, chloroform, benzene or toluene. The reaction takes place within 1-24 hours. Preferred reaction temperatures are between 0° C. and 100° C.

Additionally to the synthetic route depicted in Scheme 1, intermediates VI are also accessible using the synthetic route depicted in Scheme 2, R² have the meanings as defined hereinbefore and hereinafter. n has the meaning of 1 or 2.

Scheme 2

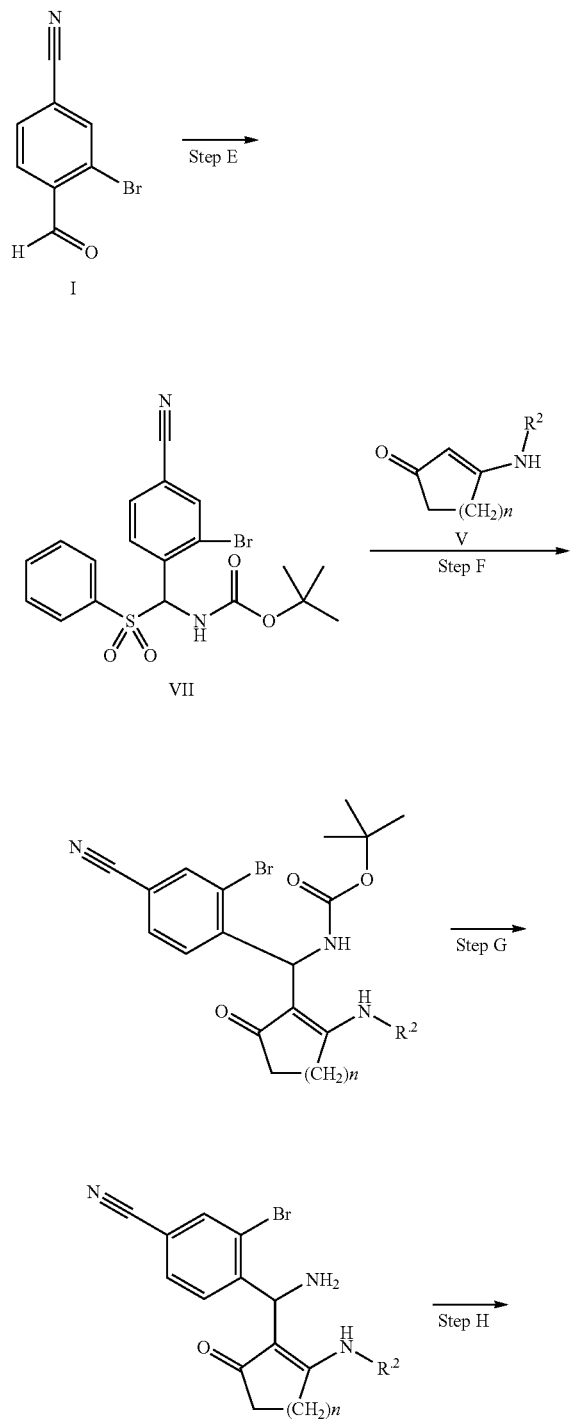

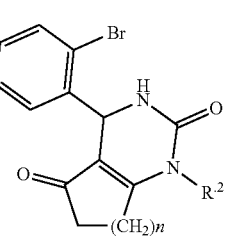

VI

Intermediate VII (Step E, intermediate I→intermediate VII) can be prepared as described in Best et al. (*J. Am. Chem. Soc.* 2012, 134, 18193-18196) or in Yang et al. (*Org. Synth.* 2009, 86, 11-17), by reacting an aromatic aldehyde I with a suitable sulfinate, for example sodium benzenesulfinic acid, and a suitable carbamate, for example methyl carbamate or tert-butyl carbamate, in the presence of a suitable acid, for example formic acid, in a suitable solvent, for example tetrahydrofurane, ethanol, methanol or a mixture of solvents, for example tetrahydrofurane and water. Alternatively, as described in Reingruber et al. (*Adv. Synth. Catal.* 2009, 351, 1019-1024) or in WO06136305, a suitable lewis acid, for example trimethylsilyl chloride, can be used as acid and acetonitrile or toluene can be used as solvent. The reaction takes place within 1-6 days. Preferred reaction temperatures are between 0° C. and 50° C., most preferred room temperature.

Intermediates VIII (Step F, intermediate VII→intermediates VIII) can be prepared in analogy to the method described for the preparation of compounds of the invention VI (Scheme 1, Step D, intermediate III→compound of the invention VI), by reacting intermediate VII with intermediates V in the presence of a suitable base, for example sodium hydride or sodium tert-butoxide, in a suitable organic solvent, for example tetrahydrofurane or 2-methyltetrahydrofuran. The reaction takes place within 1-24 h. Preferred reaction temperatures are between 0° C. and 50° C., most preferred room temperature.

Intermediate IX (Step G, intermediates VIII→intermediates IX) can be prepared by reacting intermediates VIII with a suitable acid, for example hydrogen chloride, in a suitable solvent, for example 1,4-dioxane. The reaction takes place between 1-72 hours. Preferred reaction temperatures are between 0° C. and room temperature, most preferred room temperature.

Intermediates VI (Step H, intermediates IX intermediates VI) can be prepared as described in Csütörtöki et al. (*Tetrahedron Lett.* 2011, 67, 8564-8571) or in WO11042145, by reacting intermediates IX with a suitable reagent, for example phosgene, triphosgene or carbonyl diimidazole, in the presence of a suitable base, for example triethylamine, N,N-diisopropylethylamine, pyridine or sodium carbonate, in a suitable solvent, for example acetonitrile, dichloromethane or toluene. The reaction takes place between 1-72 hours. Preferred reaction temperatures are between 0° C. and 50° C., most preferred room temperature Intermediates VII are accessible using the synthetic route illustrated in Scheme 3; R² and R³·¹ have the meanings as defined hereinbefore and hereinafter. n has the meaning of 1 or 2.

Scheme 3

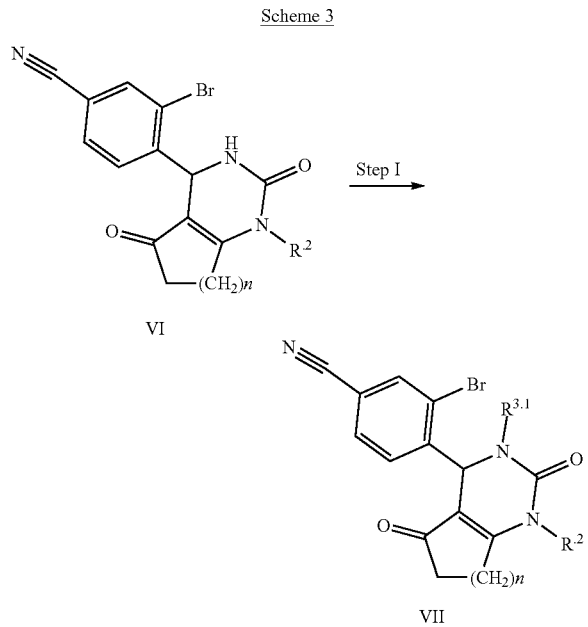

Intermediates VII (Step I, intermediates VI→intermediates VII) can be prepared as described in WO04024700 by reacting intermediates VI with an alkylating agent, for example a dialkyl sulfate, for example dimethyl sulfate, an alkyl halide, for example methyl iodide or an alkyl sulfonylate, for example benzyl tosylate, in the presence of a suitable base, for example sodium hydride, sodium hydroxide, cesium carbonate, lithium diisopropylamide, potassium hexamethyldisilazide, lithium hexamethyldisilazide, an organolithium reagent, for example tert-butyllithium or a Grignard reagent, for example isopropylmagnesiumchloride, in an organic solvent, for example tetrahydrofurane, N,N-dimethylformamide, acetonitrile, 1,4-dioxane, dichloromethane or toluene. The reaction takes place within 1-72 hours. Preferred reaction temperatures are between 0° C. and 100° C.

Compounds according to the present invention IX, X and XII and intermediates XI and VIII are accessible via the synthetic routes depicted in scheme 4; $R^{II}$, $R^{1.1}$, $R^{1.11}$, $R^2$ and $R^{3.1}$ have the meanings as defined hereinbefore and hereinafter. n has the meaning 1 or 2.

Scheme 4

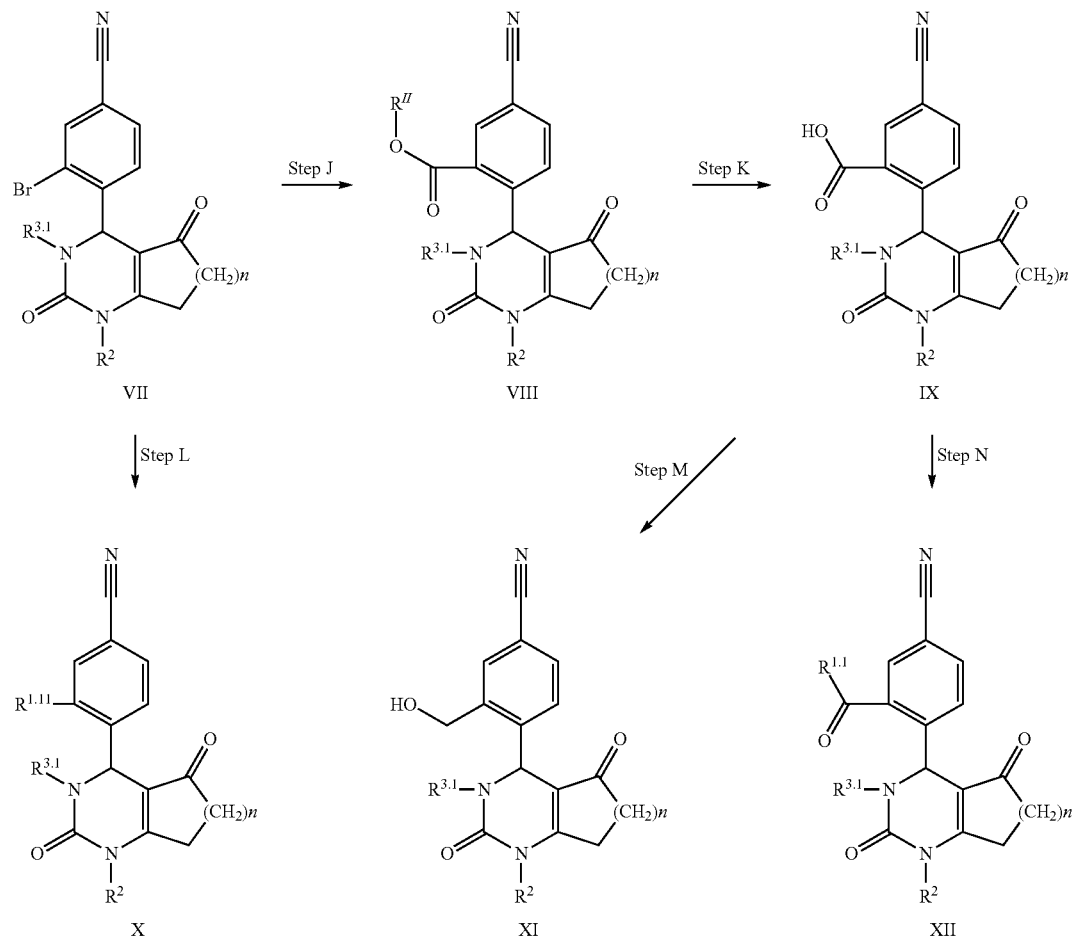

Compounds of the invention X (Step L, intermediates VII→compounds of the invention X) can be prepared by reacting intermediates VII with a boronic acid derivative (acid or ester, e.g. pinacol ester) in the presence of a suitable catalyst such as 1,1'-Bis(di-tert-butylphosphino)ferrocene palladium dichloride or [1,1'-bis(diphenylphosphino)-ferrocene]-dichloropalladium(II) as a 1:1 complex with dichloromethane, and in the presence of a a) base, for example alkali carbonates, hydrogencarbonates, phosphates, hydrogenphosphates or acetates, especially cesium carbonate, in an organic solvent, for example tetrahydrofurane, N,N-dimethylformamide, acetonitrile, 1,4-dioxane or dichloromethane. The reaction takes place within 1-72 hours. Preferred reaction temperatures are between 0° C. and the boiling point of the solvent, for example 80° C.

Intermediates VIII (Step J, intermediates VII→intermediates VIII can be prepared by reacting intermediates VII with carbon monoxide in the presence of a suitable catalyst such as 1,1-bis(diphenylphosphino)-ferrocen with palladium (II)-acetate, 1,1'-Bis(di-tert-butyl-phosphino)ferrocene palladium dichloride or [1,1'-bis(diphenylphosphino)-ferrocene]-dichloropalladium(II) as a 1:1 complex with dichloromethane, and in the presence of a base, for example alkali carbonates, hydrogencarbonates, phosphates, hydrogenphosphates or acetates, especially sodium acetate, in an alcohol, preferred a primary alcohol, most preferred methanol or ethanol ($R^H$=Me or Et). The reaction takes place within 1 h-6 days. Preferred reaction temperatures are between r.t. and 150° C., for example 100° C. The reaction is performed in an autoclave under elevated pressure, preferably between 2 and 10 bar, most preferred 5 bar.

Compounds of the invention IX (Step K, intermediates VIII→compounds of the invention IX) can be prepared by basic hydrolysis of intermediates VIII using e.g. alkali hydroxides like lithium hydroxide in a mixture of water and a polar organic solvent like THF, dioxane, DMF, DMSO or acetonitrile, preferably dioxane. The reaction takes place within 10 min to 24 h. Preferred reaction temperatures are between 0° C. and 100° C., for example r.t. The reaction has to be monitored by TLC or HPLC to minimize decomposition of the molecule.

Intermediates XI (Step M, compounds of the invention IX→intermediates XI) can be prepared by reaction of compounds of the invention IX with 1,1'-carbonyldiimidazole zs followed by reaction with reducing agents like complex borohydrides (stable enough in water), preferably sodium borohydride in a mixture of water and a polar organic solvent like THF or dioxane. The reaction takes place within 10 min to 24 h. Preferred reaction temperatures are between −20° C. and 25° C., for example 5-10° C.

Compounds of the invention XII (Step N, compounds of the invention IX→compounds of the invention XII) can be prepared by reaction of compounds of the invention IX with an appropriate amine or ammonium salt in the presence of a sufficient amount of a base like N—N-diisopropylethyl amine (DIPEA) in a polar solvent like DMF, THF or dioxane using standard literature procedures. The carboxylic acids IX has to be activated in advance by reaction with an activating agent such as O-(7-Azabenzotriazol-1-yl)-N,N,N',N'-tetramethyluronium hexafluorophosphate (HATU) or O-(Benzotriazol-1-yl)-N,N,N',N'-tetramethyluroniumtetrafluoroborate (TBTU) and N,N-diisopropylethyl amine (DIPEA). The reaction takes place within 10 min to 24 h. Preferred reaction temperatures are between −20° C. and 80° C., preferably at r.t.

a) Compounds according to the present invention XIII are accessible via the synthetic routes depicted in scheme 5; $R^{1.11}$ and $R^2$ have the meanings as defined hereinbefore and hereinafter. n has the meaning 1 or 2.

Scheme 5

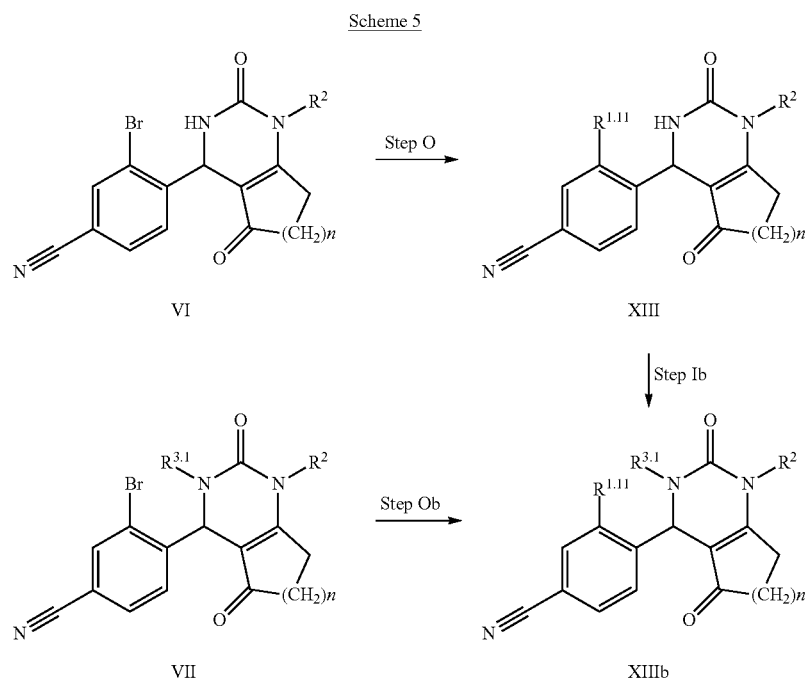

Compounds of the invention XIII or XIIIb (Step O, intermediates VI→compounds of the invention XIII; or Step Ob, intermediates VII→compounds of the invention XIIIb) can be prepared by reacting intermediates VI or VII with a boronic acid derivative (acid or ester, e.g. pinacol ester) in the presence of a suitable catalyst such as 1,1'-Bis(di-tert-butylphosphino)ferrocene palladium dichloride or [1,1'-bis (diphenylphosphino)-ferrocene]dichloropalladium(II) as a 1:1 complex with dichloromethane, and in the presence of a base, for example alkali carbonates, hydrogencarbonates, phosphates, hydrogenphosphates or acetates, especially cesium carbonate, in an organic solvent, for example tetrahydrofurane, N,N-dimethylformamide, acetonitrile, 1,4-dioxane or dichloromethane. The reaction takes place within 1-72 hours. Preferred reaction temperatures are between 0° C. and the boiling point of the solvent, for example 80° C.

Alternatively, compounds of the invention XIIIb (Step Ib, intermediates XIII→compounds of the invention XIIIb) can be prepared as described in WO04024700 by reacting intermediates XIII with an alkylating agent, for example a dialkyl sulfate, for example dimethyl sulfate, an alkyl halide, for example methyl iodide or an alkyl sulfonylate, for example benzyl tosylate, in the presence of a suitable base, for example sodium hydride, sodium hydroxide, cesium carbonate, lithium diisopropylamide, potassium hexamethyldisilazide, lithium hexamethyldisilazide, an organolithium reagent, for example tert-butyllithium or a Grignard reagent, for example isopropylmagnesiumchloride, in an organic solvent, for example tetrahydrofurane, N,N-dimethylformamide, acetonitrile, 1,4-dioxane, dichloromethane or toluene. The reaction takes place within 1-72 hours. Preferred reaction temperatures are between 0° C. and 100° C.

Compounds according to the present invention XIV and XVI and intermediates XV are accessible via the synthetic routes depicted in scheme 6; $R^{1.11}$, $R^2$, $R^{3.1}$ and $T^{3.2}$ have the meanings as defined hereinbefore and hereinafter. n has the meaning 1 or 2.

Compounds of the invention XIV (Step P, compounds of the invention XIII→compounds of the invention XIV) can be prepared as described in WO07137874, by reacting compounds of the invention XIII with a sulfonylating agent, for example methanesulfonyl chloride or para-toluenesulfonyl chloride in the presence of a base, for example sodium hydride, lithium diisopropylamide, potassium hexamethyldisilazide, lithium hexamethyldisilazide, an organolithium reagent, for example tert-butyllithium or a Grignard reagent, for example iso-propylmagnesiumchloride, in an organic solvent, for example tetrahydrofurane, N,N-dimethylformamide, acetonitrile, 1,4-dioxane or dichloromethane. The reaction takes place within 1-72 hours. Preferred reaction temperatures are between 0° C. and room temperature.

Intermediates XV (Step Q, compounds of the invention XIII→intermediates XV) can be prepared as described in WO09080199, by reacting compounds of the invention XIII with 4-nitrophenyl chloroformate in the presence of a base, for example triethylamine, N,N-diisopropylethylamine or N-methylmorpholine, optionally in the presence of a catalyst, for example 4-dimethylaminopyridine, in an organic solvent, for example dichloromethane, tetrahydrofurane, acetonitrile or N,N-dimethylformamide. The reaction takes place within 1-24 hours. Preferred reaction temperatures are between 0° C. and 50° C., most preferred room temperature.

Compounds of the invention XVI (Step R, intermediates XV→compounds of the invention XVI) can be prepared as described in WO09080199, by reacting intermediates XV with an amine $R^{3.1}R^{3.2}NH_2$ in an organic solvent, for example dichloromethane, acetonitrile, tetrahydrofurane, 1,4-dioxane, toluene or N,N-dimethylformamide. The reaction takes place within 1-72 hours. Preferred reaction temperatures are between 0° C. and 50° C., most preferred room temperature.

Scheme 6

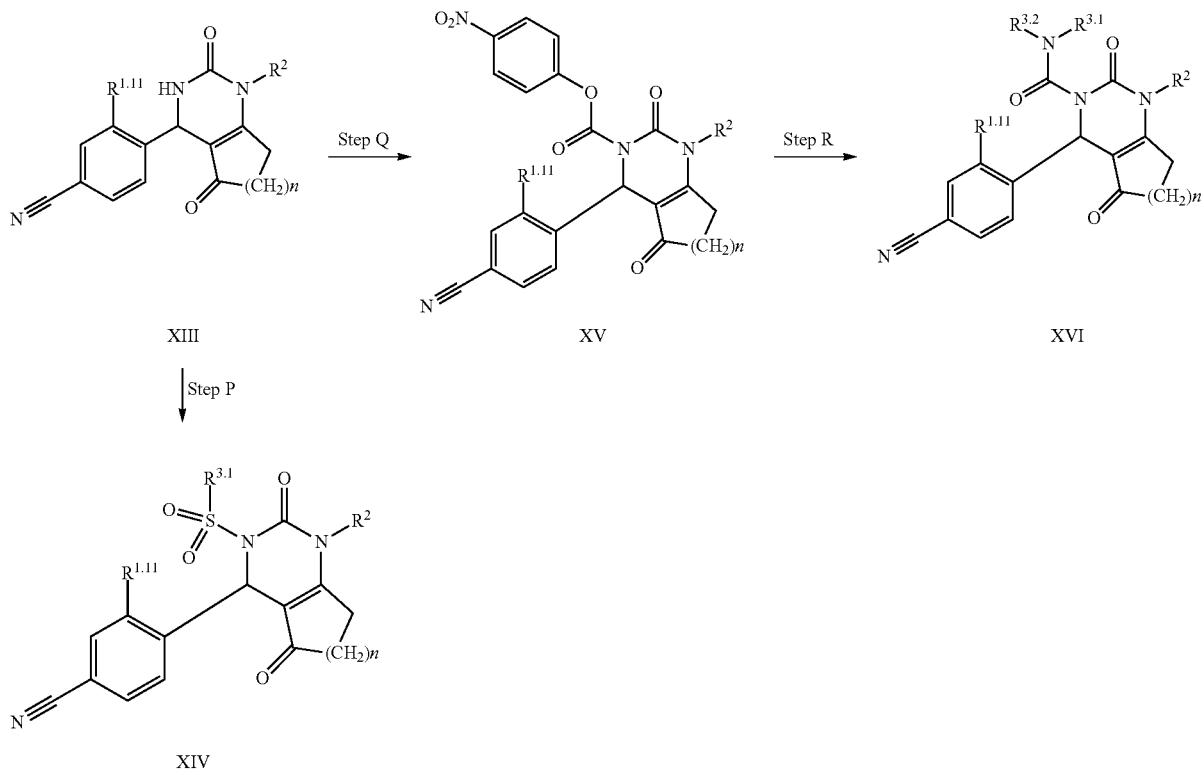

Compounds according to the present invention XVIII and intermediates XVII are accessible via the synthetic routes depicted in scheme 7; $R^{1.12}$, $R^2$ and $R^{3.1}$ have the meanings as defined hereinbefore and hereinafter. n has the meaning 1 or 2.

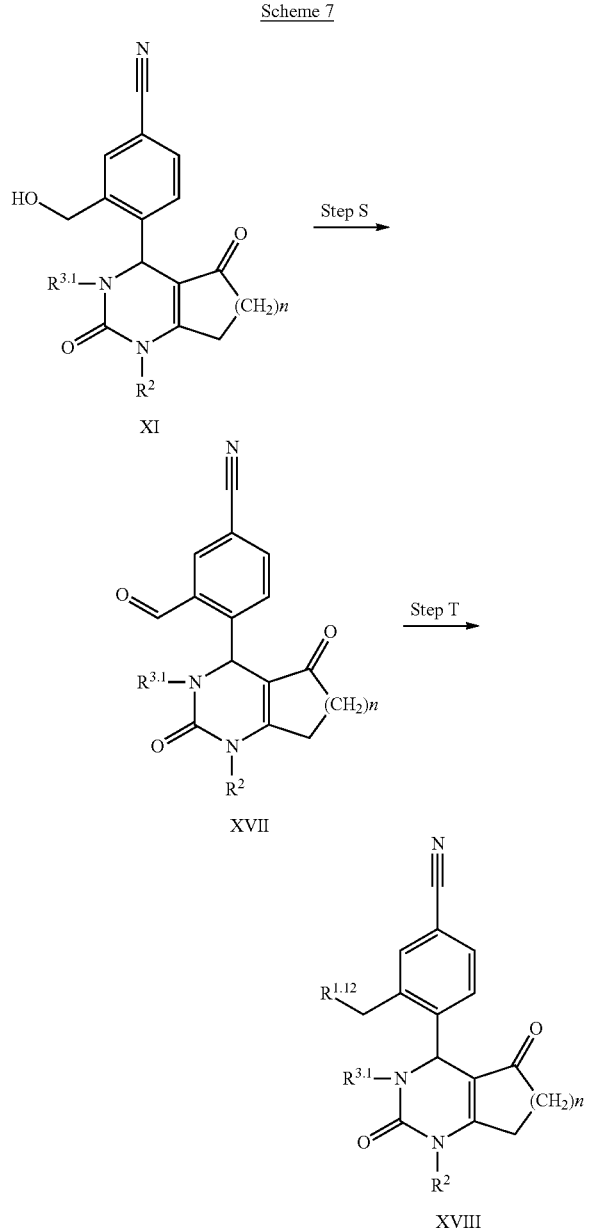

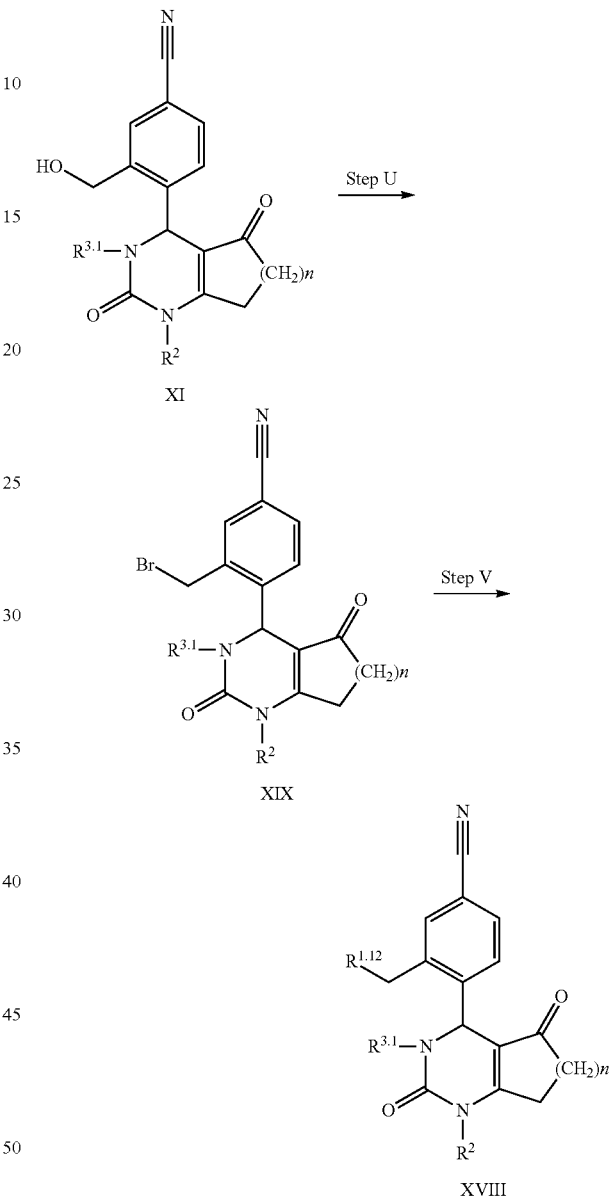

Intermediates XVII (Step S, compounds of the invention XI→intermediates XVII) can be prepared by reacting compounds of the invention XI with Dess-Martin periodinane in an organic solvent, for example dichloromethane, acetonitrile, tetrahydrofurane or 1,4-dioxane. The reaction takes place within 1-24 hours. Preferred reaction temperatures are between 0° C. and 50° C., most preferred room temperature.

Compounds of the invention XVIII (Step T, intermediates XVII→compounds of the invention XVIII) can be prepared by reacting intermediates XVII with an amine $R^{1.12}$ in the presence of a reducing reagent like sodium triacetoxyborohydride or sodium cyanoborohydride in an organic solvent, for example N,N-dimethylformamide or 1,2-dichloroethane. Preferred reaction temperatures are between 0° C. and 50° C., most preferred room temperature.

Intermediates XIX (Step U, compounds of the invention XI→intermediates XIX) can be prepared by reacting compounds of the invention XI with a halogenating reagent, for instance phosphorus tribromide in an organic solvent, for example dichloromethane, The reaction takes place within 1-24 hours. Preferred reaction temperatures are between 0° C. and 50° C.

Compounds of the invention XVIII (Step V, intermediates XIX→compounds of the invention XVIII) can be prepared by reacting intermediates XIX with an amine $R^{1.12}$ in the presence of a base like potassium carbonate in an organic solvent, for example N,N-dimethylformamide or 1,2-dichloroethane. Preferred reaction temperatures are between 0° C. and 100° C.

Preliminary Remarks

The term room temperature denotes a temperature of about 20° C. As a rule, $^1$H NMR spectra and/or mass spectra have been obtained of the compounds prepared. Compounds given with a specific configuration at a stereocenter are isolated as pure isomers.

The retention times given are measured under the following conditions (TFA: trifluoroacetic acid, DEA: diethylamine, scCO$_2$: supercritical carbon dioxide):

| Method Name: | V011_S01 |
| --- | --- |
| Column: | XBridge C18, 4.6 × 30 mm, 3.5 μm |
| Column Supplier: | Waters |

| Gradient/ Solvent Time [min] | % Solvent [H$_2$O, 0.1% NH$_3$] | % Solvent [acetonitrile] | Flow [ml/min] | Temp [° C.] |
| --- | --- | --- | --- | --- |
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

| Method Name: | X012_S01 |
| --- | --- |
| Column: | XBridge BEH C18, 2.1 × 30 mm, 1.7 μm |
| Column Supplier: | Waters |

| Gradient/ Solvent Time [min] | % Solvent [H$_2$O, 0.1% TFA] | % Solvent [acetonitrile] | Flow [ml/min] | Temperature [° C.] |
| --- | --- | --- | --- | --- |
| 0.0 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

| Method Name: | X012_S02 |
| --- | --- |
| Column: | XBridge BEH C18, 2.1 × 30 mm, 1.7 μm |
| Column Supplier: | Waters |

| Gradient/ Solvent Time [min] | % Solvent [H$_2$O, 0.1% TFA] | % Solvent [acetonitrile] | Flow [ml/min] | Temperature [° C.] |
| --- | --- | --- | --- | --- |
| 0.0 | 99 | 1 | 1.3 | 60 |
| 0.02 | 99 | 1 | 1.3 | 60 |
| 1.00 | 0 | 100 | 1.3 | 60 |
| 1.10 | 0 | 100 | 1.3 | 60 |

| Method Name: | X018_S01 |
| --- | --- |
| Column: | Sunfire C18, 2.1 × 30 mm, 2.5 μm |
| Column Supplier: | Waters |

| Gradient/ Solvent Time [min] | % Solvent [H$_2$O, 0.1% TFA] | % Solvent [acetonitrile] | Flow [ml/min] | Temperature [° C.] |
| --- | --- | --- | --- | --- |
| 0.0 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

| Method Name: | Z001_002 |
| --- | --- |
| Column: | XBridge C18, 3 × 30 mm, 2.5 μm |
| Column Supplier: | Waters |

| Gradient/ Solvent Time [min] | % Solvent [H$_2$O, 0.1% TFA] | % Solvent [methanol] | Flow [ml/min] | Temperature [° C.] |
| --- | --- | --- | --- | --- |
| 0.0 | 95 | 5 | 2.2 | 60 |
| 0.05 | 95 | 5 | 2.2 | 60 |
| 1.40 | 0 | 100 | 2.2 | 60 |
| 1.80 | 0 | 100 | 2.2 | 60 |

| Method Name: | Z011_S03 |
| --- | --- |
| Column: | XBridge C18, 3 × 30 mm, 2.5 μm |
| Column Supplier: | Waters |

| Gradient/ Solvent Time [min] | % Solvent [H$_2$O, 0.1% NH$_3$] | % Solvent [acetonitrile] | Flow [ml/min] | Temperature [° C.] |
| --- | --- | --- | --- | --- |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method Name: | Z018_S04 |
| --- | --- |
| Column: | Sunfire, 3 × 30 mm, 2.5 μm |
| Column Supplier: | Waters |

| Gradient/ Solvent Time [min] | % Solvent [H$_2$O, 0.1% TFA] | % Solvent [acetonitrile] | Flow [ml/min] | Temperature [° C.] |
| --- | --- | --- | --- | --- |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method Name: | 003_CA03 |
| --- | --- |
| Column: | Sunfire, 3 × 30 mm, 3.5 μm |
| Column Supplier: | Waters |

| Gradient/ Solvent Time [min] | % Solvent [H$_2$O, 0.1% TFA] | % Solvent [acetonitrile] | Flow [ml/min] | Temperature [° C.] |
| --- | --- | --- | --- | --- |
| 0.00 | 98 | 2 | 2.0 | 60 |
| 0.30 | 98 | 2 | 2.0 | 60 |
| 1.50 | 0 | 100 | 2.0 | 60 |
| 1.60 | 0 | 100 | 2.0 | 60 |

| Method Name: | 003_CA04 |
| --- | --- |
| Column: | XBridge C18, 3 × 30 mm, 2.5 μm |
| Column Supplier: | Waters |

| Gradient/ Solvent Time [min] | % Solvent [H$_2$O, 0.1% NH$_3$] | % Solvent [acetonitrile] | Flow [ml/min] | Temperature [° C.] |
| --- | --- | --- | --- | --- |
| 0.0 | 98 | 2 | 2.0 | 60 |
| 1.2 | 0 | 100 | 2.0 | 60 |
| 1.4 | 0 | 100 | 2.0 | 60 |

| Method Name: | 004_CA05 |
| --- | --- |
| Column: | XBridge C18, 3 × 30 mm, 2.5 μm |
| Column Supplier: | Waters |

| Gradient/ Solvent Time [min] | % Solvent [H$_2$O, 0.1% NH$_3$] | % Solvent [acetonitrile] | Flow [ml/min] | Temperature [° C ] |
| --- | --- | --- | --- | --- |
| 0.0 | 98 | 2 | 2.0 | 60 |
| 1.2 | 0 | 100 | 2.0 | 60 |
| 1.4 | 0 | 100 | 2.0 | 60 |

| Method Name: | 005_CA01 |
| --- | --- |
| Column: | SunFire C18, 3.0 × 30 mm, 2.5 μm |
| Column Supplier: | Waters |

| Gradient/ Solvent Time [min] | % Solvent [H$_2$O, 0.1% TFA] | % Solvent [acetonitrile] | Flow [ml/min] | Temperature [° C.] |
| --- | --- | --- | --- | --- |
| 0.0 | 98 | 2 | 2.0 | 60.0 |
| 1.2 | 0 | 100 | 2.0 | 60.0 |
| 1.4 | 0 | 100 | 2.0 | 60.0 |

| Method Name: | 006_CA07 |
| --- | --- |
| Column: | XBridge C18_3.0 × 30 mm, 2.5 μm |
| Column supplier: | Waters |

| Gradient/ Solvent Time [min] | % Sol [H2O 0.1% NH4OH] | % Sol [Acetonitrile] | Flow [ml/min] | Temp [° C.] |
| --- | --- | --- | --- | --- |
| 0.0 | 95.0 | 5.0 | 1.5 | 60.0 |
| 1.3 | 1.0 | 99.0 | 1.5 | 60.0 |

| Method Name: | 006_CA07 |
| --- | --- |
| 1.5 | 1.0 | 99.0 | 1.5 | 60.0 |
| 1.6 | 95.0 | 5.0 | 1.5 | 60.0 |

| Method Name: | I_IC_25_MeOH_NH$_3$ |
| --- | --- |
| Column: | Chiralpak IC 4.6 × 250 mm, 5 μm |
| Column Supplier: | Daicel |

| Gradient/ Solvent Time [min] | % Solvent [MeOH, 0.2% NH$_3$] | % Solvent [scCO$_2$] | Flow [ml/min] | Temperature [° C.] | Back Pressure [bar] |
| --- | --- | --- | --- | --- | --- |
| 10 min | 25 | 75 | 4 | 40 | 150 |

| Method Name: | I_IC_30_MeOH_NH$_3$ |
| --- | --- |
| Column: | Chiralpak IC 4.6 × 250 mm, 5 μm |
| Column Supplier: | Daicel |

| Gradient/ Solvent Time [min] | % Solvent [MeOH, 0.2% NH$_3$] | % Solvent [scCO$_2$] | Flow [ml/min] | Temperature [° C.] | Back Pressure [bar] |
| --- | --- | --- | --- | --- | --- |
| 0 | 30 | 70 | 4 | 40 | 150 |
| 10 | 30 | 70 | 4 | 40 | 150 |

| Method Name: | I_IB_15_MeOH_NH3 |
| --- | --- |
| Column: | Chiralpak IB 4.6 × 250 mm, 5 μm |
| Column Supplier: | Daicel |

| Gradient/ Solvent Time [min] | % Solvent [MeOH, 20 mM NH$_3$] | % Solvent [scCO$_2$] | Flow [ml/min] | Temperature [° C.] | Back Pressure [bar] |
| --- | --- | --- | --- | --- | --- |
| 0 | 15 | 85 | 4 | 40 | 150 |
| 10 | 15 | 85 | 4 | 40 | 150 |

| Method Name: | I_IC10_ETOH_NH3.M |
| --- | --- |
| Column: | Chiralpak IC 4.6 × 250 mm, 5 μm |
| Column Supplier: | Daicel |

| Gradient/ Solvent Time [min] | % Solvent [EtOH, 20 mM NH$_3$] | % Solvent [scCO$_2$] | Flow [ml/min] | Temperature [° C.] | Back Pressure [bar] |
| --- | --- | --- | --- | --- | --- |
| 0 | 10 | 90 | 4 | 40 | 150 |
| 10 | 10 | 90 | 4 | 40 | 150 |

| Method Name: | Z017_S04 |
| --- | --- |
| Column: | Stable Bond, 3 × 30 mm, 1.8 μm |
| Column Supplier: | Agilent |

| Gradient/ Solvent Time [min] | % Solvent [H$_2$O, 0.1% TFA] | % Solvent [acetonitrile] | Flow [ml/min] | Temp [° C.] |
| --- | --- | --- | --- | --- |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method Name: | I_IA_20_MeOH_NH3 |
| --- | --- |
| Device-Description | Agilent 1260 SFC with DAD and MS |
| Column | Daicel Chiralpak ® IA |
| Column Dimension | 4.6 × 250 mm |
| Particle Size | 5 μm |

| Solvent Gradient time [min] | % Solvent [scCO$_2$] | % Solvent [MeOH], 20 mM ammonia | Flow [ml/min] | Temperature [° C.] | Backpressure [bar] |
| --- | --- | --- | --- | --- | --- |
| 0.00 | 80 | 20 | 4 | 40 | 150 |
| 10.00 | 80 | 20 | 4 | 40 | 150 |

| Method Name: | I_IA_20_IPA_NH3 |
| --- | --- |
| Device-Description | Agilent 1260 SFC with DAD and MS |
| Column | Daicel Chiralpak ® IA |
| Column Dimension | 4.6 × 250 mm |
| Particle Size | 5 μm |

| Solvent Gradient time [min] | % Solvent [scCO$_2$] | % Solvent [iPrOH], 20 mM ammonia | Flow [ml/min] | Temp [° C.] | Back-pressure [bar] |
| --- | --- | --- | --- | --- | --- |
| 0.00 | 80 | 20 | 4 | 40 | 150 |
| 10.00 | 80 | 20 | 4 | 40 | 150 |

| Method Name: | I_IB_20_MeOH_NH3 |
|---|---|
| Device-Description | Agilent 1260 SFC with DAD and MS |
| Column | Daicel Chiralpak® IB |
| Column Dimension | 4.6 × 250 mm |
| Particle Size | 5 μm |

| Solvent Gradient time [min] | % Solvent [scCO$_2$] | % Solvent [MeOH], 20 mM ammonia] | Flow [ml/min] | Temp [° C.] | Backpressure [bar] |
|---|---|---|---|---|---|
| 0.00 | 80 | 20 | 4 | 40 | 150 |
| 10.00 | 80 | 20 | 4 | 40 | 150 |

Syntheses of Starting Materials

The following starting material is prepared as described in the literature cited: 3-(3-(trifluoromethyl)phenylamino)cyclopent-2-enone: *Aust. J. Chem.* 2005, 58, 870-876.

Intermediate 1

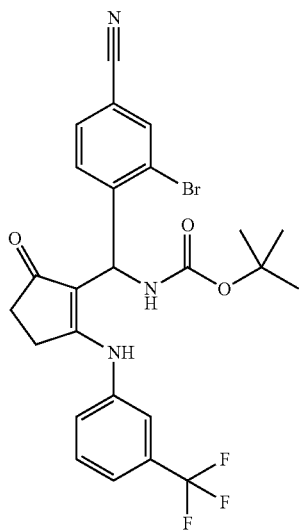 [SMILES: CC(C)(C)OC(=O)NC(C1=C(Nc2cccc(C(F)(F)F)c2)CCC1=O)c1ccc(C#N)cc1Br]

tert-Butyl (2-Bromo-4-cyanophenyl)(5-oxo-2-(3-(trifluoromethyl)phenylamino)cyclopent-1-enyl)methylcarbamate Step 1 tert-Butyl (2-Bromo-4-cyanophenyl)(phenylsulfonyl)methylcarbamate

Formic acid (3.9 mL, 104 mmol) is added to a solution of tert-butyl carbamate (1.90 g, 16.2 mmol), 2-bromo-4-cyanobenzaldehyde (3.41 g, 16.2 mmol) and sodium benzenesulfinate (2.67 g, 16.2 mmol) in a mixture of tetrahydrofurane (7.0 mL) and water (60 mL). The mixture is stirred at room temperature for 6 days. Water (180 mL) is added and the precipitate is filtered and washed with water. The precipitate is treated with tert-butyl methyl ether (30 mL), and the mixture is stirred for 30 min. The precipitate is filtered, washed with tert-butyl methyl ether and dried. Yield: 3.35 g. ESI mass spectrum: [($^{79}$Br)-M+H]$^+$=451, [($^{81}$Br)-M+H]$^+$=453; Retention time HPLC: 0.66 min (method X012_S01).

Step 2 tert-Butyl (2-Bromo-4-cyanophenyl)(5-oxo-2-(3-(trifluoromethyl)phenylamino)cyclopent-1-enyl)methylcarbamate Sodium hydride (60% in mineral oil, 360 mg, 9.00 mmol) is added in portions to a mixture of 3-(3-(trifluoromethyl)phenylamino)cyclopent-2-enone (2.16 g, 8.96 mmol) and 2-methyltetrahydrofuran (30 mL). After 30 min tert-butyl (2-bromo-4-cyanophenyl)-(phenyl-sulfonyl)methylcarbamate (Step 1, 3.35 g, 7.43 mmol) is added and the mixture is stirred at room temperature for 2 h. Water is added and the phases are separated. The aqueous phase is extracted twice with ethyl acetate and the combined organic phases are washed with water, dried over MgSO$_4$ and concentrated under reduced pressure. The residue is treated with tert-butyl methyl ether and the mixture is stirred for 15 min. The precipitate is filtered, washed with tert-butyl methyl ether and dried. Yield: 3.18 g. ESI mass spectrum: [($^{79}$Br)-M+H]$^+$=550, [($^{81}$Br)-M+H]$^+$=552; Retention time HPLC: 0.73 min (method X012_S01).

Intermediate 2

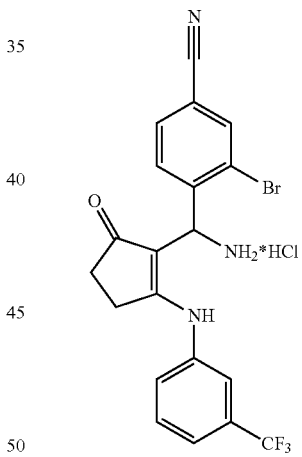

4-(Amino(5-oxo-2-(3-(trifluoromethyl)phenylamino)cyclopent-1-enyl)methyl)-3-bromobenzonitrile hydrochloride A solution of hydrogen chloride in 1,4-dioxane (4 M, 15.2 mL, 61 mmol) is added to a mixture of tert-butyl (2-bromo-4-cyanophenyl)(5-oxo-2-(3-(trifluoromethyl)phenylamino)-cyclopent-1-enyl)methylcarbamate (intermediate 1, 6.71 g, 12.2 mmol) in 1,4-dioxane (30 mL). The reaction mixture is stirred at room temperature for 2 h and then cooled in an ice bath. The precipitate is filtered, washed with cold acetonitrile and diethyl ether and dried. Yield: 5.90 g. ESI mass spectrum: [($^{79}$Br)-M+H]$^+$=450, [($^{81}$Br)-M+H]$^+$=452; Retention time HPLC: 1.17 min (method V011_S01).

Intermediate 3

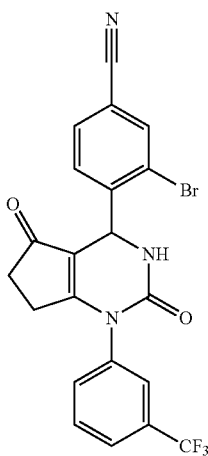 [SMILES: N#Cc1ccc(C2NC(=O)N(c3cccc(C(F)(F)F)c3)C3=C2C(=O)CC3)c(Br)c1]

3-Bromo-4-(2,5-dioxo-1-(3-(trifluoromethyl)phenyl)-2,3,4,5,6,7-hexahydro-1H-cyclopenta[d]pyrimidin-4-yl)benzonitrile Triethylamine (4.11 mL, 29.3 mmol) is added to a mixture of 4-(amino(5-oxo-2-(3-(tri-fluoromethyl)phenylamino)cyclopent-1-enyl)methyl)-3-bromobenzonitrile hydrochloride (intermediate 2)(28.5 g, 58.6 mmol) and 1,1'-carbonyldiimidazole (11.9 g, 73.2 mmol) in acetonitrile (290 mL). The mixture is stirred at room temperature overnight. Water (1.5 L) is added and the precipitate is filtered, washed with water and dried. Yield: 24.5 g. ESI mass spectrum: [($^{79}$Br)-M+H]$^+$=476, [($^{81}$Br)-M+H]$^+$=478; Retention time HPLC: 1.11 min (method V011_S01).

Intermediate 4

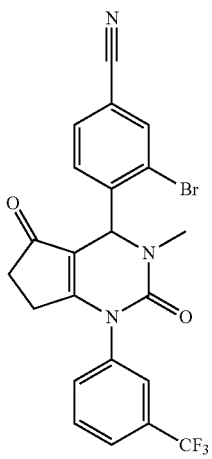 [SMILES: CN1C(=O)N(c2cccc(C(F)(F)F)c2)C2=C(C(=O)CC2)C1c1ccc(C#N)cc1Br]

3-Bromo-4-[3-methyl-2,5-dioxo-1-(3-trifluoromethyl-phenyl)-2,3,4,5,6,7-hexahydro-1H-cyclopentapyrimidin-4-yl]-benzonitrile Methyliodide (3.61 mL, 58.0 mmol) is added to a solution of 3-bromo-4-(2,5-dioxo-1-(3-(trifluoromethyl)phenyl)-2,3,4,5,6,7-hexahydro-1H-cyclopenta[d]pyrimidin-4-yl)benzonitrile (intermediate 3, 23.0 g, 48.3 mmol) and cesium carbonate (20.5 g, 62.8 mmol) in N,N-dimethylformamide (230 mL). The mixture is stirred at room temperature overnight. Water and ethyl acetate are added and the phases are separated. The organic phase is washed twice with water, dried over MgSO$_4$ and concentrated. Yield: 24.0 g. ESI mass spectrum: [($^{79}$Br)-M+H]$^+$=490, [($^{81}$Br)-M+H]$^+$=492; Retention time HPLC: 1.18 min (method V011_S01).

Intermediate 5

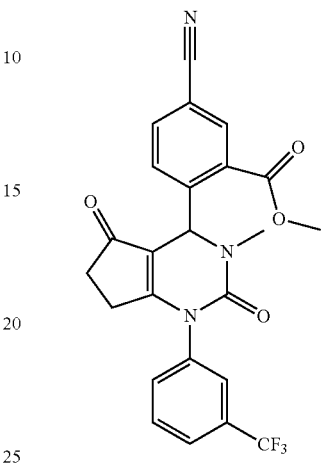

5-Cyano-2-[3-methyl-2,5-dioxo-1-(3-trifluoromethyl-phenyl)-2,3,4,5,6,7-hexahydro-1H-cyclopentapyrimidin-4-yl]-benzoic acid methyl ester 3-Bromo-4-[3-methyl-2,5-dioxo-1-(3-trifluoromethylphenyl)-2,3,4,5,6,7-hexahydro-1H-cyclopentapyrimidin-4-yl]-benzonitrile (intermediate 4)(11.85 g, 24.2 mmol), 1.1-bis(diphenylphosphino)-ferrocen (1.34 g, 2.42 mmol), palladium acetate (0.27 g, 1.21 mmol) and sodium acetate (5.95 g, 72.5 mmol) are suspended in methanol (400 mL) and are treated with carbon monoxide at 5 bar and 100° C. for 40 h. The reaction mixture is concentrated, water and ethyl acetate are added and the phases are separated. The organic phase is dried over MgSO$_4$ and concentrated. The residue is purified by flash chromatography on silica (cyclohexane/ethyl acetate 1:1). Yield: 8.0. g. ESI mass spectrum: [M+H]$^+$=470; Retention time HPLC: 1.15 min (method V011_S01).

Intermediate 6

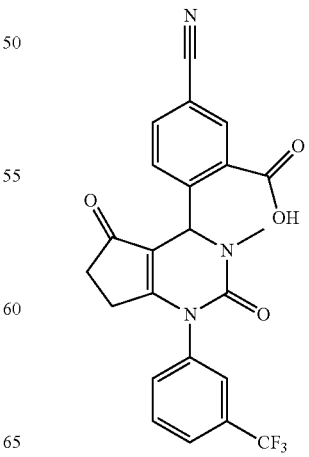

5-Cyano-2-[3-methyl-2,5-dioxo-1-(3-trifluoromethyl-phenyl)-2,3,4,5,6,7-hexahydro-1H-cyclopentapyrimidin-4-yl]-benzoic acid 5-Cyano-2-[3-methyl-2,5-dioxo-1-(3-trifluoromethyl-phenyl)-2,3,4,5,6,7-hexahydro-1H-cyclopentapyrimidin-4-yl]-benzoic acid methyl ester (intermediate 5)(6.70 g, 14.3 mmol) and lithium hydroxide (1.03 g, 42.8 mmol) are stirred in 1.4-dioxane (135 ml) and water (67.0 mL) at room temperature for 90 min. Water (250 mL) and hydrochloric acid (1.0 M, 44 mL) are added and the organic phase is extracted with ethyl acetate (400 mL). The organic phase is washed with water (3×250 mL), dried over $MgSO_4$ and concentrated. Yield: 6.2. g. ESI mass spectrum: $[M+H]^+$= 456; Retention time HPLC: 0.63 min (method X012_S01).

Intermediate 7

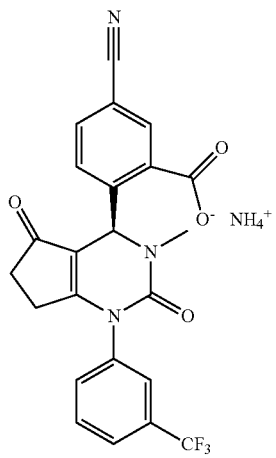 [SMILES: CN1C(=O)N(c2cccc(C(F)(F)F)c2)C2=C(C(=O)CC2)[C@H]1c1ccc(C#N)cc1C(=O)[O-] ; [NH4+]]

Ammonium 5-cyano-2-[(R)-3-methyl-2,5-dioxo-1-(3-trifluoromethyl-phenyl)-2,3,4,5,6,7-hexahydro-1H-cyclopentapyrimidin-4-yl]-benzoate 5-Cyano-2-[3-methyl-2,5-dioxo-1-(3-trifluoromethyl-phenyl)-2,3,4,5,6,7-hexahydro-1H-cyclopentapyrimidin-4-yl]-benzoic acid methyl ester (intermediate 5)(3.50 g, 7.46 mmol) and lithium hydroxide (0.54 g, 22.4 mmol) are stirred in 1.4-dioxane (70.0 ml) and water (35.0 mL) at room temperature for 90 min. The reaction mixture is acidified with hydrochloric acid (1.0 M, 24 mL) and diluted with water (350 mL). The precipitate is filtered and washed with water. The residue is stirred in tert-butyl methyl ether, filtered and washed with tert-butyl methyl ether.

The enantiomers are separated by preparative supercritical fluid chromatography on a chiral phase (Daicel Chiralpak AD-H, 4.6×250 mm, 5 μm, 25% MeOH+0.2% ammonia in supercritical $CO_2$, 40° C., 150 bar back pressure). Yield: 1.87 g; ESI mass spectrum $[M+H]^+$=456; Retention time: 2.258 min (early eluting R-enantiomer) (method I_IC_25_MEOH_NH$_3$). The configuration of intermediate 7 is assigned based on the X-ray structure of derivatives (e.g. example 2) in complex with neutrophil elastase.

Intermediate 8

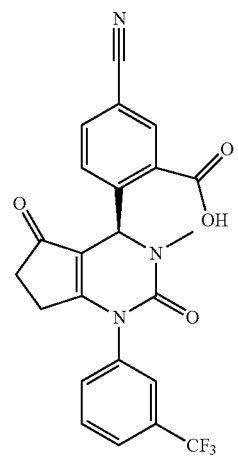 [SMILES: CN1C(=O)N(c2cccc(C(F)(F)F)c2)C2=C(C(=O)CC2)[C@H]1c1ccc(C#N)cc1C(=O)O]

5-Cyano-2-[(R)-3-methyl-2,5-dioxo-1-(3-trifluoromethyl-phenyl)-2,3,4,5,6,7-hexahydro-1H-cyclopentapyrimidin-4-yl]-benzoate Ammonium 5-cyano-2-[(R)-3-methyl-2,5-dioxo-1-(3-trifluoromethyl-phenyl)-2,3,4,5,6,7-hexahydro-1H-cyclopentapyrimidin-4-yl]-benzoate (intermediate 7)(1.15 g, 2.44 mmol) is stirred with water (35.0 mL) and hydrochloride acid (1 M, 5.0 mL) in an ultrasonic bath. The precipitate is filtered, washed with water and dried. Yield: 1.03 g. ESI mass spectrum: $[M+H]^+$=456; Retention time HPLC: 0733 min (method V011_S01); 2.493 min (method I_IC_30_MEOH_NH$_3$).

The configuration of intermediate 8 is assigned based on the X-ray structure of derivatives (e.g. example 2) in complex with neutrophil elastase.

Intermediate 11

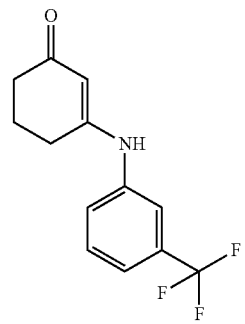 [SMILES: O=C1C=C(Nc2cccc(C(F)(F)F)c2)CCC1]

3-(3-Trifluoromethyl-phenylamino)-cyclohex-2-enone

3-Trifluoromethylanilin (5.5 mL, 44.6 mmol), 1,3-cyclohexanedione (5.0 g, 44.6 mmol) and ytterbium(III)trifluoromethanesulfonate (138 mg, 0.22 mmol) are suspended in tetrahydrofurane. The mixture is stirred for 2 h at room temperature and the precipitate is filtered. The product is purified by recrystallization from diisopropylether. Yield: 9.8 g; ESI mass spectrum: $[M+H]^+$=256, Retention time HPLC: 0.5 min (method X012_S02)

Intermediate 12

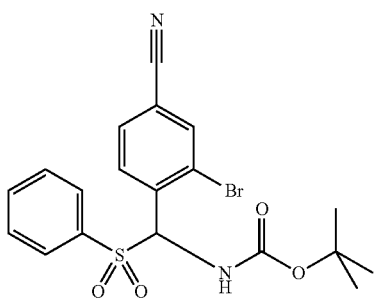 [SMILES: CC(C)(C)OC(=O)NC(c1ccc(C#N)cc1Br)S(=O)(=O)c1ccccc1]

[Benzenesulfonyl-(2-bromo-4-cyano-phenyl)-methyl]-carbamic acid tert-butyl ester 3-Bromo-4-formyl-benzonitrile (intermediate 10) (20.5 g, 97.7 mmol), benzenesulfinic acid sodium salt (16.03 g, 97.6 mmol) and tert-butylcarbamate (11.4 g, 97.7 mmol) are suspended in water (312 mL) and tetrahydrofurane (78 mL). Formic acid (28.8 g, 625 mmol) is added and the solution is stirred at room temperature for 6 days. Water (300 mL) is added and the precipitate is filtered, washed with water and dried. The crude product is further purified by addition of tert-butylmethylether and crystallization. Yield: 26.8 g; ESI mass spectrum: [M+Na]$^+$=473.

Intermediate 13

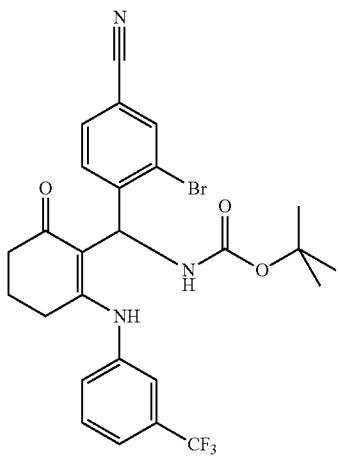 [SMILES: CC(C)(C)OC(=O)NC(C1=C(Nc2cccc(C(F)(F)F)c2)CCCC1=O)c1ccc(C#N)cc1Br]

{(2-Bromo-4-cyano-phenyl)-[6-oxo-2-(3-trifluoromethyl-phenylamino)-cyclohex-1-enyl]-methyl}-carbamic acid tert-butyl ester 3-(3-Trifluoromethyl-phenylamino)-cyclohex-2-enone (intermediate 11)(10.7 g, 42 mmol) is suspended in 2-methyl-tetrahydrofurane (150 mL) and sodium hydride (60% in mineral oil) (1.76 g, 43.9 mmol) is added in portions. The mixture is stirred at room temperature for 20 min and [benzenesulfonyl-(2-bromo-4-cyano-phenyl)-methyl]-carbamic acid tert-butyl ester (intermediate 12) (16.5 g, 36.6 mmol) is added. The mixture is stirred for 1 h at room temperature. The organic phase is extracted with water twice, dried over MgSO$_4$ and concentrated. The product is crystallized from cyclohexane. Yield: 20.6 g. ESI mass spectrum: [M+H]$^+$=564; Retention time HPLC: 0.81 min (method X012_S02).

Intermediate 14

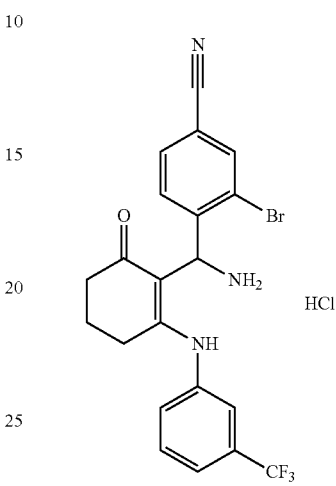

4-{Amino-[6-oxo-2-(3-trifluoromethyl-phenylamino)-cyclohex-1-enyl]-methyl}-3-bromo-benzonitrile hydrochloride {(2-Bromo-4-cyano-phenyl)-[6-oxo-2-(3-trifluoromethyl-phenylamino)-cyclohex-1-enyl]-methyl}-carbamic acid tert-butyl ester (intermediate 13)(20.8 g, 36.9 mmol) is suspended in acetonitrile (150 mL) and a solution of hydrogen chloride in 1,4-dioxane (4 M, 46.1 mL, 184.3 mmol) is added. The mixture is stirred at room temperature for 3 h. The product precipitates from the reaction mixture. The precipitate is filtered, washed with acetonitrile and dried. Yield: 16.5 g ESI mass spectrum: [M+H]$^+$=462, Retention time HPLC: 0.56 min, (method X012_S02).

Intermediate 15

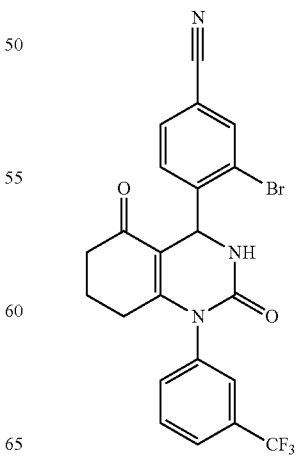

3-Bromo-4-[2,5-dioxo-1-(3-trifluoromethyl-phenyl)-1,2,3,4,5,6,7,8-octahydro-quinazolin-4-yl]-benzonitrile 4-{Amino-[6-oxo-2-(3-trifluoromethyl-phenylamino)-cyclohex-1-enyl]-methyl}-3-bromo-benzonitrile (intermediate 14)(16.5 g, 33 mmol) is suspended in acetonitrile (150 mL) and triethylamine (3.47 mL, 24.7 mmol) and 1,1'-carbonyldiimidazole (6.7 g, 41.2 mmol) are added. The mixture is stirred at room temperature for 1 h. The solvent is evaporated under reduced pressure and water is added. The product precipitates; the precipitate is filtered, washed with water and dried. Yield: 14 g. ESI mass spectrum: [M+H]$^+$=490; Retention time HPLC: 0.64 min (method X012_S02).

Intermediate 16

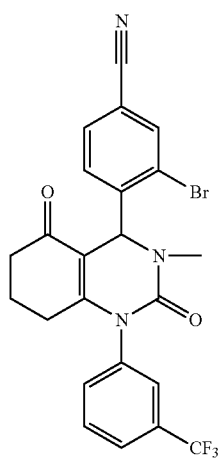 [SMILES: CN1C(=O)N(c2cccc(C(F)(F)F)c2)C2=C(C(=O)CCC2)C1c1ccc(C#N)cc1Br]

3-Bromo-4-[3-methyl-2,5-dioxo-1-(3-trifluoromethyl-phenyl)-1,2,3,4,5,6,7,8-octahydro-quinazolin-4-yl]-benzonitrile Methyliodide (3.55 mL, 57.1 mmol) is added to a solution of 3-Bromo-4-[2,5-dioxo-1-(3-trifluoromethyl-phenyl)-1,2,3,4,5,6,7,8-octahydro-quinazolin-4-yl]-benzonitrile (intermediate 15)(14.0 g, 28.6 mmol) and cesium carbonate (18.6 g, 57.1 mmol) in N,N-dimethylformamide (140 mL). The mixture is stirred at room temperature for 90 min. Ethyl acetate is added and the organic phase is extracted with water three times, dried over MgSO$_4$ and concentrated. The crude product is purified by flash chromatography on silica (cyclohexane/ethyl acetate 30:70). Yield: 13.4 g. ESI mass spectrum: [M+H]$^+$=504; Retention time HPLC: 0.70 min (method X012_S02).

Intermediate 17

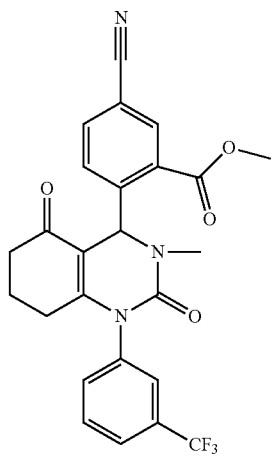 [SMILES: COC(=O)c1cc(C#N)ccc1C1C2=C(CCCC2=O)N(c2cccc(C(F)(F)F)c2)C(=O)N1C]

5-Cyano-2-[3-methyl-2,5-dioxo-1-(3-trifluoromethyl-phenyl)-1,2,3,4,5,6,7,8-octahydro-quinazolin-4-yl]-benzoic acid methyl ester 3-Bromo-4-[3-methyl-2,5-dioxo-1-(3-trifluoromethyl-phenyl)-1,2,3,4,5,6,7,8-octahydro-quinazolin-4-yl]-benzonitrile (intermediate 16)(10.5 g, 20.8 mmol), 1.1-bis(diphenylphosphino)-ferrocen (1.15 g, 2.08 mmol), palladium acetate (233 mg, 1.04 mmol) and sodium acetate (5.12 g, 62.5 mmol) are suspended in methanol (180 mL) and treated with carbon monoxide at 5 bar and 100° C. for 40 h. The product begins to crystallize from the reaction mixture. Diisopropylether and dichloromethane are added and further crystals are collected. Further purification is performed by recrystallization from methanol and by flash chromatography on silica (dichloromethane/methanol 99:1). Yield: 1.7 g. ESI mass spectrum: [M+H]$^+$=484; Retention time HPLC: 0.68 min (method X012_S02).

Intermediate 18

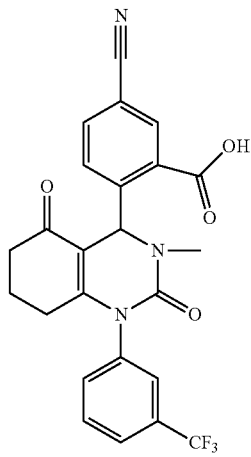 [SMILES: CN1C(=O)N(c2cccc(C(F)(F)F)c2)C2=C(C(=O)CCC2)C1c1ccc(C#N)cc1C(=O)O]

5-Cyano-2-[3-methyl-2,5-dioxo-1-(3-trifluoromethyl-phenyl)-1,2,3,4,5,6,7,8-octahydro-quinazolin-4-yl]-benzoic acid 5-Cyano-2-[3-methyl-2,5-dioxo-1-(3-trifluoromethyl-phenyl)-1,2,3,4,5,6,7,8-octahydro-quinazolin-4-yl]-benzoic acid methyl ester (intermediate 17)(5.3 g, 11 mmol) and lithium hydroxide (0.78 g, 32.9 mmol) are stirred in 1.4-dioxane (90 ml) and water (30.0 mL) at room temperature for 7.5 h. The reaction mixture is diluted with water and the aqueous phase is extracted with diethyl ether twice. The aqueous phase is acidified with hydrochloric acid to a pH of 2 and extracted with ethyl acetate. The ethyl acetate phase is a) evaporated under reduced pressure and the crude product is purified by reversed phase HPLC. Yield: 1.5 g; ESI mass spectrum [M+H]$^+$=470; Retention time HPLC: 0.61 min (method X012_S02).

Intermediate 19

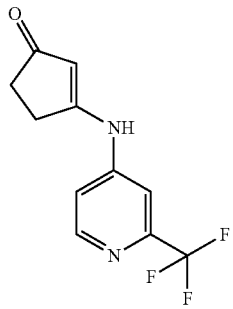 [SMILES: O=C1C=C(Nc2ccnc(C(F)(F)F)c2)CC1]

3-(2-Trifluoromethyl-pyridin-4-ylamino)-cyclopent-2-enone 1,3-cyclopentanedione (3.3 g, 33.9 mmol) and 4-amino-2-trifluoromethylpyridine (5.0 g, 30.8 mmol) are suspended in acetic acid (15 mL) and shaken at 130 C under microwave irradiation overnight. The reaction mixture is diluted with water and purified by reversed phase HPLC. Yield: 4.17 g; ESI mass spectrum [M+H]$^+$=243; Retention time HPLC: 0.77 min (method Z018_S04).

Intermediate 20

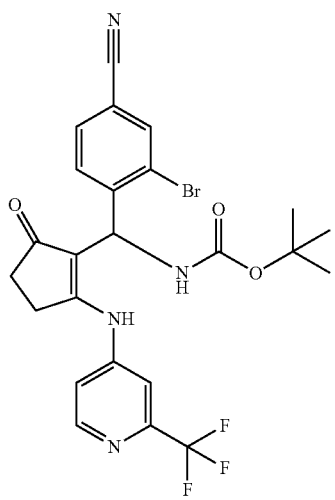 [SMILES: CC(C)(C)OC(=O)NC(C1=C(Nc2ccnc(C(F)(F)F)c2)CCC1=O)c1ccc(C#N)cc1Br]

{(2-Bromo-4-cyano-phenyl)-[5-oxo-2-(2-trifluoromethyl-pyridin-4-ylamino)-cyclopent-1-enyl]-methyl}-carbamic acid tert-butyl ester 3-(2-Trifluoromethyl-pyridin-4-ylamino)-cyclopent-2-enone (intermediate 19)(2.68 g, 11.08 mmol) is suspended in 2-methyl-tetrahydrofurane (80 mL) and sodium hydride (60% in mineral oil) (532 mg, 13.3 mmol) is added. The mixture is stirred at room temperature for 10 min and [benzenesulfonyl-(2-bromo-4-cyano-phenyl)-methyl]-carbamic acid tert-butyl ester (intermediate 12)(5.0 g, 11.08 mmol) is added. The mixture is stirred for 30 min at room temperature. Ethyl acetate (150 mL) is added and the organic phase is extracted with water three times, dried over MgSO$_4$ and concentrated. Yield: 5.7 g. ESI mass spectrum: [M+H]$^+$=551/553; Retention time HPLC: 1.09 min (method X012_S02).

Intermediate 21

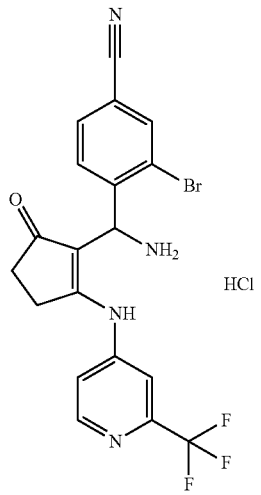 [SMILES: N#Cc1ccc(C(N)C2=C(Nc3ccnc(C(F)(F)F)c3)CCC2=O)c(Br)c1 ; Cl]

4-{Amino-[5-oxo-2-(2-trifluoromethyl-pyridin-4-ylamino)-cyclopent-1-enyl]-methyl}-3-bromo-benzonitrile hydrochloride {(2-Bromo-4-cyano-phenyl)-[5-oxo-2-(2-trifluoromethyl-pyridin-4-ylamino)-cyclopent-1-enyl]-methyl}-carbamic acid tert-butyl ester (intermediate 20) (2.4 g, 4.4 mmol) is suspended in dioxane (40 mL) and hydrochloric acid in dioxane (4 mol/l, 23.1 mL, 92.3 mmol) is added. The reaction mixture is stirred at room temperature for 90 min. The solvent is evaporated under reduced pressure. The product is used without further purification. Yield: 2.12 g; ESI mass spectrum [M-NH$_3$+H]$^+$=435; Retention time HPLC 0.8 min method (Z018_S04).

Intermediate 22

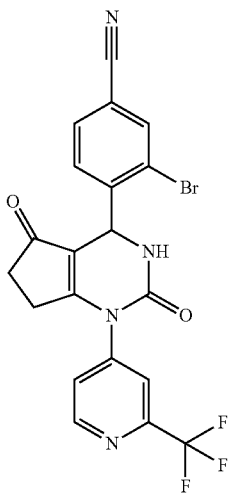 [SMILES: N#Cc1ccc(C2NC(=O)N(c3ccnc(C(F)(F)F)c3)C3=C2C(=O)CC3)c(Br)c1]

3-Bromo-4-[2,5-dioxo-1-(2-trifluoromethyl-pyridin-4-yl)-2,3,4,5,6,7-hexahydro-1H-cyclopentapyrimidin-4-yl]-benzonitrile 4-{Amino-[5-oxo-2-(2-trifluoromethyl-pyridin-4-ylamino)-cyclopent-1-enyl]-methyl}-3-bromo-benzonitrile hydrochloride (intermediate 21)(2.12 g, 4.4 mmol) is suspended in acetonitrile (70 mL) and 1,1'-carbonyldiimidazole (0.88 g, 5.4 mmol) and triethylamine (153 μL, 1.1 mmol) are added. The suspension is stirred at room temperature for 90 min and another portion of 1,1'-carbonyldiimidazole (0.88 g, 5.4 mmol) and triethylamine (153 μL, 1.1 mmol) are added. The stirring is continued and after 150 min another portion of 1,1'-carbonyldiimidazole (0.88 g, 5.4 mmol) and triethylamine (153 μL, 1.1 mmol) are added. The solvent is removed under reduced pressure and the residue is treated with water. The product crystallizes. The crystals are collected, washed with water and dried. Yield: 1.9 g; ESI mass spectrum [M+H]$^+$=478; Retention time HPLC: 0.94 min (method Z018_S04).

Intermediate 23

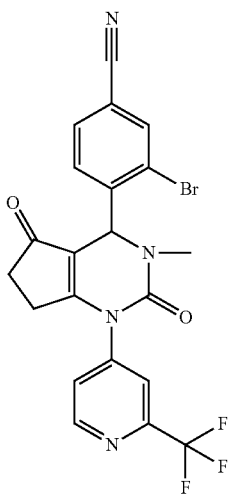 [SMILES: CN1C(=O)N(c2ccnc(C(F)(F)F)c2)C2=C(C(=O)CC2)C1c1ccc(C#N)cc1Br]

3-Bromo-4-[3-methyl-2,5-dioxo-1-(2-trifluoromethyl-pyridin-4-yl)-2,3,4,5,6,7-hexahydro-1H-cyclopentapyrimidin-4-yl]-benzonitrile 3-Bromo-4-[2,5-dioxo-1-(2-trifluoromethyl-pyridin-4-yl)-2,3,4,5,6,7-hexahydro-1H-cyclopentapyrimidin-4-yl]-benzonitrile (intermediate 22) (1.9 g, 3.98 mmol) and cesium carbonate (2.54 g, 7.96 mmol) are suspended in N,N-dimethylformamide (25 mL). A solution of methyl iodide dissolved in methyl-tert.butyl ether (2.4 mL, 4.8 mmol) is added and the mixture is shaken for 2 h at room temperature. Ice-water is added and the mixture is acidified with 50% aqueous trifluoroacetic acid. The product crystallizes. The crystals are collected, washed with water and dried. Yield: 1.46 g; ESI mass spectrum [M+H]$^+$=491; Retention time HPLC: 1.0 min (method Z018_S04).

Intermediate 24

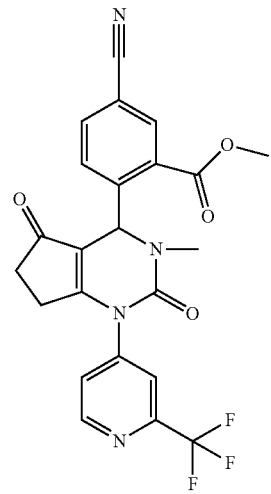 [SMILES: COC(=O)c1cc(C#N)ccc1C1C2=C(CCC2=O)N(c2ccnc(C(F)(F)F)c2)C(=O)N1C]

5-Cyano-2-[3-methyl-2,5-dioxo-1-(2-trifluoromethyl-pyridin-4-yl)-2,3,4,5,6,7-hexahydro-1H-cyclopentapyrimidin-4-yl]-benzoic acid methyl ester 3-Bromo-4-[3-methyl-2,5-dioxo-1-(2-trifluoromethyl-pyridin-4-yl)-2,3,4,5,6,7-hexahydro-1H-cyclopentapyrimidin-4-yl]-benzonitrile (intermediate 23)(1.46 g, 2.97 mmol), [1,1'-bis(diphenylphospino)ferrocene]dichloropalladium (II), complex with dichloromethane (1:1)(72.8 mg, 0.089 mmol) and sodium acetate (0.73 g, 8.92 mmol) are suspended in methanol (50 mL) and treated with carbon monoxide at 8 bar for 4 h at 100° C. The solvent is evaporated and ethylacetate is added. The organic phase is extracted with water three times, dried over MgSO$_4$ and evaporated. The product is purified by reversed phase HPLC. Yield: 595 mg; ESI mass spectrum [M+H]$^+$=471; Retention time HPLC: 0.99 min (method Z018_S04).

Intermediate 25

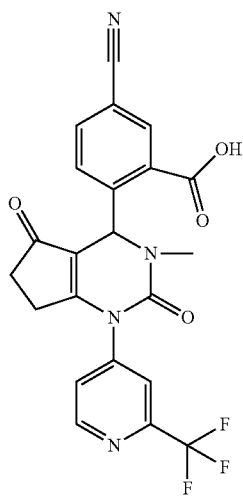 [SMILES: CN1C(=O)N(c2ccnc(C(F)(F)F)c2)C2=C(C(=O)CC2)C1c1ccc(C#N)cc1C(=O)O]

5-Cyano-2-[3-methyl-2,5-dioxo-1-(2-trifluoromethyl-pyridin-4-yl)-2,3,4,5,6,7-hexahydro-1H-cyclopentapyrimidin-4-yl]-benzoic acid 5-Cyano-2-[3-methyl-2,5-dioxo-1-(2-trifluoromethyl-pyridin-4-yl)-2,3,4,5,6,7-hexahydro-1H-cyclopentapyrimidin-4-yl]-benzoic acid methyl ester (intermediate 24)(880 mg, 1.62 mmol) is suspended in dioxane (10 mL) and water (5 mL). Lithiumhydroxide (58.3 mg, 2.43 mmol) is added and the reaction mixture is stirred at room temperature for 30 min. The mixture is acidified and purified by reversed phase HPLC. Yield: 158 mg; ESI mass spectrum [M+H]$^+$=457; Retention time HPLC: 0.91 min (method Z018_S04).

Intermediate 26

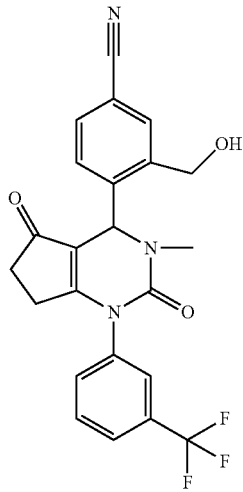 [SMILES: CN1C(=O)N(c2cccc(C(F)(F)F)c2)C2=C(C(=O)CC2)C1c1ccc(C#N)cc1CO]

3-Hydroxymethyl-4-[3-methyl-2,5-dioxo-1-(3-trifluoromethyl-phenyl)-2,3,4,5,6,7-hexahydro-1H-cyclopentapyrimidin-4-yl]-benzonitrile 5-Cyano-2-[3-methyl-2,5-dioxo-1-(3-trifluoromethyl-phenyl)-2,3,4,5,6,7-hexahydro-1H-cyclopentapyrimidin-4-yl]-benzoic acid (intermediate 6)(3.2 g, 7.03 mmol) is suspended in tetrahydrofurane (47 mL) and 1,1'-carbonyldiimidazole (1.25 g, 7.73 mmol) is added. The mixture is stirred for 90 min at room temperature. The reaction mixture is cooled to 5° C. and a solution of sodiumborohydride (399 mg, 10.54 mmol) in water (6.3 mL) is added drop wise. The mixture is stirred for 60 min and then acidified with 1N hydrochloric acid. The reaction mixture is extracted with ethylacetate and the organic phase is dried and evaporated under reduced pressure. Purification is performed by medium pressure chromatography on silica gel using dichloromethane/methanol 95:5→85:15 as eluent. Yield: 2.05 g; ESI mass spectrum [M+H]$^+$=442.6; Retention time HPLC: 0.61 min (method X012_S02).

Intermediate 27

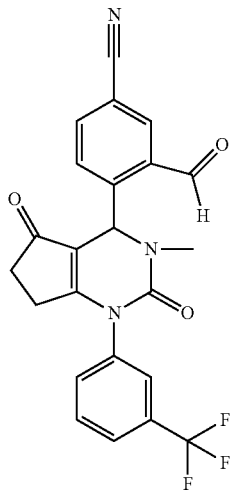 [SMILES: CN1C(=O)N(c2cccc(C(F)(F)F)c2)C2=C(C(=O)CC2)C1c1ccc(C#N)cc1C=O]

3-Formyl-4-[3-methyl-2,5-dioxo-1-(3-trifluoromethyl-phenyl)-2,3,4,5,6,7-hexahydro-1H-cyclopentapyrimidin-4-yl]-benzonitrile 3-Hydroxymethyl-4-[3-methyl-2,5-dioxo-1-(3-trifluoromethyl-phenyl)-2,3,4,5,6,7-hexahydro-1H-cyclopentapyrimidin-4-yl]-benzonitrile (intermediate 26)(2.05 g, 4.64 mmol) is suspended in dichloromethane (100 mL) and Dess-Martin periodinane (2.36 g, 5.57 mmol) is added. The mixture is stirred for 90 min at room temperature. Sodium thiosulfate solution (10%, 50 mL) and saturated sodium hydrogencarbonate solution (50 mL) are added and the suspension is stirred vigorously for 5 min. The organic phase is separated, extracted with water twice, dried over MgSO$_4$ and evaporated under reduced pressure. Purification is performed by medium pressure chromatography on silica gel using dichloromethane/methanol 98:2 as eluent. Yield: 510 mg; ESI mass spectrum [M+H]$^+$=440.6; Retention time HPLC: 0.63 min (method X012_S02).

Intermediate 28

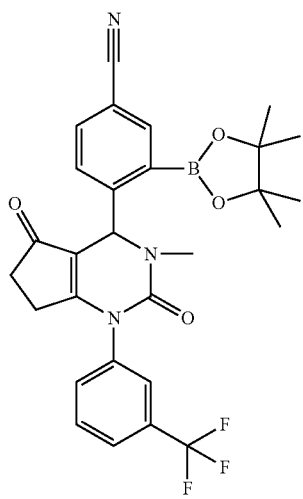

28a

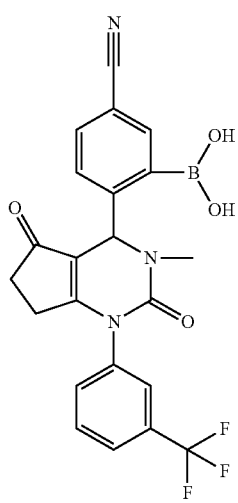

28b

4-[3-Methyl-2,5-dioxo-1-(3-trifluoromethyl-phenyl)-2,3,4,5,6,7-hexahydro-1H-cyclopentapyrimidin-4-yl]-3-(4,4,5,5-tetramethyl-[1,3,2]dioxaborolan-2-yl)-benzonitrile 28a and 4-[3-Methyl-2,5-dioxo-1-(3-trifluoromethyl-phenyl)-2,3,4,5,6,7-hexahydro-1H-cyclopentapyrimidin-4-yl]-3-boronsäure-benzonitrile 28b Under argon atmosphere 3-Bromo-4-[3-methyl-2,5-dioxo-1-(3-trifluoromethyl-phenyl)-2,3,4,5,6,7-hexahydro-1H-cyclopentapyrimidin-4-yl]-benzonitrile (intermediate 4)(2.5 g, 5.1 mmol) and bis(pinacolato)diboron (1.43 g, 5.62 mmol) are suspended in dimethylsulfoxide (50 mL). Potassium acetate (1 g, 10.2 mmol) and [1,1'-bis(diphenylphosphino)ferrocene]-dichloropalladium(II), complex with dichloromethane (1:1)(416 mg, 0.51 mmol) are added and the reaction mixture is stirred at 90° C. overnight. Ethylacetate is added and the organic phase is extracted with saturated NaCl-solution and water, dried and evaporated. The crude product is purified by reversed phase HPLC. Yield 300 mg of 28a; ESI mass spectrum [M+H]$^+$=538.8; Retention time HPLC: 0.8 min (X012_S02) and yield 600 mg of 28b; ESI mass spectrum [M+H]$^+$=456.7; Retention time HPLC: 0.59 min (method X012_S02)

Intermediate 29

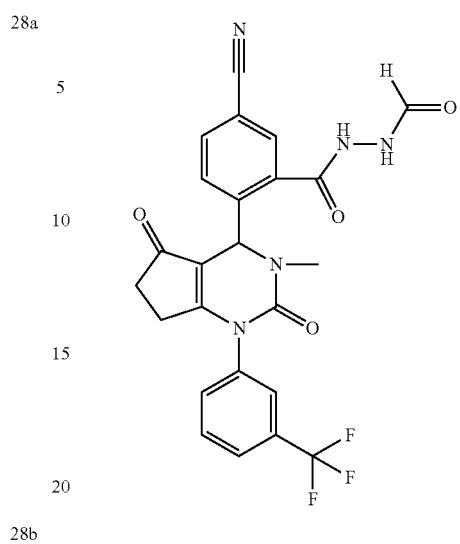

5-Cyano-2-[3-methyl-2,5-dioxo-1-(2-trifluoromethyl-pyridin-4-yl)-2,3,4,5,6,7-hexahydro-1H-cyclopentapyrimidin-4-yl]-benzoic acid formylhydrazide 5-Cyano-2-[3-methyl-2,5-dioxo-1-(3-trifluoromethyl-phenyl)-2,3,4,5,6,7-hexahydro-1H-cyclopentapyrimidin-4-yl]-benzoic acid (intermediate 6) (320 mg, 0.7 mmol) and triethylamine (244.9 μL, 1.71 mmol) are suspended in N,N-dimethylformamide (5 mL), stirred for 5 min and N,N,N',N'-tetramethyl-O-(benzotriazol-1-yl)uronium tetrafluoroborate (270.8 mg, 0.84 mmol) is added. The mixture is stirred for 10 min and formic acid hydrazide (84.4 mg, 1.41 mmol) is added. The mixture is stirred overnight at room temperature. After dilution with ethyl acetate the organic phase is extracted with water twice, dried and concentrated. The crude product is purified by reversed phase HPLC. Yield 170 mg; ESI mass spectrum [M+H]$^+$= 498.2; Retention time HPLC: 0.75 min (method V011_S01).

Intermediate 30

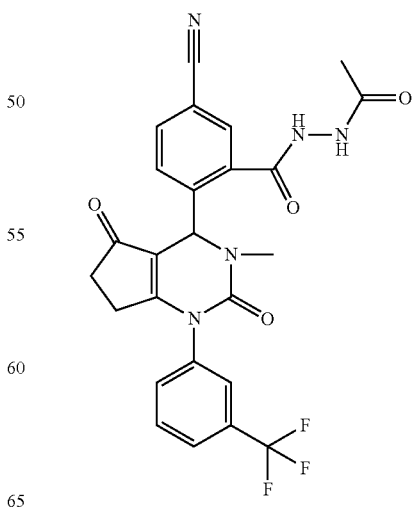

5-Cyano-2-[3-methyl-2,5-dioxo-1-(2-trifluoromethyl-pyridin-4-yl)-2,3,4,5,6,7-hexahydro-1H-cyclopentapyrimidin-4-yl]-benzoic acid acetylhydrazide 5-Cyano-2-[3-methyl-2,5-dioxo-1-(3-trifluoromethyl-phenyl)-2,3,4,5,6,7-hexahydro-1H-cyclopentapyrimidin-4-yl]-benzoic acid (intermediate 6) (80 mg, 0.18 mmol) and triethylamine (73.5 µL, 0.53 mmol) are suspended in N,N-dimethylformamide (1 mL), stirred for 5 min and O-(7-azabenzotriazole-1-yl)-N,N,N',N'-tetramethyluronium hexafluorophosphate (66.8 mg, 0.18 mmol) is added. The mixture is stirred for 10 min and ic) acetylhydrazide (20.8 mg, 0.28 mmol) is added. The mixture is stirred overnight at room temperature. Additional O-(7-azabenzotriazole-1-yl)-N,N,N',N'-tetramethyluronium hexafluorophosphate (66.8 mg, 0.18 mmol) and acetylhydrazide (20.8 mg, 0.28 mmol) are added and the reaction is continued for 2 h. The crude product is purified by reversed phase HPLC. Yield 27.4 mg; ESI mass spectrum [M+H]$^+$=456; Retention time HPLC: 0.97 min (method Z018_S04).

Intermediate 31

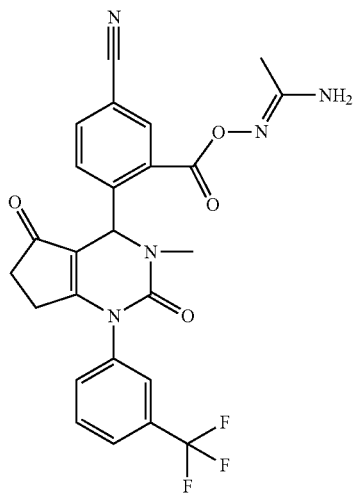 [SMILES: C/C(N)=N\OC(=O)c1cc(C#N)ccc1C1C2=C(CCC2=O)N(c2cccc(C(F)(F)F)c2)C(=O)N1C]

[1-Aminoethylideneamino]-5-Cyano-2-[3-methyl-2,5-dioxo-1-(3-trifluoromethyl-phenyl)-2,3,4,5,6,7-hexahydro-1H-cyclopentapyrimidin-4-yl]-benzoate 5-Cyano-2-[3-methyl-2,5-dioxo-1-(3-trifluoromethyl-phenyl)-2,3,4,5,6,7-hexahydro-1H-cyclopentapyrimidin-4-yl]-benzoic acid (intermediate 6)(80.0 mg, 0.17 mmol) and triethylamine (90 µL, 0.65 mmol) are suspended in N,N-dimethylformamide (1 mL), stirred for 10 min and O-(7-azabenzotriazole-1-yl)-N,N,N',N'-tetramethyluronium hexafluorophosphate (66 mg, 0.17 mmol) is added. The mixture is stirred for 10 min and N-hydroxyacetamidine (24.7 mg, 0.23 mmol) is added. The mixture is for 2 h at room temperature. The crude product is purified by reversed phase HPLC. Yield 50.2 mg; ESI mass spectrum [M+H]$^+$=456; Retention time HPLC: 0.97 min (method Z018_S04).

Intermediate 32

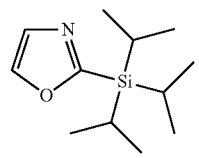

2-Triisopropylsilanyl-oxazole (see *Tetrahedron* 2009, 65, 6348-6353). Oxazole (10 g, 144.797 mmol) is dissolved in 400 mL abs. diethylether under argon. The solution is cooled to −78° C. and n-butyllithium (1.6 M solution in hexane, 100 mL, 160 mmol) is added slowly at that temperature. After stirring for 1 h triisopropylsilyl trifluoromethanesulfonate (40.265 mL, 144.797 mmol) in 100 mL abs. diethylether is added slowly. The mixture is warmed to r.t. within 12 h, and the solvent is evaporated in vacuo. The residue is treated with cyclohexane, filtered over silica gel, washed with cylcohexane/ethyl acetate 8:1, and the solvent is evaporated in vacuo. Yield: 33 g; ESI mass spectrum: [M+H]$^+$=226; retention time HPLC: 1.428 min (method Z001_002).

Intermediate 33

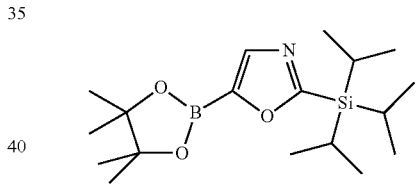

5-(4,4,5,5-Tetramethyl-[1,3,2]dioxaborolan-2-yl)-2-triisopropylsilanyl-oxazole (see *Tetrahedron* 2009, 65, 6348-6353)

2-Triisopropylsilanyl-oxazole (intermediate 16, 10 g, 44.365 mmol) is dissolved in 40 mL abs. diethylether under argon. The solution is cooled to −78° C. and n-butyllithium (1.6 M solution in hexane, 100 mL, 160 mmol) is added slowly at that temperature. After stirring for 1 h boronic acid triisopropylester (12 mL, 52.193 mmol) 20 mL abs. THF is added slowly. The mixture is stirred for 2 h, and is warmed to r.t. The mixture is quenched with methanol. 2,3-Dihydroxy-2,3-dimethylbutane (pinacole, 5.243 g, 44.365 mmol) is dissolved in 10 mL THF and injected to the mixture at 18° C. within 3 min. The mixture is acidified to pH 5 with acetic acid and stirred for 12 h. After addition of 150 mL diethylether and filtration over silica gel, the solvent is evaporated in vacuo. Yield: 15.2 g; ESI mass spectrum: [M+H]$^+$=352; retention time HPLC: 1.334 min (method Z001_002).

SYNTHESES OF EXAMPLES

Example 1

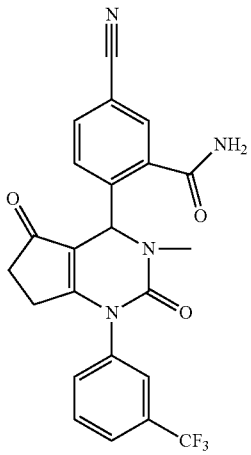 [SMILES: CN1C(=O)N(c2cccc(C(F)(F)F)c2)C2=C(C(=O)CC2)C1c1ccc(C#N)cc1C(N)=O]

5-Cyano-2-[3-methyl-2,5-dioxo-1-(3-trifluoromethyl-phenyl)-2,3,4,5,6,7-hexahydro-1H-cyclopentapyrimidin-4-yl]-benzamide To a solution of 5-cyano-2-[3-methyl-2,5-dioxo-1-(3-trifluoromethyl-phenyl)-2,3,4,5,6,7-hexahydro-1H-cyclopentapyrimidin-4-yl]-benzoic acid (intermediate 6)(200.0 mg, 0.44 mmol) in N,N-dimethylformamide (4.0 mL) N,N,N',N'-tetramethyl-O-(benzotriazol-1-yl)uronium tetrafluoroborate (148.1 mg, 0.46 mmol) and N,N-diisopropylethylamine (0.076 mL, 0.44 mmol) are added and the mixture stirred at room temperature for 15 min. Then ammonia chloride (117.5 mg, 2.20 mmol) and N,N-diisopropylethylamine (0.378 mL, 2.20 mmol) are added and the reaction mixture stirred at room temperature overnight. Water and ethyl acetate are added and the phases are separated. The organic phase is washed 3 times with water, dried over $MgSO_4$ and concentrated under reduced pressure. The reaction mixture is purified by reversed phase HPLC. Yield: 118 mg; ESI mass spectrum $[M+H]^+$=455; Retention time HPLC: 1.03 min (method V011_S01).

The following examples of Table 1 are prepared in analogy of 5-cyano-2-[3-methyl-2,5-dioxo-1-(3-trifluoromethyl-phenyl)-2,3,4,5,6,7-hexahydro-1H-cyclopentapyrimidin-4-yl]-benzamide (example 1), using the appropriate amine as starting material. Examples 1.2 and 1.4-1.35 are prepared using triethylamine as base. Examples 1.76-1.85 are prepared using O-(7-zabenzotriazole-1-yl)-N,N,N',N'-tetramethyluronium hexafluorophosphate as coupling reagent and triethylamine as base.

TABLE 1

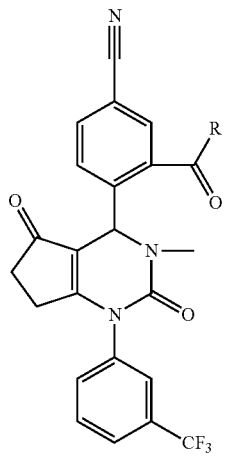

| Example | R | MS [M + H]⁺ | Retention time [min] | HPLC-Method |
|---|---|---|---|---|
| 1.1 | ----NH₂ | 469 | 1.07 | V011_S01 |
| 1.2 | ----NH-Et | 483 | 0.79 | 003_CA04 |
| 1.3 | ----N(CH₃)₂ | 483 | 1.07 | V011_S01 |
| 1.4 | ----NH-CH₂-C≡CH | 493 | 0.79 | 003_CA04 |
| 1.5 | ----NH-CH₂-C≡N | 494 | 0.75 | 003_CA04 |

TABLE 1-continued
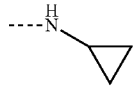
| Example | R | MS [M + H]⁺ | Retention time [min] | HPLC-Method |
|---|---|---|---|---|
| 1.6 | 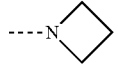 | 495 | 0.81 | 003_CA04 |
| 1.7 | 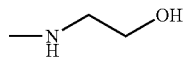 | 495 | 0.81 | 005_CA01 |
| 1.8 | 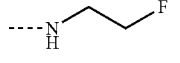 | 499 | 0.73 | 005_CA01 |
| 1.9 | 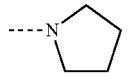 | 501 | 0.77 | 003_CA04 |
| 1.10 |  | 509 | 0.81 | 003_CA04 |
| 1.11 | 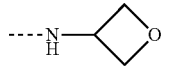 | 511 | 0.69 | 003_CA04 |
| 1.12 | 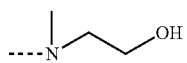 | 511 | 0.73 | 003_CA04 |
| 1.13 | 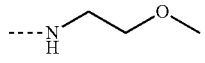 | 513 | 0.71 | 003_CA04 |
| 1.14 | 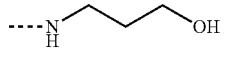 | 513 | 0.77 | 003_CA04 |
| 1.15 | 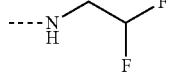 | 513 | 0.71 | 003_CA04 |
| 1.16 | 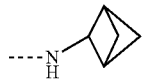 | 519 | 0.81 | 003_CA04 |
| 1.17 | 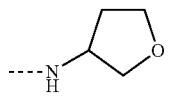 | 521 | 0.89 | 003_CA04 |
| 1.18 |  | 525 | 0.76 | 003_CA04 |

TABLE 1-continued

| Example | R | MS [M + H]+ | Retention time [min] | HPLC-Method |
|---|---|---|---|---|
| 1.19 | —NH-CH2-C(CH3)2-OH | 527 | 0.75 | 003_CA04 |
| 1.20 | —NH-CH2CH2CH2-OCH3 | 527 | 0.79 | 003_CA04 |
| 1.21 | —NH-CH2-CF3 (with extra F) | 537 | 0.86 | 003_CA04 |
| 1.22 | 4-hydroxypiperidin-1-yl | 539 | 0.69 | 003_CA04 |
| 1.23 | —NH-(tetrahydropyran-4-yl) | 539 | 0.77 | 003_CA04 |
| 1.24 | —N(CH3)-CH2CH2CH2-OCH3 | 541 | 0.80 | 003_CA04 |
| 1.25 | —NH-(1-methylpiperidin-4-yl) | 552 | 0.77 | 003_CA04 |
| 1.26 | —NH-CH2CH2-S(O)2-CH3 | 561 | 0.72 | 003_CA04 |
| 1.27 | —N(CH3)-CH2-(1-methylpyrazol-4-yl) | 563 | 0.76 | 003_CA04 |
| 1.28 | —NH-(1,1-dioxo-tetrahydrothiophen-3-yl) | 573 | 0.74 | 003_CA04 |
| 1.29 | —NH-CH2CH2-N(CH3)2 | 526 | 0.92 | 003_CA03 |

TABLE 1-continued

| Example | R | MS [M + H]+ | Retention time [min] | HPLC-Method |
|---------|---|-------------|----------------------|-------------|
| 1.30 | -NH-(1-methylpyrrolidin-3-yl) | 538 | 0.92 | 003_CA03 |
| 1.31 | -NH-(3-dimethylamino-cyclopentyl) | 552 | 0.92 | 003_CA03 |
| 1.32 | -NH-(3-dimethylamino-cyclopentyl) | 552 | 0.92 | 003_CA03 |
| 1.33 | -N(4-cyclopropylpiperazin-1-yl) | 564 | 0.94 | 003_CA03 |
| 1.34 | -NH-(1-isopropylpyrrolidin-3-yl) | 566 | 0.95 | 003_CA03 |
| 1.34 | -N(tetrahydro-[1,2,4]triazolo[4,3-a]pyrazin-7-yl) | 562 | 0.99 | 003_CA03 |
| 1.35 | -N(hexahydropyrazino[2,1-c][1,4]oxazin-8-yl) | 580 | 0.94 | 003_CA03 |
| 1.36 | -NH-CH2-(furan-2-yl) | 535 | 0.84 | 005_CA01 |
| 1.37 | -NH-CH2-(furan-3-yl) | 535 | 0.84 | 005_CA01 |
| 1.38 | -NH-CH2-(1H-pyrazol-4-yl) | 535 | 0.69 | 005_CA01 |

TABLE 1-continued

| Example | R | MS [M + H]+ | Retention time [min] | HPLC-Method |
|---|---|---|---|---|
| 1.39 | -NH-CH2-(isoxazol-5-yl) | 536 | 0.78 | 005_CA01 |
| 1.40 | -NH-CH2-(oxazol-5-yl) | 536 | 0.74 | 005_CA01 |
| 1.41 | -NH-CH2-(oxazol-2-yl) | 536 | 0.76 | 005_CA01 |
| 1.42 | -NH-CH2-(isoxazol-4-yl) | 536 | 0.78 | 005_CA01 |
| 1.43 | -NH-CH2-(isoxazol-3-yl) | 536 | 0.78 | 005_CA01 |
| 1.44 | -NH-CH2-(oxazol-4-yl) | 536 | 0.75 | 005_CA01 |
| 1.45 | -NH-CH2-phenyl | 545 | 0.90 | 005_CA01 |
| 1.46 | -NH-CH2-(pyridin-3-yl) | 546 | 0.61 | 005_CA01 |
| 1.47 | -NH-CH2-(pyridin-2-yl) | 546 | 0.62 | 005_CA01 |
| 1.48 | -NH-CH2-(pyridin-4-yl) | 546 | 0.61 | 005_CA01 |

TABLE 1-continued
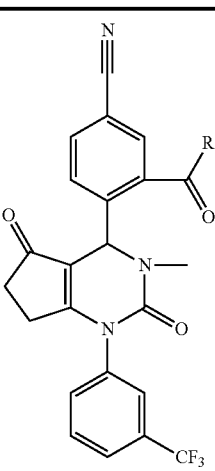
| Example | R | MS [M + H]+ | Retention time [min] | HPLC-Method |
|---|---|---|---|---|
| 1.49 | 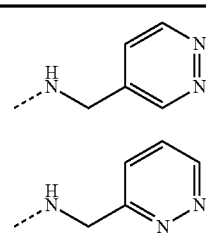 | 547 | 0.68 | 005_CA01 |
| 1.50 | 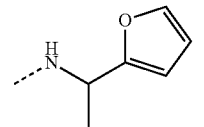 | 547 | 0.70 | 005_CA01 |
| 1.51 | 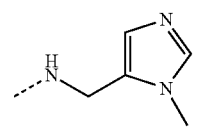 | 549 | 0.89 | 005_CA01 |
| 1.52 | 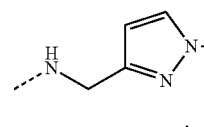 | 549 | 0.55 | 005_CA01 |
| 1.53 | 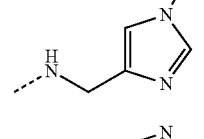 | 549 | 0.76 | 005_CA01 |
| 1.54 | 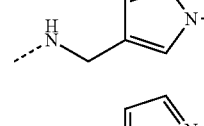 | 549 | 0.55 | 005_CA01 |
| 1.55 | 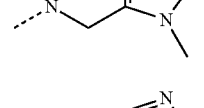 | 549 | 0.74 | 005_CA01 |
| 1.56 | 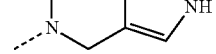 | 549 | 0.75 | 005_CA01 |
| 1.57 |  | 549 | 0.68 | 005_CA01 |

TABLE 1-continued

| Example | R | MS [M + H]+ | Retention time [min] | HPLC-Method |
|---|---|---|---|---|
| 1.58 | (N-methylimidazol-2-yl)methylamino | 549 | 0.55 | 005_CA01 |
| 1.59 | (isoxazol-3-yl)methyl-N-methylamino | 550 | 0.80 | 005_CA01 |
| 1.60 | (isoxazol-5-yl)methyl-N-methylamino | 550 | 0.79 | 005_CA01 |
| 1.61 | (4-methyl-1,2,4-triazol-3-yl)methylamino | 550 | 0.62 | 005_CA01 |
| 1.62 | (1-methyltetrazol-5-yl)methylamino | 551 | 0.74 | 005_CA01 |
| 1.63 | 2,3-dihydro-1H-pyrrolo[3,4-c]pyridin-2-yl | 558 | 0.57 | 005_CA01 |
| 1.64 | (5-cyanofuran-2-yl)methylamino | 560 | 0.85 | 005_CA01 |
| 1.65 | N-methyl-(pyridin-4-yl)methylamino | 560 | 0.57 | 005_CA01 |
| 1.66 | 5,6-dihydroimidazo[1,5-a]pyrazin-7(8H)-yl | 561 | 0.55 | 005_CA01 |

TABLE 1-continued
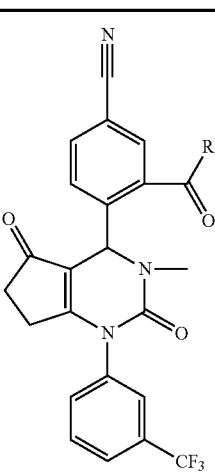
| Example | R | MS [M + H]⁺ | Retention time [min] | HPLC-Method |
|---|---|---|---|---|
| 1.67 | 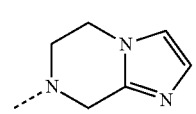 | 561 | 0.75 | 005_CA01 |
| 1.68 | 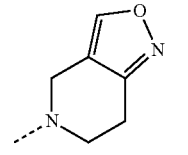 | 561 | 0.55 | 005_CA01 |
| 1.69 | 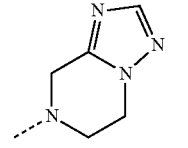 | 562 | 0.75 | 003_CA04 |
| 1.70 | 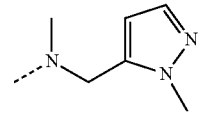 | 562 | 0.71 | 005_CA01 |
| 1.71 | 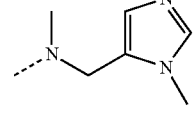 | 563 | 0.77 | 005_CA01 |
| 1.72 | 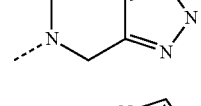 | 563 | 0.56 | 005_CA01 |
| 1.73 | 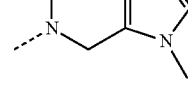 | 563 | 0.77 | 005_CA01 |
| 1.74 | | 563 | 0.57 | 005_CA01 |

TABLE 1-continued
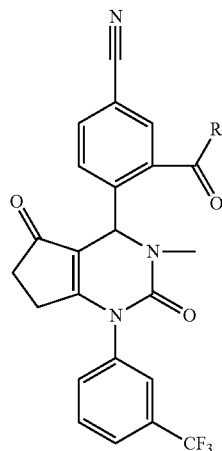
| Example | R | MS [M + H]+ | Retention time [min] | HPLC-Method |
|---|---|---|---|---|
| 1.75 | (dimethylaminomethyl-4-methyl-1,2,4-triazole) | 564 | 0.64 | 005_CA01 |
| 1.76 | (NH-CH2CH2-morpholine) | 568 | 0.94 | Z011_S03 |
| 1.77 | (pyrrolidinyl-N(Me)COCH3) | 580 | 0.92 | Z011_S03 |
| 1.78 | (pyrrolidinyl-N(Me)COCH3) | 580 | 0.71 | 004_CA05 |
| 1.79 | (pyrrolidinyl-morpholine) | 594 | 0.93 | Z011_S03 |
| 1.80 | (NH-CH2-CO-morpholine) | 582 | 0.91 | Z011_S03 |
| 1.81 | (N(Me)-CH2CH2-morpholine) | 582 | 0.94 | Z011_S03 |
| 1.82 | (piperazinyl-cyclopropyl) | 608 | 0.93 | Z011_S03 |

TABLE 1-continued

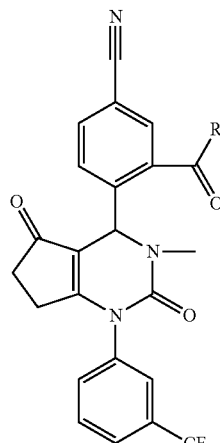

| Example | R | MS [M + H]⁺ | Retention time [min] | HPLC-Method |
|---|---|---|---|---|
| 1.83 | 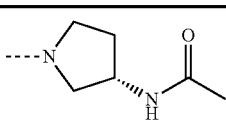 | 566 | 0.91 | Z011_S03 |
| 1.84 | 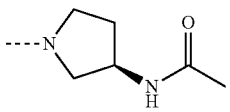 | 566 | 0.90 | Z011_S03 |
| 1.85 | 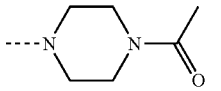 | 566 | 0.90 | Z011_S03 |

Example 2

5-Cyano-2-[(R)-3-methyl-2,5-dioxo-1-(3-trifluoromethyl-phenyl)-2,3,4,5,6,7-hexahydro-1H-cyclopentapyrimidin-4-yl]-benzamide

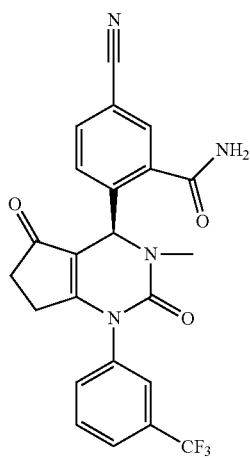 [SMILES: CN1C(=O)N(c2cccc(C(F)(F)F)c2)C2=C(C(=O)CC2)[C@H]1c1ccc(C#N)cc1C(N)=O]

To a solution 5-cyano-2-[(R)-3-methyl-2,5-dioxo-1-(3-trifluoromethyl-phenyl)-2,3,4,5,6,7-hexahydro-1H-cyclopentapyrimidin-4-yl]-benzoate (intermediate 8)(200.0 mg, 0.44 mmol) in N,N-dimethylformamide (4.0 mL) N,N,N',N'-tetramethyl-O-(benzotriazol-1-yl)uronium tetrafluoroborate (148.1 mg, 0.46 mmol) and N,N-diisopropylethylamine (0.076 mL, 0.44 mmol) are added and the mixture is stirred at room temperature for 15 min. Then ammonia chloride (117.5 mg, 2.20 mmol) and N,N-diisopropylethylamine (0.378 mL, 2.20 mmol) are added and the reaction mixture is stirred at room temperature overnight. Water and ethyl acetate are added and the phases are separated. The organic phase is washed 3 times with water, dried over MgSO₄ and concentrated. The reaction mixture is purified by reversed phase. Yield: 147 mg; ESI mass spectrum [M+H]⁺=455; Retention time HPLC: 1.02 min (method V011_S01).

The configuration of example 2 is assigned based on the X-ray structure of example 2 in complex with neutrophil elastase.

The following examples of Table 2 are prepared in analogy of 5-cyano-2-[(R)-3-methyl-2,5-dioxo-1-(3-trifluoromethyl-phenyl)-2,3,4,5,6,7-hexahydro-1H-cyclopentapyrimidin-4-yl]-benzamide (example 2), using the appropriate amine as starting material.

TABLE 2

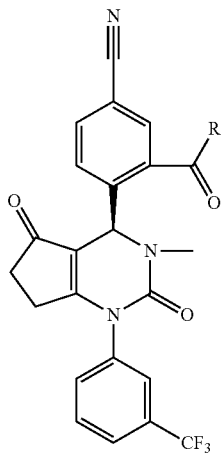

| Example | R | MS [M + H]+ | Retention time [min] | HPLC-Method |
|---|---|---|---|---|
| 2.1 | ----NH-CH3 | 469 | 1.06 | V011_S01 |
| 2.2 | ----N(CH3)2 | 483 | 1.06 | V011_S01 |
| 2.3 | ----N(morpholine) | 525 | 0.61 | X012_S02 |
| 2.4 | ----N(N-methylpiperazine) | 538 | 0.52 | X012_S02 |

Example 3

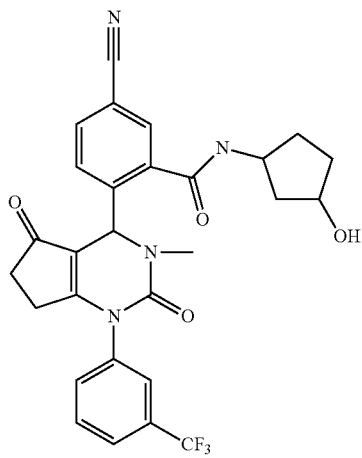 [SMILES: CN1C(=O)N(c2cccc(C(F)(F)F)c2)C2=C(C(=O)CC2)C1c1ccc(C#N)cc1C(=O)NC1CCC(O)C1]

5-Cyano-N-(3-hydroxy-cyclopentyl)-2-[3-methyl-2,5-dioxo-1-(3-trifluoromethyl-phenyl)-2,3,4,5,6,7-hexahydro-1H-cyclopentapyrimidin-4-yl]-benzamide To a solution of 5-cyano-2-[3-methyl-2,5-dioxo-1-(3-trifluoromethyl-phenyl)-2,3,4,5,6,7-hexahydro-1H-cyclopentapyrimidin-4-yl]-benzoic acid (intermediate 6)(50.0 mg, 0.08 mmol) in N,N-dimethylformamide (2.0 mL) triethylamine (32.1 μL, 0.23 mmol) is added and the reaction mixture is stirred at room temperature. After 5 min N,N,N',N'-tetramethyl-O-(benzotriazol-1-yl)uronium tetrafluoroborate (24.7 mg, 0.08 mmol) is added and the vi reaction is stirred at room temperature for 5 min. Then 3-aminocyclopentanole (10.6 mg, 0.08 mmol) is added and stirring is continued at room temperature overnight. The reaction mixture is purified by reversed phase. Yield: 26.9 mg; ESI mass spectrum [M+H]+=539; Retention time HPLC: 0.73 min (method 003_CA04).

The following examples of Table 3 are prepared in analogy of 5-cyano-N-(3-hydroxy-cyclopentyl)-2-[3-methyl-2,5-dioxo-1-(3-trifluoromethyl-phenyl)-2,3,4,5,6,7-hexahydro-1H-cyclopentapyrimidin-4-yl]-benzamide (example 3), using the appropriate amine as starting material.

TABLE 3

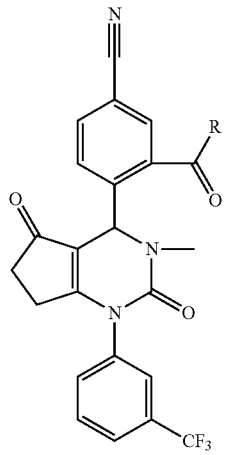

| Example | R | MS [M + H]+ | Retention time [min] | HPLC-Method |
|---|---|---|---|---|
| 3.1 | ----N(CH3)CH2CH2N(CH3)2 | 540 | 0.84 | Z018_S04 |
| 3.2 | ----N-piperazine-ethyl | 552 | 0.79 | 003_CA04 |
| 3.3 | ----N-octahydroindolizine | 564 | 0.84 | Z018_S04 |
| 3.4 | ----N-piperazine-isopropyl | 566 | 0.85 | Z018_S04 |
| 3.5 | ----N-bicyclic N+(CH3)2 I− | 564 | 0.83 | Z018_S04 |

Example 4

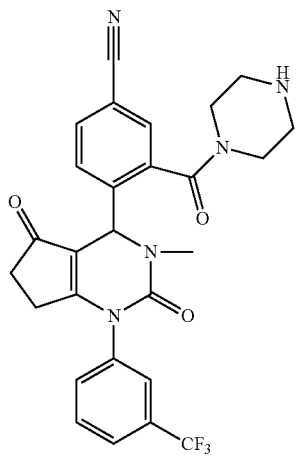

Step 1

4-{5-Cyano-2-[3-methyl-2,5-dioxo-1-(3-trifluoromethyl-phenyl)-2,3,4,5,6,7-hexahydro-1H-cyclopentapyrimidin-4-yl]-benzoylamino}-piperidine-1-carboxylic acid tert-butyl ester To a solution of 5-cyano-2-[3-methyl-2,5-dioxo-1-(3-trifluoromethyl-phenyl)-2,3,4,5,6,7-hexahydro-1H-cyclopentapyrimidin-4-yl]-benzoic acid (intermediate 6)(50.0 mg, 0.08 mmol) in N,N-dimethylformamide (2.0 mL) triethylamine (32.1 μL, 0.23 mmol) is added and the reaction is stirred at room temperature. After 5 min N,N,N',N'-tetramethyl-O-(benzotriazol-1-yl)uronium tetrafluoroborate (24.7 mg, 0.08 mmol) is added and the mixture is stirred at room temperature for 5 min. Then tert-butyl-1-piperazinecarboxylate (17.2 mg, 0.09 mmol) is added and stirring is continued at room temperature for 1 h. The reaction mixture is filtered through basic aluminium oxide, washed with N,N-dimethylformamide (1 mL) and concentrated in vacuo.

Step 2

5-Cyano-2-[3-methyl-2,5-dioxo-1-(3-trifluoromethyl-phenyl)-2,3,4,5,6,7-hexahydro-1H-cyclopentapyrimidin-4-yl]-N-piperidin-4-yl-benzamide To a solution of 4-{5-cyano-2-[3-methyl-2,5-dioxo-1-(3-trifluoromethyl-phenyl)-2,3,4,5,6,7-hexahydro-1H-cyclopentapyrimidin-4-yl]-benzoylamino}-piperidine-1-carboxylic acid tert-butyl ester (step 1) in dichloromethane (1 mL) trifluoroacetic acid (1.0 mL, 13.0 mmol) is added and the reaction is stirred at room temperature for 1 h. The reaction mixture is concentrated and purified by reversed phase. Yield: 39.0 mg; ESI mass spectrum [M+H]$^+$=524; Retention time HPLC: 0.60 min (method 005_CA01).

The following examples of Table 4 are prepared in analogy of 5-cyano-2-[3-methyl-2,5-dioxo-1-(3-trifluoromethyl-phenyl)-2,3,4,5,6,7-hexahydro-1H-cyclopentapyrimidin-4-yl]-N-piperidin-4-yl-benzamide (example 4), using the appropriate amine as starting material.

TABLE 4

| Example | R | MS [M + H]$^+$ | Retention time [min] | HPLC-Method |
|---|---|---|---|---|
| 4.1 | piperidin-4-yl-amine (N-linked piperidine with 4-NH$_2$) | 538 | 0.59 | 005_CA01 |
| 4.2 | N-(piperidin-4-yl)amino (NH-linked 4-piperidyl, ring NH) | 538 | 0.60 | 005_CA01 |
| 4.3 | NH-CH$_2$-CH$_2$-NH$_2$ | 498 | 0.91 | 003_CA03 |
| 4.4 | NH-CH$_2$-CH$_2$-NH-CH$_3$ | 512 | 0.92 | 003_CA03 |
| 4.5 | N(CH$_3$)-CH$_2$-CH$_2$-NH$_2$ | 512 | 0.92 | 003_CA03 |
| 4.6 | NH-(pyrrolidin-3-yl) (3-NH of pyrrolidine linked) | 524 | 0.92 | 003_CA03 |
| 4.7 | (R)-3-aminopyrrolidin-1-yl | 524 | 0.91 | 003_CA03 |
| 4.8 | (S)-3-aminopyrrolidin-1-yl | 524 | 0.91 | 003_CA03 |
| 4.9 | 3-aminopyrrolidin-1-yl (stereo) | 524 | 0.91 | 003_CA03 |
| 4.10 | N(CH$_3$)-CH$_2$-CH$_2$-NH-CH$_3$ | 526 | 0.93 | 003_CA03 |
| 4.11 | NH-CH$_2$-C(CH$_3$)$_2$-NH$_2$ | 526 | 0.93 | 003_CA03 |

TABLE 4-continued

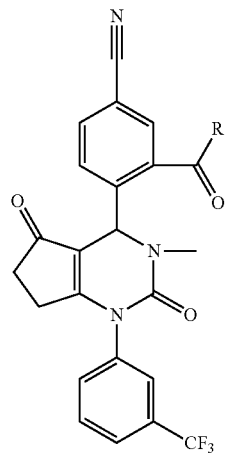

| Example | R | MS [M + H]⁺ | Retention time [min] | HPLC-Method |
|---|---|---|---|---|
| 4.12 | | 538 | 0.92 | 003_CA03 |
| 4.13 | | 510 | 0.91 | 003_CA03 |
| 4.14 | | 510 | 0.91 | 003_CA03 |
| 4.15 | | 536 | 0.59 | 005_CA01 |
| 4.16 | | 538 | 0.92 | 003_CA03 |
| 4.17 | | 566 | 0.58 | 005_CA01 |

Example 5

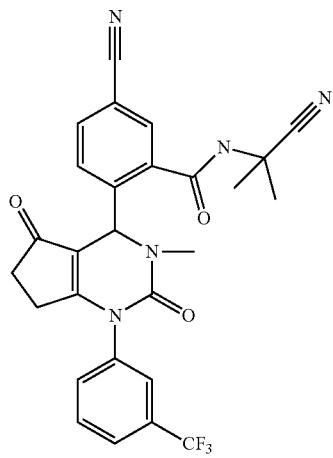 [SMILES: CN1C(=O)N(c2cccc(C(F)(F)F)c2)C2=C(C(=O)CC2)C1c1ccc(C#N)cc1C(=O)NC(C)(C)C#N]

Step 1

5-Cyano-2-[3-methyl-2,5-dioxo-1-(3-trifluoromethyl-phenyl)-2,3,4,5,6,7-hexahydro-1H-cyclopentapyrimidin-4-yl]-benzoyl chloride To a solution of 5-cyano-2-[3-methyl-2,5-dioxo-1-(3-trifluoromethyl-phenyl)-2,3,4,5,6,7-hexahydro-1H-cyclopentapyrimidin-4-yl]-benzoic acid (intermediate 6)(100.0 mg, 0.22 mmol) in acetonitrile (2.0 mL) 1-chloro-N,N,2-trimethylpropenylamine (38.0 µL, 0.29 mmol) is added and the mixture is stirred at room temperature for 2 h.

Step 2

5-Cyano-N-(cyano-dimethyl-methyl)-2-[3-methyl-2,5-dioxo-1-(3-trifluoromethyl-phenyl)-2,3,4,5,6,7-hexahydro-1H-cyclopentapyrimidin-4-yl]-benzamide To a solution of 2-amino-2-methylpropanenitrile (20.0 mg, 0.24 mmol) in acetonitrile (1.0 mL) triethylamine (37.0 µL, 0.27 mmol) and the reaction mixture of step 1 is added and the mixture stirred at room temperature overnight. The reaction mixture is purified by reversed phase. Yield: 7.0 mg; ESI mass spectrum [M+H]⁺=522; Retention time HPLC: 1.00 min (method Z018_S04).

Example 6

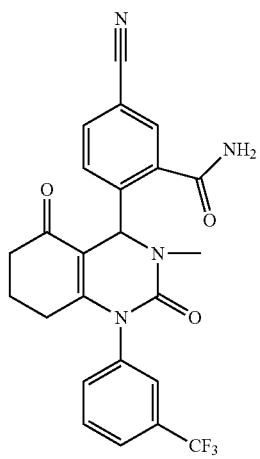

5-Cyano-2-[3-methyl-2,5-dioxo-1-(3-trifluoromethyl-phenyl)-1,2,3,4,5,6,7,8-octahydro-quinazolin-4-yl]-benzamide Example 7

To a solution of 5-Cyano-2-[3-methyl-2,5-dioxo-1-(3-trifluoromethyl-phenyl)-1,2,3,4,5,6,7,8-octahydro-quinazolin-4-yl]-benzoic acid (intermediate 18)(340 mg, 0.72 mmol) in N,N-dimethylformamide (3.0 mL) N,N,N',N'-tetramethyl-O-(benzotriazol-1-yl)uronium tetrafluoroborate (321 mg, 0.76 mmol) and N,N-diisopropylethylamine (0.131 mL, 0.76 mmol) are added and the mixture is stirred at room temperature for 15 min Ammonium chloride (194 mg, 3.62 mmol) and N,N-diisopropylethylamine (0.626 mL, 3.62 mmol) are added and stirring is continued at room temperature overnight. Water and ethyl acetate are added and the phases are separated. The organic phase is washed 3 times with water, dried over $MgSO_4$ and concentrated under reduced pressure. The reaction mixture is purified by reversed phase HPLC. Yield: 235 mg; ESI mass spectrum $[M+H]^+$=469; Retention time HPLC: 0.6 min (method X012_S02).

The following examples of Table 5 are prepared in analogy of 5-Cyano-2-[3-methyl-2,5-dioxo-1-(3-trifluoromethyl-phenyl)-1,2,3,4,5,6,7,8-octahydro-quinazolin-4-yl]-benzamide (example 6), using the appropriate amine as starting material.

TABLE 5

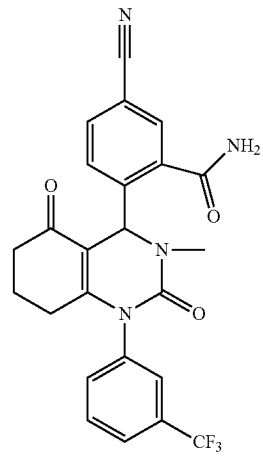 [SMILES: CN1C(=O)N(c2cccc(C(F)(F)F)c2)C2=C(C(=O)CCC2)C1c1ccc(C#N)cc1C(N)=O]

| Example | R | MS [M + H]+ | Retention time [min] | HPLC-Method |
|---|---|---|---|---|
| 6.1 | (morpholine) | 539 | 0.65 | X012_SO2 |
| 6.2 | (N-methylpiperazine) | 552 | 0.53 | X012_SO2 |
| 6.3 | (piperazine NH) | 538 | 0.52 | X012_SO2 |
| 6.4 | (N,N-dimethylamine) | 497 | 0.65 | X012_SO2 |

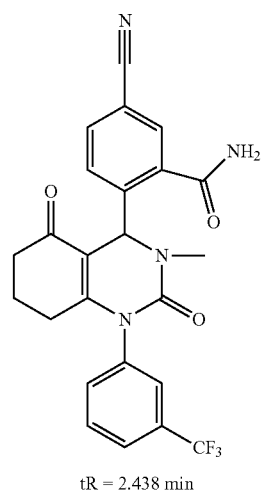

7.a tR = 1.814 min 7.b tR = 2.438 min

5-Cyano-2-[3-methyl-2,5-dioxo-1-(3-trifluoromethyl-phenyl)-1,2,3,4,5,6,7,8-octahydro-quinazolin-4-yl]-benzamide The compound is prepared as described for example 6. The enantiomers are separated by preparative supercritical fluid chromatography on a chiral phase (Daicel Chiralpak AD-H, 4.6×250 mm, 5 μm, 25% MeOH+0.2% ammonia in supercritical $CO_2$, 40° C., 150 bar back pressure). Yield example 7.a: 61.5 mg; ESI mass spectrum $[M+H]^+$=469; Retention time: 1.814 min (early eluting enantiomer) (I_IC10_ETOH_NH3.M); Yield example 7.b: 61.7 mg; ESI mass spectrum $[M+H]^+$=469; Retention time: 2.438 min (late eluting enantiomer) (I_IC10_ETOH_NH3.M),

Example 8

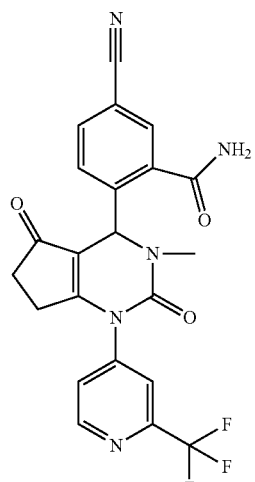

5-Cyano-2-[(R)-3-methyl-1-(2-trifluoromethyl-pyridin-4-yl)-2,5-dioxo-2,3,4,5,6,7-hexahydro-1H-cyclopentapyrimidin-4-yl]-benzamide 5-Cyano-2-[3-methyl-1-(2-trifluoromethyl-pyridin-4-yl)-2,5-dioxo-2,3,4,5,6,7-hexahydro-1H-cyclopentapyrimidin-4-yl]-benzoic acid (intermediate 25)(25 mg, 0.055 mmol) is dissolved in N,N-dimethylformamide (2.0 mL) and N,N,N',N'-tetramethyl-O-(benzotriazol-1-yl)uronium tetrafluoroborate (17.6 mg, 0.055 mmol) and triethylamine (30.5 μL, 0.22 mmol) are added and the mixture is stirred at room temperature for 5 min Ammonium chloride (14.7 mg, 0.27 mmol) and triethylamine (30.5 μL, 0.22 mmol) are added and the mixture is stirred at room temperature overnight. The reaction mixture is purified by reversed phase HPLC. Yield: 11.6 mg; ESI mass spectrum [M+H]$^+$=456.2; Retention time HPLC: 0.63 min (method 006_CA07).

The following examples of Table 6 are prepared in analogy of 5-Cyano-2-[(R)-3-methyl-1-(2-trifluoromethyl-pyridin-4-yl)-2,5-dioxo-2,3,4,5,6,7-hexahydro-1H-cyclopentapyrimidin-4-yl]-benzamide (example 8), using the appropriate amine as starting material.

TABLE 6

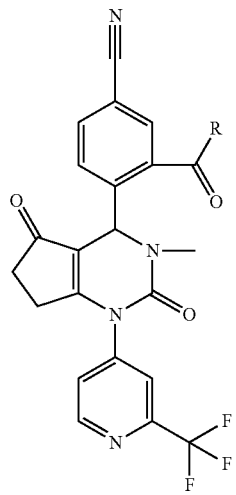

| Example | R | MS [M + H]$^+$ | Retention time [min] | HPLC-Method |
|---|---|---|---|---|
| 8.1 | H-N-CH₃ | 470 | 0.67 | 006_CA07 |

TABLE 6-continued

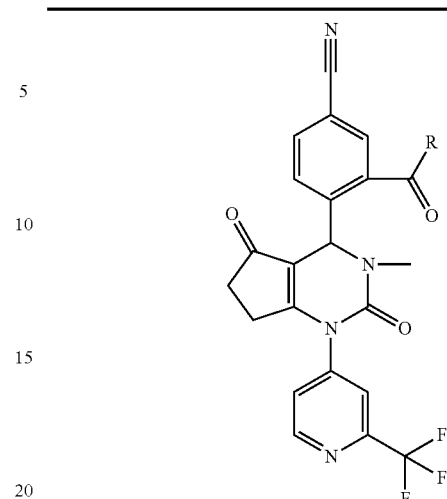

| Example | R | MS [M + H]$^+$ | Retention time [min] | HPLC-Method |
|---|---|---|---|---|
| 8.2 | -N(CH₃)₂ | 484 | 0.69 | 006_CA07 |
| 8.3 | pyrrolidinyl | 510 | 0.74 | 005_CA01 |
| 8.4 | piperidinyl | 524 | 0.79 | 005_CA01 |
| 8.5 | morpholinyl | 526 | 0.69 | 005_CA01 |

Example 9

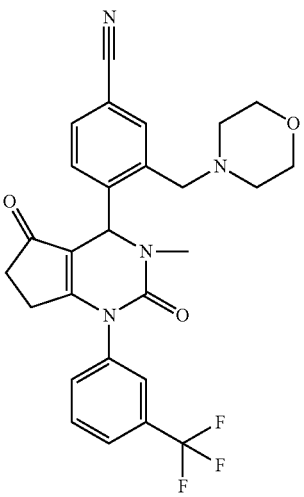 [SMILES: CN1C(=O)N(c2cccc(C(F)(F)F)c2)C2=C(C(=O)CC2)C1c1ccc(C#N)cc1CN1CCOCC1]

4-[3-Methyl-2,5-dioxo-1-(3-trifluoromethyl-phenyl)-2,3,4,5,6,7-hexahydro-1H-cyclopentapyrimidin-4-yl]-3-morpholin-4-ylmethyl-benzonitrile 3-Formyl-4-[3-methyl-2,5-dioxo-1-(3-trifluoromethyl-phenyl)-2,3,4,5,6,7-hexahydro-1H-cyclopentapyrimidin-4-yl]-benzonitrile (intermediate 27)(200 mg, 0.46 mmol) is dissolved in 1,2-dichloroethane (8 mL) and morpholine (250.1 µL, 2.87 mmol), acetic acid (166 µL, 2.87 mmol) and sodium u) triacetoxyborohydride (155.4 mg, 0.73 mmol) are added and the mixture is stirred at room temperature overnight. The organic phase is extracted with NaHCO$_3$-solution, dried and evaporated. The product is crystallized from acetonitrile. Yield: 122 mg; ESI mass spectrum [M+H]$^+$= 511.7; Retention time HPLC: 0.54 min (method X012_S02).

The following examples of Table 7 are prepared in analogy of 4-[3-Methyl-2,5-dioxo-1-(3-trifluoromethyl-phenyl)-2,3,4,5,6,7-hexahydro-1H-cyclopentapyrimidin-4-yl]-3-morpholin-4-ylmethyl-benzonitrile (example 9), using the appropriate amine as starting material.

TABLE 7

| Example | R | MS [M + H]$^+$ | Retention time [min] | HPLC-Method |
|---|---|---|---|---|
| 9.1 | ``...NH-iPr`` | 483 | 0.93 | 006_CA07 |
| 9.2 | ``...NH-tBu`` | 497 | 1.00 | 006_CA07 |
| 9.3 | ``...NH-tetrahydropyran-4-yl`` | 525 | 0.84 | Z018_S04 |
| 9.4 | ``...NH-Et`` | 455 | 1.04 | Z018_S04 |

Example 10

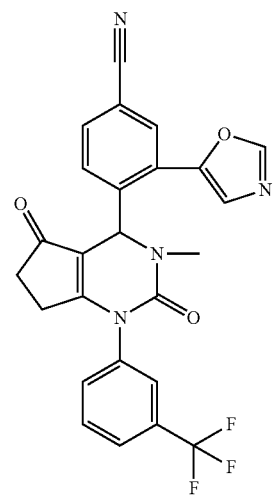 [SMILES: CN1C(=O)N(c2cccc(C(F)(F)F)c2)C2=C(C(=O)CC2)C1c1ccc(C#N)cc1-c1cnco1]

4-[3-Methyl-2,5-dioxo-1-(3-trifluoromethyl-phenyl)-2,3,4,5,6,7-hexahydro-1H-cyclopentapyrimidin-4-yl]-3-oxazol-5-yl-benzonitrile 3-Formyl-4-[3-methyl-2,5-dioxo-1-(3-trifluoromethyl-phenyl)-2,3,4,5,6,7-hexahydro-1H-cyclopentapyrimidin-4-yl]-benzonitrile (intermediate 27) (174.0 mg, 0.40 mmol), p-toluenesulfonylmethyl isocyanide (77.3 mg, 0.4 mmol) and potassium carbonate (54.7 mg, 0.4 mmol) are suspended in methanol (4 mL) and stirred at 80° C. for 90 min. The reaction mixture is diluted with ethyl acetate and extracted with water, 5% NaHCO$_3$-solution, water, dried over MgSO$_4$ and evaporated under reduced pressure. The product is purified by reversed phase HPLC. Yield: 58 mg; ESI mass spectrum [M+H]$^+$=479.7; Retention time HPLC: 0.63 min (method X012_S02).

Example 11

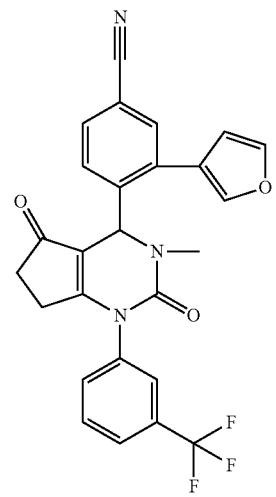 [SMILES: CN1C(=O)N(c2cccc(C(F)(F)F)c2)C2=C(C(=O)CC2)C1c1ccc(C#N)cc1-c1ccoc1]

3-Furan-3-yl-4-[3-methyl-2,5-dioxo-1-(3-trifluoromethyl-phenyl)-2,3,4,5,6,7-hexahydro-1H-cyclopentapyrimidin-4-yl]-benzonitrile 3-Bromo-4-[3-methyl-2,5-dioxo-1-(3-trifluoromethyl-phenyl)-2,3,4,5,6,7-hexahydro-1H-cyclopentapyrimidin-4-yl]-benzonitrile (intermediate 4)(200 mg, 0.41 mmol) and furan-3-yl-boronic acid (68.5 mg, 0.61 mmol) are suspended in N,N-dimethylformamide (2.0 mL) and are degassed with a stream of argon gas. 1,1'-Bis(di-tert-butylphosphino)ferrocene-palladium dichloride, complex with dichloromethane 1:1 (25.6 mg, 0.041 mmol) and cesium carbonate solution (2 mol/L, 408 µL, 0.82 mmol) are added and the mixture is stirred at 80° C. for 2 h. Ethylacetate is added and the organic phase is extracted with water three times, dried and evaporated. Purification is performed by medium pressure chromatography on silica gel using dichloromethane/methanol 98:2 as eluent or by preparative HPLC. Yield: 157 mg; ESI mass spectrum [M+H]⁺=478.6; Retention time HPLC 0.7 min (method X012_S02)

The following examples of Table 8 are prepared in analogy of 3-Furan-3-yl-4-[3-methyl-2,5-dioxo-1-(3-trifluoromethyl-phenyl)-2,3,4,5,6,7-hexahydro-1H-cyclopentapyrimidin-4-yl]-benzonitrile (example 11), using the appropriate boronic acids or boronic acid esters as starting material.

Examples 11.4, 11.5, 11.6, 11.9, 11.12-11.18 are synthesized using acetonitrile as solvent and potassium carbonate as base.

TABLE 8

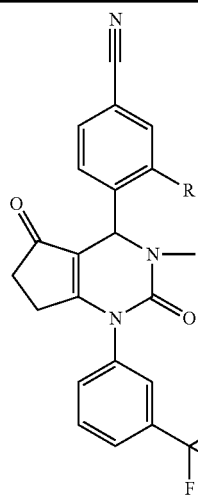

| Example | R | MS [M + H]⁺ | Retention time [min] | HPLC-Method |
|---|---|---|---|---|
| 11.1 | 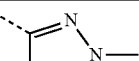 | 492 | 0.63 | X012_S02 |
| 11.2 | 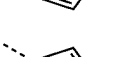 | 492 | 0.58 | X012_SO1 |
| 11.3 | 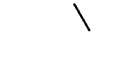 | 495 | 0.62 | X012_S02 |

TABLE 8-continued

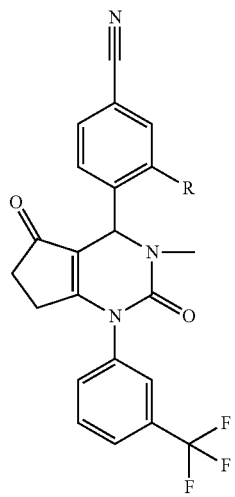

| Example | R | MS [M + H]⁺ | Retention time [min] | HPLC-Method |
|---|---|---|---|---|
| 11.4 | 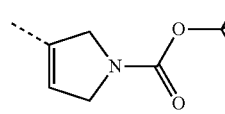 | 601 [M + Na]+ | 0.94 | 003_CA04 |
| 11.5 |  | 480 | 1.07 | Z018_SO4 |
| 11.6 | 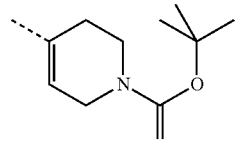 | 593 | 1.17 | Z018_S04 |
| 11.7 | 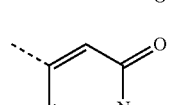 | 519 | 0.72 | 003_CA04 |
| 11.8 |  | 478 | 0.92 | 006_CA07 |
| 11.9 | 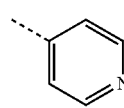 | 489 | 0.51 | X018_S01 |
| 11.10 | 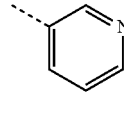 | 489 | 0.54 | X018_S01 |
| 11.11 | 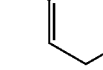 | 494 | 1.05 | Z018_S04 |

TABLE 8-continued

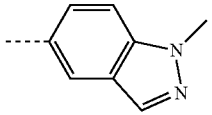

| Example | R | MS [M + H]⁺ | Retention time [min] | HPLC-Method |
|---|---|---|---|---|
| 11.12 | 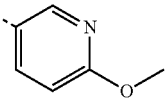 | 542 | 1.02 | Z018_S04 |
| 11.13 | 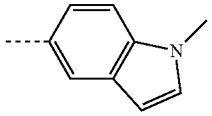 | 519 | 0.81 | 004_CA05 |
| 11.14 | 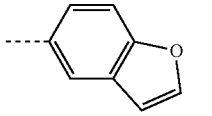 | 541 | 0.86 | 004_CA05 |
| 11.15 | 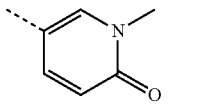 | 528 | 0.86 | 004_CA05 |
| 11.16 |  | 519 | 0.68 | 004_CA05 |

Example 12

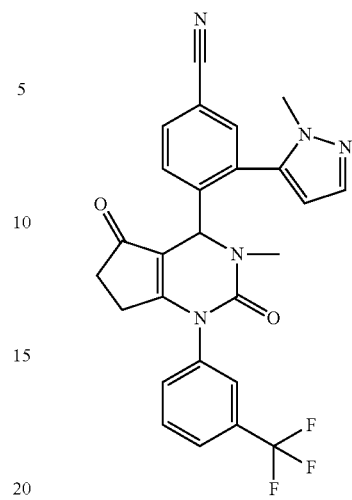

4-[3-Methyl-2,5-dioxo-1-(3-trifluoromethyl-phenyl)-2,3,4,5,6,7-hexahydro-1H-cyclopentapyrimidin-4-yl]-3-(2-methyl-2H-pyrazol-3-yl)-benzonitrile Under argon atmosphere 4-[3-methyl-2,5-dioxo-1-(3-trifluoromethyl-phenyl)-2,3,4,5,6,7-hexahydro-1H-cyclopentapyrimidin-4-yl]-3-(4,4,5,5-tetramethyl-[1,3,2]dioxaborolan-2-yl)-benzonitrile (intermediate 28a) (200 mg, 0.37 mmol) and 5-Iodo-1-methyl-1H-pyrazole (116 mg, 0.56 mmol) are suspended in N,N-dimethylformamide (2.5 ml) and [1,1'-bis(diphenylphospino)ferrocene]-dichloropalladium(II), complex with dichloromethane (1:1)(30.4 mg, 0.04 mmol) and cesium carbonate solution (2 mol/L, 372 µL, 0.74 mmol) are added. The reaction is stirred at 80° C. for 2 h. The reaction mixture is diluted with ethyl acetate and the organic phase is extracted with water three times, dried and concentrated. Purification is performed by medium pressure chromatography on silica gel using dichloromethane/methanol 99:1→97:3 as eluent. Yield: 81 mg; ESI mass spectrum [M+H]⁺=492.8; Retention time HPLC: 0.61 min (method X012_S02).

Example 13

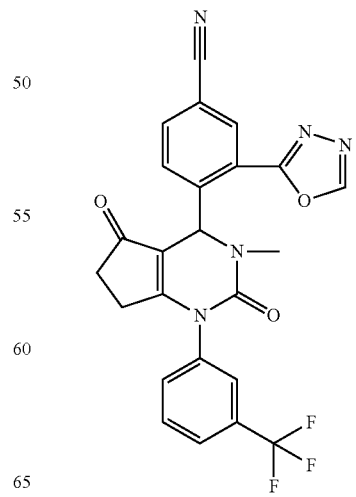

4-[3-Methyl-2,5-dioxo-1-(3-trifluoromethyl-phenyl)-2,3,4,5,6,7-hexahydro-1H-cyclopentapyrimidin-4-yl]-3-[1,3,4]oxadiazol-2-yl-benzonitrile 5-Cyano-2-[3-methyl-2,5-dioxo-1-(2-trifluoromethyl-pyridin-4-yl)-2,3,4,5,6,7-hexahydro-1H-cyclopentapyrimidin-4-yl]-benzoic acid formylhydrazide (intermediate 29) (170 mg, 0.34 mmol) is suspended in dichloromethane (2 mL) and a small amount of acetonitrile is added. (Methoxycarbonylsulfamoyl)triethylammonium hydroxide (Burgess reagent)(204 mg, 0.85 mmol) is added and the mixture is stirred at room temperature overnight. The solvent is removed under reduced pressure and purification is performed by medium pressure chromatography on silica gel using dichloromethane/methanol 99:1 as eluent. Yield: 27 mg; ESI mass spectrum [M+H]$^+$=480.7; Retention time HPLC: 0.60 min (method X012_S02).

Example 13.1

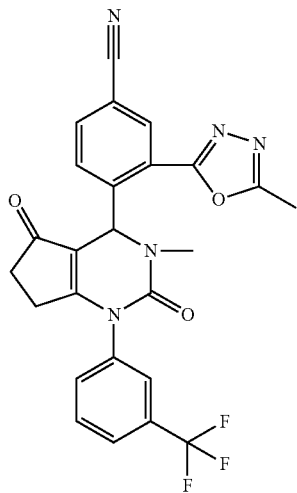 [SMILES: Cc1nnc(-c2cc(C#N)ccc2C2C3=C(CCC3=O)N(c3cccc(C(F)(F)F)c3)C(=O)N2C)o1]

4-[3-Methyl-2,5-dioxo-1-(3-trifluoromethyl-phenyl)-2,3,4,5,6,7-hexahydro-1H-cyclopentapyrimidin-4-yl]-3-(5-methyl-[1,3,4]oxadiazol-2-yl)-benzonitrile 5-Cyano-2-[3-methyl-2,5-dioxo-1-(2-trifluoromethyl-pyridin-4-yl)-2,3,4,5,6,7-hexahydro-1H-cyclopentapyrimidin-4-yl]-benzoic acid acetylhydrazide (intermediate 30) (27.4 mg, 0.05 mmol) is suspended in dichloromethane (1 mL) and (methoxycarbonylsulfamoyl)-triethylammonium hydroxide (Burgess reagent)(32.0 mg, 0.13 mmol) is added. The mixture is stirred at room temperature for three days. The solvent is removed under reduced pressure and purification is performed by reversed phase HPLC. Yield: 23.7 mg; ESI mass spectrum [M+H]$^+$=494; Retention time HPLC: 1.0 min (method Z018_S04).

Example 13.2

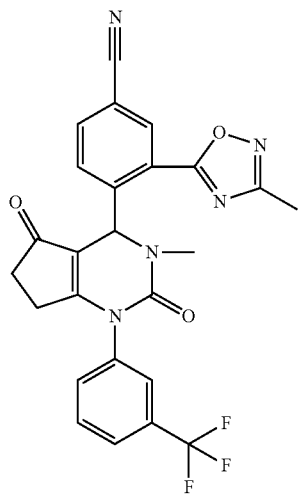 [SMILES: Cc1noc(-c2cc(C#N)ccc2C2C3=C(CCC3=O)N(c3cccc(C(F)(F)F)c3)C(=O)N2C)n1]

4-[3-Methyl-2,5-dioxo-1-(3-trifluoromethyl-phenyl)-2,3,4,5,6,7-hexahydro-1H-cyclopentapyrimidin-4-yl]-3-(3-methyl-[1,2,4]oxadiazol-5-yl)-benzonitrile

[1-Aminoethylideneamino]-5-Cyano-2-[3-methyl-2,5-dioxo-1-(3-trifluoromethyl-phenyl)-2,3,4,5,6,7-hexahydro-1H-cyclopentapyrimidin-4-yl]-benzoate (intermediate 31) (50.2 mg, 0.1 mmol) is suspended in dichloromethane (1 mL) and (methoxycarbonylsulfamoyl)-triethylammonium hydroxide (Burgess reagent)(58.5 mg, 0.25 mmol) is added. The mixture is stirred at room temperature for 4 h. The solvent is removed under reduced pressure and purification is performed by reversed phase HPLC. Yield: 8.2 mg; ESI mass spectrum [M+H]$^+$=494; Retention time HPLC: 1.03 min (method Z018_S04).

Example 14

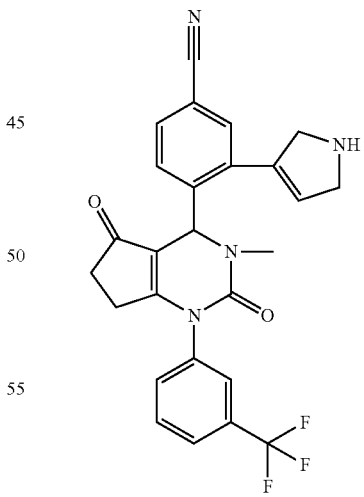

3-(2,5-Dihydro-1H-pyrrol-3-yl)-4-[3-methyl-2,5-dioxo-1-(3-trifluoromethyl-phenyl)-2,3,4,5,6,7-hexahydro-1H-cyclopentapyrimidin-4-yl]-benzonitrile 3-{5-Cyano-2-[3-methyl-2,5-dioxo-1-(3-trifluoromethyl-phenyl)-2,3,4,5,6,7-hexahydro-1H-cyclopentapyrimidin-4- yl]-phenyl}-2,5-dihydro-pyrrole-1-carboxylic acid tert-butyl ester (example 11.4)(15 mg, 25.9 μmol) is suspended in trifluoroacetic acid (1 mL) and the mixture is stirred for 2 h. The mixture is concentrated and purified by reversed phase HPLC. Yield: 9.5 mg; ESI mass spectrum [M+H]$^+$=479; Retention time HPLC: 0.84 min (method Z018_S04).

Example 14.1

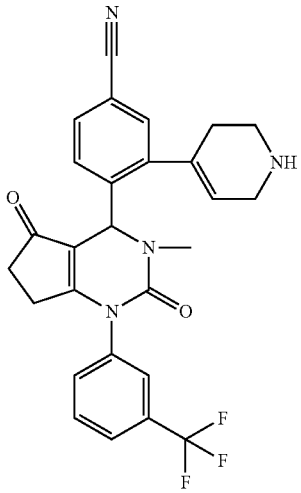 [SMILES: CN1C(=O)N(c2cccc(C(F)(F)F)c2)C2=C(C(=O)CC2)C1c1ccc(C#N)cc1C1=CCNCC1]

4-[3-Methyl-2,5-dioxo-1-(3-trifluoromethyl-phenyl)-2,3,4,5,6,7-hexahydro-1H-cyclopentapyrimidin-4-yl]-3-(1,2,3,6-tetrahydro-pyridin-4-yl)-benzonitrile 4-{5-Cyano-2-[3-methyl-2,5-dioxo-1-(3-trifluoromethyl-phenyl)-2,3,4,5,6,7-hexahydro-1H-cyclopentapyrimidin-4-yl]-phenyl}-3,6-dihydro-2H-pyridine-1-carboxylic acid tert-butyl ester (example 11.6)(35 mg, 59.1 μmol) is suspended in trifluoroacetic acid (1 mL) and the mixture is stirred for 15 min. The mixture is concentrated and purified by reversed phase HPLC. Yield: 21 mg; ESI mass spectrum [M+H]$^+$=493.1; Retention time HPLC: 0.79 min (method 003_CA04).

Example 15

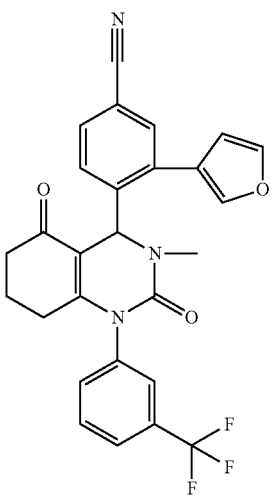 [SMILES: CN1C(=O)N(c2cccc(C(F)(F)F)c2)C2=C(C(=O)CCC2)C1c1ccc(C#N)cc1-c1ccoc1]

3-Furan-3-yl-4-[3-methyl-2,5-dioxo-1-(3-trifluoromethyl-phenyl)-1,2,3,4,5,6,7,8-octahydro-quinazolin-4-yl]-benzonitrile 3-Bromo-4-[3-methyl-2,5-dioxo-1-(3-trifluoromethyl-phenyl)-1,2,3,4,5,6,7,8-octahydro-quinazolin-4-yl]-benzonitrile (intermediate 16)(100 mg, 0.20 mmol) and furan-3-yl-boronic acid (33.3 mg, 0.30 mmol) are suspended in N,N-dimethylformamide (1.8 g) and are degassed with a stream of argon gas argon gas. 1,1'-Bis(di-tert-butylphosphino)ferrocene-palladium dichloride, complex with dichloromethane (1:1) (12.9 mg, 0.02 mmol) and cesium carbonate solution (2 mol/1, 198 μL, 0.40 mmol) are added and the mixture is stirred at 80° C. for 2 h. Ethylacetate is added and the organic phase is extracted with water three times, dried and evaporated. Purification is performed by medium pressure chromatography on silica gel using dichloromethane/methanol 99:1 as eluent. Yield: 56 mg; ESI mass spectrum [M+H]$^+$=492.6; Retention time HPLC: 0.74 min (method X012_S02)

The following examples of Table 9 are prepared in analogy of 3-Furan-3-yl-4-[3-methyl-2,5-dioxo-1-(3-trifluoromethyl-phenyl)-1,2,3,4,5,6,7,8-octahydro-quinazolin-4-yl]-benzonitrile (example 15), using the appropriate boronic acids or boronic acid esters as starting material.

Example 15.6 is synthesized using acetonitrile as solvent and potassium carbonate as base.

TABLE 9

| Example | R | MS [M + H]$^+$ | Retention time [min] | HPLC-Method |
|---|---|---|---|---|
| 15.1 | pyrazol-3-yl (N-H) | 506 | 0.68 | X012_S02 |
| 15.2 | 1-methyl-pyrazol-4-yl | 506 | 0.66 | X012_S02 |
| 15.3 | thiazol-5-yl | 509 | 0.66 | X012_S01 |

TABLE 9-continued

| Example | R | MS [M+H]+ | Retention time [min] | HPLC-Method |
|---|---|---|---|---|
| 15.4 | 1H-pyrazol-4-yl | 492 | 0.63 | X012_S02 |
| 15.5 | furan-2-yl | 492 | 0.74 | X012_S02 |
| 15.6 | N-Boc-2,5-dihydro-1H-pyrrol-3-yl | 593 | 1.20 | Z018_S04 |
| 15.7 | N-Boc-1,2,3,6-tetrahydropyridin-4-yl | 507 [M − BOC] | 1.21 | Z018_S04 |
| 15.8 | 1-methyl-2-oxo-1,2-dihydropyridin-4-yl | 533 | 1.00 | Z018_S04 |
| 15.9 | 3,6-dihydro-2H-pyran-4-yl | 508 | 0.89 | 005_CA01 |
| 15.10 | 2,5-dihydrofuran-3-yl | 494 | 1.06 | Z011_S03 |

Example 16

4-[3-Methyl-2,5-dioxo-1-(3-trifluoromethyl-phenyl)-1,2,3,4,5,6,7,8-octahydro-quinazolin-4-yl]-3-(1,2,3,6-tetrahydro-pyridin-4-yl)-benzonitrile 4-{5-Cyano-2-[3-methyl-2,5-dioxo-1-(3-trifluoromethyl-phenyl)-1,2,3,4,5,6,7,8-octahydro-quinazolin-4-yl]-phenyl}-3,6-dihydro-2H-pyridine-1-carboxylic acid tert-butyl ester (crude material from example 15.7) is suspended in trifluoroacetic acid (1 mL) and the mixture is stirred for 15 min. The mixture is concentrated and purified by reversed phase HPLC. Yield: 39 mg; ESI mass spectrum [M+H]+= 507.3; Retention time HPLC: 1.1 min (method Z018_S04).

Example 17

3-Furan-3-yl-4-[3-methyl-2,5-dioxo-1-(2-trifluoromethyl-pyridin-4-yl)-2,3,4,5,6,7-hexahydro-1H-cyclopentapyrimidin-4-yl]-benzonitrile 3-Bromo-4-[3-methyl-2,5-dioxo-1-(2-trifluoromethyl-pyridin-4-yl)-2,3,4,5,6,7-hexahydro-1H-cyclopentapyrimidin-4-yl]-benzonitrile (intermediate 23)(61.4 mg, 0.1 mmol) and furan-3-yl-boronic acid (16.8 mg, 0.15 mmol) are suspended in N,N-dimethylformamide (2 mL) and are degassed with a stream of argon gas argon. 1,1'-bis(di-tert-butylphosphino)-ferrocene-palladium dichloride, complex with dichloromethane (1:1) (1.3 mg, 0.002 mmol) and cesium carbonate solution (2 mol/L, 100 µL, 0.20 mmol) are added and the mixture is stirred at 100° C. overnight. The mixture is filtered over a short column of PR18 silica gel/basic aluminum oxide. Purification is performed by reversed phase HPLC. Yield: 19.6 mg; ESI mass spectrum [M+H]$^+$= 479; Retention time HPLC: 0.69 min (method X018_S01).

The following examples of Table 10 are prepared in analogy of 3-Furan-3-yl-4-[3-methyl-2,5-dioxo-1-(2-trifluoromethyl-pyridin-4-yl)-2,3,4,5,6,7-hexahydro-1H-cyclopentapyrimidin-4-yl]-benzonitrile (example 17), using the appropriate boronic acids or boronic acid esters as starting material. Examples 17.2 and 17.3 are synthesized using acetonitrile as solvent and potassium carbonate as base. Examples 17.1, 17.2 and 17.3 are synthesized under microwave irradiation for 40 min at 150° C.

TABLE 10

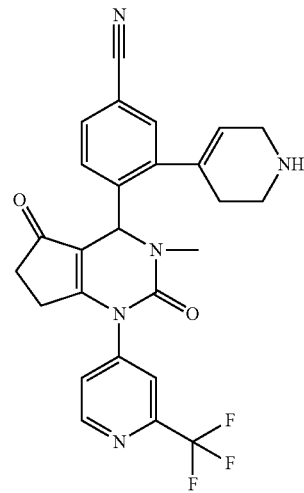 [SMILES: CN1C(=O)N(c2ccnc(C(F)(F)F)c2)C2=C(C(=O)CC2)C1c1ccc(C#N)cc1C1=CCNCC1]

| Example | R | MS [M + H]$^+$ | Retention time [min] | HPLC-Method |
|---|---|---|---|---|
| 17.1 | (pyrazolyl) | 493 | 0.62 | X018_S01 |
| 17.2 | (Boc-tetrahydropyridinyl) | 594 | 1.13 | Z018_S04 |
| 17.3 | (methylpyridinonyl) | 520 | 0.90 | Z018_S04 |

Example 18

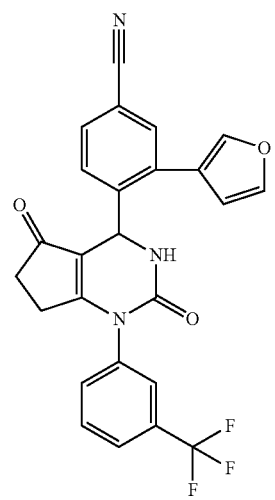 [SMILES: N#Cc1ccc(C2NC(=O)N(c3cccc(C(F)(F)F)c3)C3=C2C(=O)CC3)c(-c2ccoc2)c1]

4-[3-Methyl-2,5-dioxo-1-(2-trifluoromethyl-pyridin-4-yl)-2,3,4,5,6,7-hexahydro-1H-cyclopentapyrimidin-4-yl]-3-(1,2,3,6-tetrahydro-pyridin-4-yl)-benzonitrile 4-{5-Cyano-2-[3-methyl-2,5-dioxo-1-(2-trifluoromethyl-pyridin-4-yl)-2,3,4,5,6,7-hexahydro-1H-cyclopentapyrimidin-4-yl]-phenyl}-3,6-dihydro-2H-pyridine-1-carboxylic acid tert-butyl ester (example 17.2)(10 mg, 16.8 µmol) is suspended in trifluoroacetic acid (2 mL) and stirred for 10 min. The mixture is concentrated and purified by reversed phase HPLC. Yield: 6.9 mg; ESI mass spectrum [M+H]$^+$= 494.2; Retention time HPLC: 0.8 min (method Z018_S04).

Example 19

4-[2,5-Dioxo-1-(3-trifluoromethyl-phenyl)-2,3,4,5,6,7-hexahydro-1H-cyclopentapyrimidin-4-yl]-3-furan-3-yl-benzonitrile 3-Bromo-4-(2,5-dioxo-1-(3-(trifluoromethyl)phenyl)-2,3,4,5,6,7-hexahydro-1H-cyclopenta[d]pyrimidin-4-yl)benzonitrile (intermediate 4) (40 mg, 0.08 mmol) and furane-3 boronic acid (14.1 mg, 0.13 mmol) are suspended in acetonitrile (1.5 mL) and are degassed with a stream of argon. Potassium carbonate solution (2 mol/L, 130 μL, 0.26 mmol) and 1.1-bis(diphenylphosphino)-ferrocendichloropalladium (II), complex with dichloromethane (1:1) (3.4 mg, 0.004 mmol) are added and the reaction is shaken at 80° C. overnight. The reaction mixture is filtrated over a layer of silica gel and basic aluminum oxide 1:1 and purified by reversed phase HPLC. Yield: 24.8 mg; ESI mass spectrum [M+H]$^+$=464; Retention time HPLC: 0.99 min (method Z011_S03).

The following examples of Table 11 are prepared in analogy of 3-Furan-3-yl-4-[3-methyl-2,5-dioxo-1-(3-trifluoromethyl-phenyl)-2,3,4,5,6,7-hexahydro-1H-cyclopentapyrimidin-4-yl]-benzonitrile (example 11), using the appropriate boronic acids or boronic acid esters as starting material.

Example 19.6 is synthesized using cesium carbonate as base, dioxane as solvent and 5-(4,4,5,5-Tetramethyl-[1,3,2]dioxaborolan-2-yl)-2-triisopropylsilanyl-oxazole (intermediate 33) as reagent. The silyl group is deprotected with trifluoroacetic acid/water 1:1.

TABLE 11

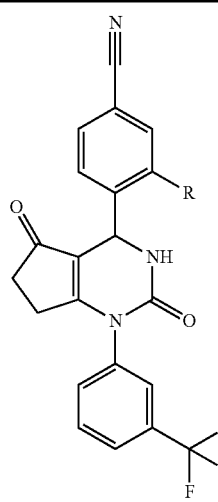

| Example | R | MS [M + H]$^+$ | Retention time [min] | HPLC-Method |
|---|---|---|---|---|
| 19.1 | pyrazole-NH | 464 | 0.92 | Z018_S04 |
| 19.2 | N-methylpyrazole | 478 | 0.91 | Z011_S03 |
| 19.3 | methoxypyridine | 504 | 0.98 | Z011_S03 |
| 19.4 | N-methylpyridinone | 505 | 0.89 | Z011_S03 |

TABLE 11-continued

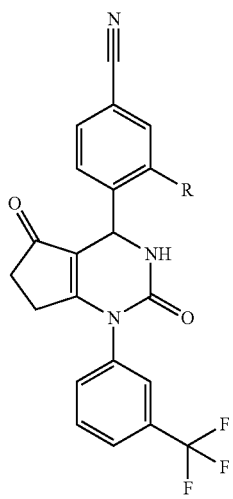

| Example | R | MS [M + H]$^+$ | Retention time [min] | HPLC-Method |
|---|---|---|---|---|
| 19.5 | N-methylpyridinone | 505 | 0.88 | Z011_S03 |
| 19.6 | oxazole | 465 | 0.95 | Z018_S04 |

Example 20

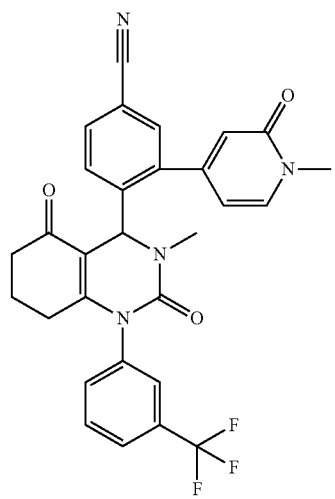

20.b

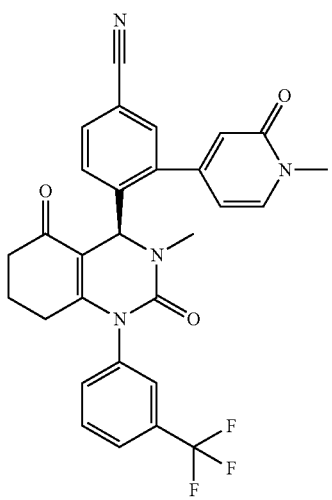

tR = 4.4 min

4-[3-Methyl-2,5-dioxo-1-(3-trifluoromethyl-phenyl)-1,2,3,4,5,6,7,8-octahydro-quinazolin-4-yl]-3-(1-methyl-2-oxo-1,2-dihydro-pyridin-4-yl)-benzonitrile The compound (300 mg) is prepared as described for example 15.8. The enantiomers 20.a and 20.b are separated by preparative supercritical fluid chromatography on a chiral phase (Daicel Chiralpak IB, 20×250 mm, 5 μm, 15% MeOH+20 mmol ammonia in supercritical $CO_2$, 40° C., 150 bar back pressure). Yield 20.a: 113 mg; ESI mass spectrum [M+H]⁺=533; Retention time 4.0 min (early eluting enantiomer) (I_IB_15_MEOH_NH3), Yield 20.b: 115 mg; ESI mass spectrum [M+H]⁺=533; Retention time: 4.4 min (late eluting enantiomer) (I_IB_15_MEOH_NH3).

Example 21

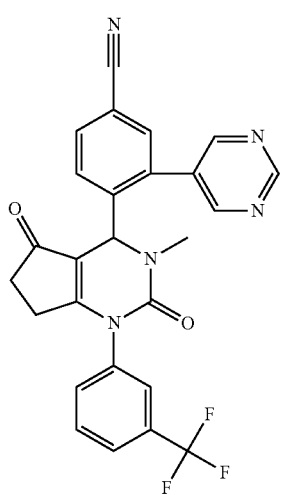

4-[3-Methyl-2,5-dioxo-1-(3-trifluoromethyl-phenyl)-2,3,4,5,6,7-hexahydro-1H-cyclopentapyrimidin-4-yl]-3-pyrimidin-5-yl-benzonitrile)

3-Bromo-4-[3-methyl-2,5-dioxo-1-(3-trifluoromethyl-phenyl)-2,3,4,5,6,7-hexahydro-1H-cyclopentapyrimidin-4-yl]-benzonitrile (intermediate 4)(45 mg, 0.092 mmol) and pyrimidine-5-yl-boronic acid (17.1 mg, 0.14 mmol) are suspended in dimetoxyethane (1.4 mL), ethanol (0.6 mL) and aqueous sodium carbonate (0.1 mL, c=2 mol/L) and are degassed with a stream of argon gas. Tetrakis(triphenylphosphine)palladium (O) (10.6 mg, 0.009 mmol) is added and the mixture is stirred at 80° C. over night. Another portion of pyrimidine-5-yl-boronic acid (17.1 mg, 0.14 mmol) and aqueous potassium carbonate (50 μL, c=2 mol/L) are added and the reaction is continued at 80° C. for 4 h. The reaction mixture is filtrated over a layer of silica gel and basic aluminum oxide 1:1 and purified by reversed phase HPLC. Crystallisation from isopropanol yielded 28 mg product. ESI mass spectrum [M+H]⁺=490; Retention time HPLC: 0.93 min (method Z011_S03).

Example 22

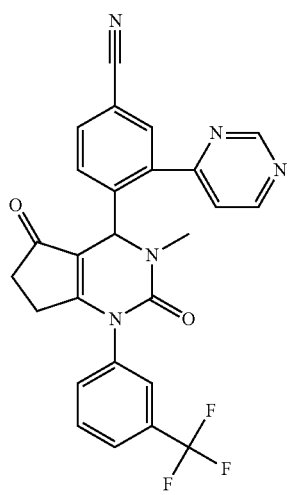 [SMILES: CN1C(=O)N(c2cccc(C(F)(F)F)c2)C2=C(C(=O)CC2)C1c1ccc(C#N)cc1-c1ccncn1]

4-[3-Methyl-2,5-dioxo-1-(3-trifluoromethyl-phenyl)-2,3,4,5,6,7-hexahydro-1H-cyclopentapyrimidin-4-yl]-3-pyrimidin-4-yl-benzonitrile The mixture of intermediates 28a, 4-[3-methyl-2,5-dioxo-1-(3-trifluoromethyl-phenyl)-2,3,4,5,6,7-hexahydro-1H-cyclopentapyrimidin-4-yl]-3-(4,4,5,5-tetramethyl-[1,3,2]dioxaborolan-2-yl)-benzonitrile, and 28b, 4-[3-Methyl-2,5-dioxo-1-(3-trifluoromethyl-phenyl)-2,3,4,5,6,7-hexahydro-1H-cyclopentapyrimidin-4-yl]-3-boronic acid-benzonitrile, (100 mg, 0.22 mmol) are suspended under inert atmosphere with 4-bromopyrimidine hydrochloride (47.2 mg, 0.24 mmol) and acetonitrile (2 ml). Potassium carbonate solution (2 mol/L, 220 μL, 0.44 mmol) and [1,1'-bis(diphenylphospino)-ferrocene]-dichloropalladium(II), complex with dichloromethane (1:1)(17.9 mg, 22 μmol) are added and the reaction is stirred at 80° C. over night. The mixture is purified by reversed phase HPLC Yield: 15 mg; ESI mass spectrum [M+H]⁺=490; Retention time HPLC: 0.98 min (method Z017_S04).

Intermediate 35

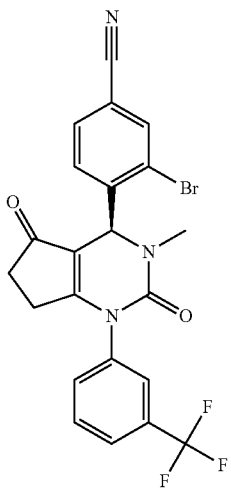 [SMILES: CN1C(=O)N(c2cccc(C(F)(F)F)c2)C2=C(C(=O)CC2)[C@H]1c1ccc(C#N)cc1Br]

3-Bromo-4-[(S)-3-methyl-2,5-dioxo-1-(3-trifluoromethyl-phenyl)-2,3,4,5,6,7-hexahydro-1H-cyclopentapyrimidin-4-yl]-benzonitrile The enantiomer separation of intermediate 4 (2.0 g) is performed by preparative supercritical fluid chromatography on a chiral phase (Daicel Chiralpak IA, 20×250 mm, 5 μm, 20% MeOH in supercritical $CO_2$, 40° C., flow 60 ml/min, 150 bar back pressure). Yield 872 mg; ESI mass spectrum $[M+H]^+$=490; Retention time: 2.03 min (early eluting enantiomer) (method: I_IA_20_MeOH_NH3). The correct stereochemistry is assigned by X-Ray crystallography.

Example 23

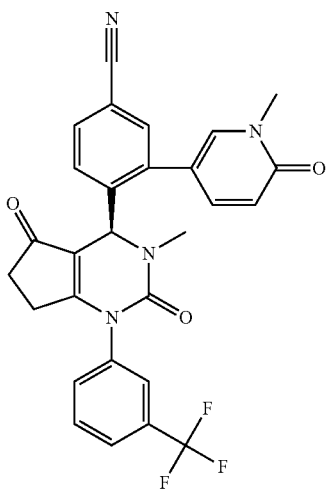 [SMILES: CN1C(=O)N(c2cccc(C(F)(F)F)c2)C2=C(C(=O)CC2)[C@H]1c1ccc(C#N)cc1-c1ccc(=O)n(C)c1]

4-[(R)-3-Methyl-2,5-dioxo-1-(3-trifluoromethyl-phenyl)-2,3,4,5,6,7-hexahydro-1H-cyclopentapyrimidin-4-yl]-3-(1-methyl-6-oxo-1,6-dihydro-pyridin-3-yl)-benzonitrile 3-Bromo-4-[(S)-3-methyl-2,5-dioxo-1-(3-trifluoromethyl-phenyl)-2,3,4,5,6,7-hexahydro-1H-cyclopentapyrimidin-4-yl]-benzonitrile (intermediate 35) (100 mg, 0.20 mmol) and 1-Methyl-5-(4,4,5,5-tetramethyl-[1,3,2]dioxaborolan-2-yl)-1H-pyridin-2-one (62.3 mg, 0.27 mmol) are suspended in acetonitrile (4 mL) and are degassed with a stream of argon gas. 1,1'-Bis(di-tert-butylphosphino)ferrocene-palladium dichloride, complex with dichloromethane 1:1 (2.0 mg, 0.002 mmol) and potassium carbonate solution (2 mol/L, 306 μL, 0.61 mmol) are added and the mixture reacted unter microeave irradiation in a sealed vial at 120° C. for 45 min. The reaction mixture is filtrated over a layer of silica gel and basic aluminum oxide 1:1 and purified by reversed phase HPLC. Yield: 57 mg; ESI mass spectrum $[M+H]^+$=519; retention time HPLC: 0.98 min (method Z018_S04)

Intermediate 36

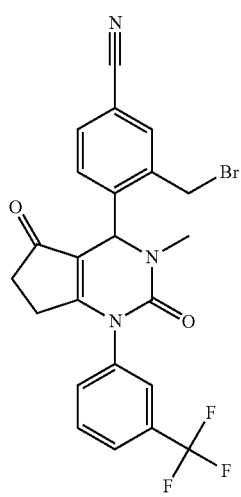 [SMILES: CN1C(=O)N(c2cccc(C(F)(F)F)c2)C2=C(C(=O)CC2)C1c1ccc(C#N)cc1CBr]

3-Bromomethyl-4-[3-methyl-2,5-dioxo-1-(3-trifluoromethyl-phenyl)-2,3,4,5,6,7-hexahydro-1H-cyclopentapyrimidin-4-yl]-benzonitrile 3-Hydroxymethyl-4-[3-methyl-2,5-dioxo-1-(3-trifluoromethyl-phenyl)-2,3,4,5,6,7-hexahydro-1H-cyclopentapyrimidin-4-yl]-benzonitrile (Intermediate 26)(4.43 g, 8.03 mmol) is suspended in dichloromethane (100 mL) and cooled in an ice bath. Phosphorus tribromide (381 μL, 4.01 mmol) is added and the mixture is stirred at room temperature over night. Additional portions of phosphorus tribromide (200 μL, 3×50 μL) are added until the reaction is completed. The reaction mixture is filtrated, the filtrate is diluted with dichloromethane and water and 1N aq. NaOH is added until the pH is basic. The phases are separated and the organic phase is washed 3 times with water, dried and concentrated. Yield: 2.84 g; ESI mass spectrum $[M+H]^+$= 504/506; retention time HPLC: 1.11 min (method Z018_S04).

Example 24

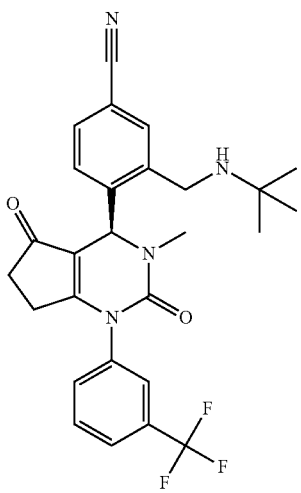 [SMILES: CN1C(=O)N(c2cccc(C(F)(F)F)c2)C2=C(C(=O)CC2)[C@H]1c1ccc(C#N)cc1CNC(C)(C)C]

3-(tert-Butylamino-methyl)-4-[(R)-3-methyl-2,5-dioxo-1-(3-trifluoromethyl-phenyl)-2,3,4,5,6,7-hexahydro-1H-cyclopentapyrimidin-4-yl]-benzonitrile 3-Bromomethyl-4-[3-methyl-2,5-dioxo-1-(3-trifluoromethyl-phenyl)-2,3,4,5,6,7-hexahydro-1H-cyclopentapyrimidin-4-yl]-benzonitrile (intermediate 36) (160 mg, 0.32 mmol) is suspended in N,N-dimethylformamide (5 mL) and potassium carbonate (87.7 mg, 0.64 mmol) and tert.butylamine (100 µL, 0.95 mmol) are added. The mixture is shaken 2 h at 50° C. The racemic product is purified by reversed phase HPLC. Yield: 498 mg; ESI mass spectrum [M+H]$^+$=497; retention time HPLC: 0.86 min (method Z018_S04). The enantiomer separation is performed by preparative supercritical fluid chromatography on a chiral phase (Daicel Chiralpak IA, 10×250 mm, 5 µm, 10% isopropanol and 20 mM NH$_3$ in supercritical CO$_2$, 40° C., flow 10 ml/min, 120 bar back pressure). Yield 43 mg; retention time: 1.31 min (early eluting enantiomer) (method: I_IA_20_IPA_NH3). The correct stereochemistry is assigned by X-Ray crystallography.

Example 25

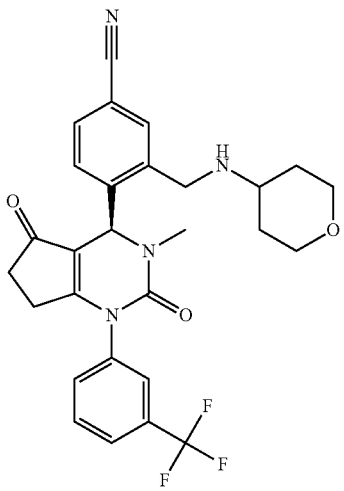 [SMILES: CN1C(=O)N(c2cccc(C(F)(F)F)c2)C2=C(C(=O)CC2)[C@H]1c1ccc(C#N)cc1CNC1CCOCC1]

4-[(R)-3-Methyl-2,5-dioxo-1-(3-trifluoromethyl-phenyl)-2,3,4,5,6,7-hexahydro-1H-cyclopentapyrimidin-4-yl]-3-[(tetrahydro-pyran-4-ylamino)-methyl]-benzonitrile 3-Bromomethyl-4-[3-methyl-2,5-dioxo-1-(3-trifluoromethyl-phenyl)-2,3,4,5,6,7-hexahydro-1H-cyclopentapyrimidin-4-yl]-benzonitrile (intermediate 36) (160 mg, 0.32 mmol) is suspended in N,N-dimethylformamide (5 mL) and potassium carbonate (70.2 mg, 0.64 mmol) and 4-aminotetrahydropyran (77 mg, 0.51 mmol) are added. The mixture is shaken 2 h at 50° C. The racemic product is purified by reversed phase HPLC. Yield: 123 mg; ESI mass spectrum [M+H]$^+$=525; retention time HPLC: 0.84 min (method Z018_S04). The enantiomer separation is performed by preparative supercritical fluid chromatography on a chiral phase (Daicel Chiralpak IA, 10×250 mm, 5 µm, 15% methanol in supercritical CO$_2$, 40° C., flow 10 ml/min, 120 bar back pressure). Yield 47 mg; retention time: 2.38 min (late eluting enantiomer) (method: I_IB_20_MeOH_NH3). The correct stereochemistry is assigned by X-Ray crystallography.

Pharmacological Data

Other features and advantages of the present invention will become apparent from the following more detailed examples which illustrate, by way of example, the principles of the invention.

Human Neutrophil Elastase Assay

Materials: Human neutrophil elastase was purchased from Calbiochem (Cat. No.: 324681) and the elastase substrate MeOSuc-Ala-Ala-Pro-Val-AMC from Bachem (Cat. No.: 1-1270). All other materials were of the highest grade commercially available.

The following buffers were used: Compound buffer: 100 mM Tris, 500 mM NaCl, adjusted to pH 7.5; Assay buffer: 100 mM Tris, 500 mM NaCl, adjusted to pH 7.5, containing 0.01% BSA.

Assay conditions: Test compounds were prediluted in DMSO and subsequently in compound buffer (5% DMSO final). 5 µL of these compound dilutions were mixed with 10 µl Neutrophil elastase (9 ng/ml in assay buffer) in a black 384 well OptiPlate (Perkin Elmer, Cat No.: 6007270) and incubated for 15 min at room temperature. Subsequently 10 µL substrate solution in assay buffer were added (250 µM final concentration) and the plates were incubated for 60 min at room temperature. After inactivation of the enzyme, fluorescence intensities were measured at 380 nm excitation and 460 nm emission wavelengths.

Each plate contains wells with a high value control (DMSO+enzyme+substrate) and wells with a low value control (DMSO+inactivated enzyme+substrate). IC$_{50}$ values were estimated using a sigmoidal concentration response curve with variable slope. Means of low values were taken as 0%, means of high values as 100%. The IC$_{50}$ values of selected compounds in the Neutrophil Elastase assay are listed in Table 12.

TABLE 12

| Example | IC50 (nM) |
| --- | --- |
| 1 | 5.3 |
| 1.1 | 6.9 |
| 1.2 | 5.5 |
| 1.3 | 5.4 |

TABLE 12-continued

| Example | IC50 (nM) |
|---|---|
| 1.4 | 3.7 |
| 1.5 | 3.1 |
| 1.6 | 6.3 |
| 1.7 | 2.2 |
| 1.8 | 5.7 |
| 1.9 | 5.5 |
| 1.10 | 3.4 |
| 1.11 | 2.5 |
| 1.12 | 5.3 |
| 1.13 | 2.9 |
| 1.14 | 6.5 |
| 1.15 | 5.0 |
| 1.16 | 6.0 |
| 1.17 | 6.6 |
| 1.18 | 6.9 |
| 1.19 | 9.5 |
| 1.20 | 5.7 |
| 1.21 | 7.1 |
| 1.22 | 10.3 |
| 1.23 | 8.4 |
| 1.24 | 3.3 |
| 1.25 | 8.0 |
| 1.26 | 4.6 |
| 1.27 | <1 |
| 1.28 | 4.3 |
| 1.29 | 4.8 |
| 1.30 | 7.4 |
| 1.31 | 3.5 |
| 1.32 | 5.6 |
| 1.33 | 10.5 |
| 1.34 | 10.9 |
| 1.34 | 2.3 |
| 1.35 | 16.2 |
| 1.36 | 2.2 |
| 1.37 | 3.4 |
| 1.38 | 5.0 |
| 1.39 | 1.9 |
| 1.40 | 1.0 |
| 1.41 | 3.8 |
| 1.42 | 1.9 |
| 1.43 | 2.0 |
| 1.44 | 3.4 |
| 1.45 | 5.3 |
| 1.46 | 3.9 |
| 1.47 | 4.2 |
| 1.48 | 4.1 |
| 1.49 | 5.0 |
| 1.50 | 2.9 |
| 1.51 | 6.6 |
| 1.52 | 4.2 |
| 1.53 | 2.2 |
| 1.54 | 6.9 |
| 1.55 | 4.8 |
| 1.56 | 5.4 |
| 1.57 | <1 |
| 1.58 | 2.4 |
| 1.59 | 1.1 |
| 1.60 | <1 |
| 1.61 | 6.0 |
| 1.62 | 2.5 |
| 1.63 | 3.9 |
| 1.64 | 6.9 |
| 1.65 | 1.7 |
| 1.66 | 7.1 |
| 1.67 | 4.1 |
| 1.68 | <1 |
| 1.69 | 9.8 |
| 1.70 | 1.9 |
| 1.71 | <1 |
| 1.72 | <1 |
| 1.73 | 1.3 |
| 1.74 | <1 |
| 1.75 | 1.4 |
| 1.76 | 4.5 |
| 1.77 | 2.3 |
| 1.78 | 2.6 |
| 1.79 | 3.0 |
| 1.80 | 6.0 |

TABLE 12-continued

| Example | IC50 (nM) |
|---|---|
| 1.81 | 1.6 |
| 1.82 | 15.0 |
| 1.83 | 2.2 |
| 1.84 | 1.3 |
| 1.85 | 4.6 |
| 2 | 2.4 |
| 2.1 | 1.8 |
| 2.2 | 1.1 |
| 2.3 | 2.9 |
| 2.4 | 3.1 |
| 3 | 7.6 |
| 3.1 | 1.3 |
| 3.2 | 8.1 |
| 3.3 | 7.5 |
| 3.4 | 7.3 |
| 3.5 | 7.0 |
| 4 | 7.5 |
| 4.1 | 15.1 |
| 4.2 | 7.1 |
| 4.3 | 3.1 |
| 4.4 | 4.7 |
| 4.5 | 2.0 |
| 4.6 | 6.9 |
| 4.7 | 3.3 |
| 4.8 | 5.9 |
| 4.9 | 6.4 |
| 4.10 | 1.4 |
| 4.11 | 6.2 |
| 4.12 | 3.8 |
| 4.13 | 5.6 |
| 4.14 | 4.9 |
| 4.15 | 7.3 |
| 4.16 | 10.8 |
| 4.17 | 36.2 |
| 5 | 3.4 |
| 6 | 1.6 |
| 6.1 | 2.9 |
| 6.2 | 5.1 |
| 6.3 | 3.5 |
| 6.4 | 1.1 |
| 7a | <1 |
| 8 | 41.0 |
| 8.1 | 25.0 |
| 8.2 | 16.8 |
| 8.3 | 32.8 |
| 8.4 | 181.0 |
| 8.5 | 71.6 |
| 9 | 1.4 |
| 9.1 | 2.1 |
| 9.2 | 3.3 |
| 9.3 | 2.9 |
| 9.4 | 2.2 |
| 10 | 1.2 |
| 11 | 3.3 |
| 11.1 | 8.7 |
| 11.2 | <1 |
| 11.3 | 1.9 |
| 11.4 | 2.5 |
| 11.5 | <1 |
| 11.6 | 1.7 |
| 11.7 | 1.2 |
| 11.8 | 3.3 |
| 11.9 | 1.0 |
| 11.10 | 3.1 |
| 11.11 | <1 |
| 11.12 | 7.9 |
| 11.13 | 3.9 |
| 11.14 | 6.0 |
| 11.15 | 16.0 |
| 11.16 | <1 |
| 12 | 7.3 |
| 13 | 2.1 |
| 13.1 | 2.2 |
| 13.2 | 2.8 |
| 14 | <1 |
| 14.2 | <1 |
| 15 | 3.2 |
| 15.1 | 2.8 |

TABLE 12-continued

| Example | IC50 (nM) |
|---|---|
| 15.2 | 2.4 |
| 15.3 | 1.9 |
| 15.4 | 1.6 |
| 15.5 | 5.7 |
| 15.6 | 10.7 |
| 15.8 | 1.2 |
| 15.9 | 1.3 |
| 15.10 | 1.5 |
| 16 | <1 |
| 17 | 11.2 |
| 17.1 | 50.2 |
| 17.2 | 4.6 |
| 17.3 | 10.6 |
| 18 | 1.7 |
| 19 | 10.1 |
| 19.1 | 5.8 |
| 19.2 | 4.8 |
| 19.3 | 21.8 |
| 19.4 | 2.4 |
| 19.5 | 5.9 |
| 19.6 | 2.4 |
| 20.b | <1 |
| 21 | 1.3 |
| 22 | 3.8 |
| 23 | <1 |
| 24 | 1.9 |
| 25 | 1.9 |

Assay for the Determination of Neutrophil Elastase Inhibitory Activity in Human Plasma Citrated blood from human healthy donors is mixed with zymosan suspension and incubated at room temperature. This leads to the stimulation of neutrophils and the release of neutrophil elastase into the plasma. The stimulated blood is centrifuged to generate the neutrophil elastase enriched plasma.

Preparation of Zymosan Working Solution:

Zymosan (100 mg) is mixed with saline (0.9%, 10 mL) and stored at 4° C. for up to one week (note: zymosan does not dissolve in the saline and is used as a suspension).

Whole Blood Stimulation:

- A single 45 ml blood sample is taken into a 50 ml tube containing citrate (3.13%, 5 mL) and the tube is gently inverted 4 times.
- Immediately after blood sampling, zymosan working solution (5 mL) is added.
- After the addition of zymosan working solution, the tubes are capped, mixed gently and incubated at 22° C. for 15 min on a shaker at 20 rpm.
- Make 10 ml aliquots after the incubation time.
- Centrifuge the 15 ml tubes at 800 g for 15 min at 4° C. in a Jouan centrifuge.
- Harvest the plasma and make 1-5 ml aliquots.
- Store the plasma at −80° C.

Various concentrations of the neutrophil elastase inhibitor are incubated with plasma. Subsequently, the enzyme activity is measured using the fluorogenic substrate MeOSuc-Ala-Ala-Pro-Val-AMC (Bachem Cat. No. 1-1270, substrate concentration: 250 µM, pH 7.5, 25 mM TRIS buffer, 250 mM NaCl) in analogous fashion as described for the human neutrophil assay. A dose response curve is generated to calculate the $EC_{50}$ of the inhibitor. The analysis of the data is performed by the calculation of the percentage of fluorescence in the presence of the test compound compared to the fluorescence of the vehicle control after subtracting the background fluorescence: An inhibitor of the neutrophil elastase enzyme will give values between 100% control (no inhibition) and 0% control (complete inhibition).

The $EC_{50}$ values of selected compounds in the human plasma assay described above are listed in Table 13.

TABLE 13

| Example | $EC_{50}$ [µM] |
|---|---|
| 2 | 0.001 |
| 2.1 | 0.002 |
| 11.2 | 0.002 |
| 13.1 | 0.002 |
| 15.8 | 0.004 |
| 20.b | 0.001 |
| 22 | 0.006 |
| 21 | 0.002 |
| 23 | 0.001 |
| 24 | 0.007 |
| 25 | 0.007 |

Assay for the Determination of Metabolic Stability with Human Liver Microsomes

The metabolic degradation of the test compound is assayed at 37° C. with pooled human liver microsomes. The final incubation volume of 100 µl per time point contains TRIS buffer pH 7.6 (0.1 M), magnesium chloride (5 mM), microsomal protein (1 mg/ml) and the test compound at a final concentration of 1 µM. Following a short preincubation period at 37° C., the reactions are initiated by addition of beta-nicotinamide adenine dinucleotide phosphate, reduced form (NADPH, 1 mM) and terminated by transferring an aliquot into acetonitrile after different time points. Additionally, the NADPH-independent degradation is monitored in incubations without NADPH, terminated at the last time point. The [%] remaining test compound after NADPH independent incubation is reflected by the parameter c (control) (metabolic stability). The quenched incubations are pelleted by centrifugation (10,000 g, 5 min) An aliquot of the supernatant is assayed by LC-MS/MS for the amount of parent compound.

The half-life ($t_{1/2}$ INVITRO) is determined by the slope of the semilogarithmic plot of the concentration-time profile. The intrinsic clearance (CL_INTRINSIC) is calculated by considering the amount of protein in the incubation:

CL_INTRINSIC [µl/min/mg protein]=(ln 2/(half-life [min]*protein content [mg/ml]))*1,000.

The half-life ($t_{1/2}$ INVITRO) values of selected compounds in the metabolic stability assay human liver microsomes described above are listed in Table 14.

TABLE 14

| Example | $t_{1/2}$ INVITRO [min] |
|---|---|
| 2 | >130 |
| 2.1 | >130 |
| 11.2 | 120 |
| 13.1 | >130 |
| 15.8 | >130 |
| 20.b | >130 |
| 22 | >130 |
| 21 | >130 |
| 23 | >130 |
| 24 | >130 |
| 25 | >130 |

Assay for the Determination of Metabolic Stability with Human Hepatocytes

The metabolic degradation of the test compound is assayed in a human hepatocyte suspension. Human hepatocytes (typically cryopreserved) are incubated in an appropriate buffer system (e.g. Dulbecco's modified eagle medium plus 3.5 µg glucagon/500 mL, 2.5 mg insulin/500 mL and 3.75 mg/500 mL hydrocortison) containing 5% species serum. Following a (typically) 30 µM preincubation in an incubator (37° C., 10% $CO_2$), 5 µl of test compound solution (80 µM; from 2 µM stock solution in DMSO diluted 1:25 with medium) are added into 395 µl hepatocyte suspension (cell density in the range 0.25-5*$10^6$ cells/mL, typically 1*$10^6$ cells/mL; final concentration of test compound 1 µM, final DMSO concentration 0.05%). The cells are incubated for six hours (incubator, orbital shaker) and samples (25 µl) are taken at 0, 0.5, 1, 2, 4 and 6 hours. Samples are transferred into acetonitrile and pelleted by centrifugation (5 min) The supernatant is transferred to a new 96-deepwell plate, evaporated under nitrogen and resuspended. The decline of parent compound is analyzed by LC-MS/MS.

The intrinsic clearance CL_INTRINSIC is calculated as follows:

$$CL\_INTRINSIC = Dose/AUC = (C_0/CD)/(AUD + c_{last}/k) * 1{,}000/60$$

($C_0$: initial concentration in the incubation [µM], CD: cell density of vital cells [$10^6$ cells/mL], AUD: area under the data [µM*h], $c_{last}$: concentration of last data point [µM], k: slope of the regression line for parent decline [$h^{-1}$])

The calculated in vitro hepatic intrinsic clearance $Q_h$ can be scaled up to the intrinsic in vivo hepatic clearance and used to predict hepatic in vivo blood clearance (CL) by the use of a liver model (well stirred model):

$$CL\_INTRINSIC\_INVIVO \,[ml/min/kg] = (CL\_IN\text{-}TRINSIC \,[\mu L/min/10^6 \,cells]*hepatocellularity \,[10^6 \,cells/g \,liver]*liver \,factor \,[g/kg \,body\text{-}weight])/1{,}000$$

$$CL \,[ml/min/kg] = CL\_INTRINSIC\_INVIVO \,[ml/min/kg]*hepatic \,blood \,flow \,[ml/min/kg]/(CL\_IN\text{-}TRINSIC\_INVIVO \,[ml/min/kg] + hepatic \,blood \,flow \,[ml/min/kg])$$

$$Q_h \,[\%] = CL \,[ml/min/kg]/hepatic \,blood \,flow \,[ml/min/kg])$$

(Hepatocellularity, human: 120*$10^6$ cells/g liver; liver factor, human: 25.7 g/kg bodyweight; blood flow, human: 21 ml/(min*kg))

The calculated in-vitro hepatic intrinsic clearance values of selected compounds in the metabolic stability assay with human hepatocytes described above are listed in Table 15.

TABLE 15

| Example | $Q_h$ [%] |
|---|---|
| 2 | 12 |
| 2.1 | 9 |
| 11.2 | 24 |
| 13.1 | 16 |
| 20.b | 5 |
| 22 | 12 |
| 21 | 23 |
| 23 | 13 |
| 24 | 10 |
| 25 | 20 |

Assay for Determination of Drug Transport Across Human Caco-2 Cells

The assay provides information on the potential of a compound to pass the cell membrane, on the extent of oral absorption as well as on whether the compound is actively transported by uptake and/or efflux transporters. For the measurement of permeability across polarized, confluent human cancer colon carcinoma cells 2 (Caco-2) cell monolayers grown on permeable filter supports are used as the in vitro absorption model.

Apparent permeability coefficients (PE) of the compounds across the Caco-2 monolayers are measured (pH 7.2, 37° C.) in apical-to-basal (AB) (absorptive) and basal-to-apical (BA) (secretory) transport direction. AB permeability (PEAB) represents drug absorption from the intestine into the blood and BA permeability (PEBA) drug secretion from the blood back into the intestine via both passive permeability as well as active transport mechanisms mediated by efflux and uptake transporters that are expressed on the Caco-2 cells. The compounds are assigned to permeability/absorption classes by comparison of the AB permeabilities with the AB permeabilities of reference compounds with known in vitro permeability and oral absorption in the human. Identical or similar permeabilities in both transport directions indicate passive permeation, vectorial permeability points to additional active transport mechanisms. Higher PEBA than PEAB suggests the involvement of an apical efflux transporter (like P-gp) and/or basolateral uptake transporter; higher PEAB than PEBA permeability suggests involvement of an apical uptake transporter (like PepT1) and/or basolateral efflux transporter (like MRP3). Active transport is concentration-dependently saturable.

Caco-2 cells (1-2*$10^5$ cells/$cm^2$ area) are seeded on filter inserts (Costar transwell polycarbonate or PET filters, 0.4 µm pore size) and cultured (DMEM) for 10 to 25 days. Compounds are dissolved in appropriate solvent (like DMSO, 1-20 µM stock solutions). Stock solutions are diluted with HTP-4 buffer (128.13 mM NaCl, 5.36 mM KCl, 1 mM $MgSO_4$, 1.8 mM $CaCl_2$, 4.17 mM $NaHCO_3$, 1.19 mM $Na_2HPO_4 \times 7H_2O$, 0.41 mM $NaH_2PO_4 \times H_2O$, 15 mM HEPES, 20 mM glucose, pH 7.2) to prepare the transport solutions (typically 10 µM compound, final DMSO<=0.5%). The transport solution (TL) is applied to the apical or basolateral donor side for measuring A-B or B-A permeability (3 filter replicates), respectively. The receiver side contains HTP-4 buffer supplemented with 2% BSA. Samples are collected at the start and end of experiment from the donor and at various time intervals for up to 2 hours also from the receiver side for concentration measurement by LC-MS/MS or scintillation counting. Sampled receiver volumes are replaced with fresh receiver solution.

The apparent permeability coefficients (PEAB and PEBA) of selected compounds in the Caco-2 drug transport assay described above are listed in Table 16.

TABLE 16

| Example | PEAB [cm/s] | PEBA [cm/s] |
|---|---|---|
| 2 | $4.8 \times 10^{-6}$ | $51 \times 10^{-6}$ |
| 2.1 | $14 \times 10^{-6}$ | $78 \times 10^{-6}$ |
| 11.2 | $61 \times 10^{-6}$ | $76 \times 10^{-6}$ |
| 13.1 | $49 \times 10^{-6}$ | $72 \times 10^{-6}$ |
| 15.8 | $3.5 \times 10^{-6}$ | $57 \times 10^{-6}$ |
| 20.b | $6.2 \times 10^{-6}$ | $95 \times 10^{-6}$ |
| 22 | $52 \times 10^{-6}$ | $77 \times 10^{-6}$ |
| 21 | $52 \times 10^{-6}$ | $67 \times 10^{-6}$ |
| 23 | $6.6 \times 10^{-6}$ | $87 \times 10^{-6}$ |
| 24 | $21 \times 10^{-6}$ | $84 \times 10^{-6}$ |
| 25 | $16 \times 10^{-6}$ | $96 \times 10^{-6}$ |

Assay for Determination of Aqueous Solubility ("High Throughput Method")

The aqueous solubility of a compound is determined by comparing the amount dissolved in aqueous buffer (containing 2.5% DMSO) to the amount dissolved in an acetonitrile/ water (1/1) solution. Starting from a 10 µM DMSO stock solution, aliquots are diluted with acetonitrile/water (1/1) and McIlvaine buffer pH 6.8, respectively. After 24 h of shaking, the solutions or suspensions are filtered and analyzed by LC-UV. The amount dissolved in buffer is compared to the amount dissolved in the acetonitrile/water (1/1) solution. Solubility is measured from 0.001 to 0.125 mg/ml at a DMSO concentration of 2.5%. If more than 90% of the compound is dissolved in buffer, the value is marked with ">".

The aqueous solubility of selected compounds in the solubility assay described above is listed in Table 17.

TABLE 17

| Example | Aqueous solubility [mg/mL] |
|---|---|
| 2 | 0.084 |
| 20.b | 0.072 |
| 22 | 0.083 |
| 21 | 0.050 |
| 23 | 0.053 |
| 24 | 0.048 |

Assay for Determination of Aqueous Solubility ("Shaked Flask Method")

Saturated solutions are prepared in well plates by adding an appropriate volume of selected aqueous media (typically in the range of 0.25-1.5 ml) into each well which contains a known quantity of solid drug substance (typically in the range 0.5-5.0 mg). The wells are shaken or stirred for a predefined time period (typically in a range of 2-24 h) and then filtered using appropriate filter membranes (typically PTFE-filters with 0.45 µm pore size). Filter absorption is avoided by discarding the first few drops of filtrate. The amount of dissolved drug substance is determined by UV spectroscopy or by HPLC with UV-detection. In addition, the pH of the aqueous saturated solution is measured using a glass-electrode pH meter. Example 2, example 20.b, example 22, example 21, example 23, example 24 and example 25 exhibit a solubility of >0.01 mg/mL at pH 6.8 in this solubility assay.

Assay for Determination of Cytochrome P450 2C9 Inhibition

The inhibition of cytochrome P450 2C9-isoenzyme catalysed hydroxylation of Diclofenac by the test compound is assayed at 37° C. with human liver microsomes. All assays are carried out on a robotic system in 96 well plates. The final incubation volume contains TRIS buffer (0.1 M), $MgCl_2$ (5 µM), human liver microsomes (0.1 mg/ml), Diclofenac (10 µM) and the test compound at five different concentrations or no compound (high control) in duplicate (e.g. highest concentration 10-50 µM with subsequent serial 1:4 dilutions). Following a short preincubation period, reactions are started with the cofactor (NADPH, 1 µM) and stopped by cooling the incubation down to 8° C. and subsequently by addition of one volume of acetonitrile. An internal standard solution—usually the stable isotope of the formed metabolite—is added after quenching of incubations. Peak area analyte (=metabolite formed) and internal standard is determined by LC-MS/MS. The resulting peak area ratio analyte to internal standard in these incubations is compared to a control activity containing no test compound. Within each of the assay runs, the $IC_{50}$ of a positive control inhibitor (sulfaphenazole) is determined Experimental $IC_{50}$ values are calculated by least square regression according to the following equation:

$$\% \text{ control activity} = (100\% \text{ control activity}/(1 \pm (I/IC_{50}) *S))-B$$

(I=inhibitor concentration, S=slope factor, B=background activity)

If the inhibition of the reaction is already >50% at the lowest concentration of the test compound, the $IC_{50}$ is assigned "<lowest concentration tested" (usually <0.4 µM). If the inhibition of the reaction is still <50% at the highest concentration of the test compound, the $IC_{50}$ is assigned ">highest concentration tested" (usually >50 µM). Example 2, example 23, and example 24 exhibit an $IC_{50}$ value >50 µM in this assay.

Assay for Determination of Cytochrome P450 2C19 Inhibition

The inhibition of cytochrome P450 2C19-isoenzyme catalysed hydroxylation of Mephenytoin by the test compound is assayed at 37° C. with human liver microsomes. All assays are carried out on a robotic system in 96 well plates. The final incubation volume contains TRIS buffer (0.1 M), $MgCl_2$ (5 µM), human liver microsomes (0.5 mg/ml), (S)-Mephenytoin (70 µM) and the test compound at five different concentrations or no compound (high control) in duplicate (e.g. highest concentration 10-50 µM with subsequent serial 1:4 dilutions). Following a short preincubation period, reactions are started with the cofactor (NADPH, 1 µM) and stopped by cooling the incubation down to 8° C. and subsequently by addition of one volume of acetonitrile. An internal standard solution—usually the stable isotope of the formed metabolite—is added after quenching of incubations. Peak area analyte (=metabolite formed) and internal standard is determined by LC-MS/MS. The resulting peak area ratio analyte to internal standard in these incubations is compared to a control activity containing no test compound. Within each of the assay runs, the $IC_{50}$ of a positive control inhibitor (tranylcypromine) is determined Experimental $IC_{50}$ values are calculated by least square regression according to the following equation:

$$\% \text{ control activity} = (100\% \text{ control activity}/(1+(I/IC_{50}) *S))-B$$

(I=inhibitor concentration, S=slope factor, B=background activity)

If the inhibition of the reaction is already >50% at the lowest concentration of the test compound, the $IC_{50}$ is assigned "<lowest concentration tested" (usually <0.4 µM). If the inhibition of the reaction is still <50% at the highest concentration of the test compound, the $IC_{50}$ is assigned ">highest concentration tested" (usually >50 µM). Example 2, example 23 and example 24 exhibit an $IC_{50}$ value >50 µM in this assay.

Assay for Determination of Cytochrome P450 2C8 Inhibition

The inhibition of cytochrome P450 2C8-isoenzyme catalysed deethylation of Amodiaquine by the test compound is assayed at 37° C. with human liver microsomes. All assays are carried out on a robotic system in 96 well plates. The final incubation volume contains TRIS buffer (0.1 M), $MgCl_2$ (5 µM), human liver microsomes (0.05 mg/ml), Amodiaquine (1 µM) and the test compound at five different concentrations or no compound (high control) in duplicate (e.g. highest concentration 10-50 µM with subsequent serial 1:4 dilutions). Following a short preincubation period, reactions are started with the cofactor (NADPH, 1 µM) and stopped by cooling the incubation down to 8° C. and subsequently by addition of one volume of acetonitrile. An internal standard solution—usually the stable isotope of the formed metabolite—is added after quenching of incubations. Peak area analyte (=metabolite formed) and internal standard is determined by LC-MS/MS. The resulting peak area ratio analyte to internal standard in these incubations is compared to a control activity containing no test compound. Within each of the assay runs, the $IC_{50}$ of a positive control inhibitor (Montelukast) is determined Experimental $IC_{50}$ values are calculated by least square regression according to the following equation:

$$\% \text{ control activity} = (100\% \text{ control activity}/(1+(I/IC_{50})*S))-B$$

(I=inhibitor concentration, S=slope factor, B=background activity)

If the inhibition of the reaction is already >50% at the lowest concentration of the test compound, the $IC_{50}$ is assigned "<lowest concentration tested" (usually <0.4 µM). If the inhibition of the reaction is still <50% at the highest concentration of the test compound, the $IC_{50}$ is assigned ">highest concentration tested" (usually >50 µM). Example 2, example 23 and example 24 exhibit an $IC_{50}$ value >50 µM in this assay.

Assay for Determination of Cytochrome P450 Induction

To assess induction of metabolizing enzyme CYP3A4, cryopreserved HepaRG® cells are seeded at a density of 1.0×105 per 96 well. Cells are allowed to equilibrate for 72 hours prior to exposure of 10 µM test article for 48 hours with renewal of test article every 24 hours. Known prototypical CYP3A4 inducers Rifampicin is used as a positive control at a concentration of 25 µM. After 48 hours of exposure, medium containing the test article is removed and cells were washed with phosphate buffered saline (PBS) prior to mRNA isolation.

Calculations:

Fold induction=(Enzyme mRNA Compound)/(Enzyme mRNA Solvent Control)

Inducer Potency=(Fold Compound)/(Fold Rifampicin)*100

Assay for Determination of hERG Inhibition

The inhibition of the hERG (human ether-a-go-go-related gene) potassium channel can be determined as described in Rast, G., & Guth, B. D., Journal of Pharmacological and ToxicologicalMethods (2014), http://dx.doi.org/10.1016/j.vascn.2014.08.001.

The hERG inhibition of selected compounds in this patch clamp assay is listed in Table 18.

TABLE 18

| Example | hERG inhibition |
|---|---|
| 2 | >30 µM |
|  | (4% @ 10 µM) |
| 23 | >30 µM |
|  | (5% @ 10 µM) |
| 24 | >30 µM |
|  | (7% @ 10 µM) |

Combinations

The compounds of general formula 1 may be used on their own or combined with other active substances of formula 1 according to the invention. The compounds of general formula 1 may optionally also be combined with other pharmacologically active substances. These include, β2-adrenoceptor-agonists (short and long-acting), anticholinergics (short and long-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK, ZAP-70, FYN, BTK or ITK, inhibitors of MAP kinases as for example p38, ERK1, ERK2, JNK1, JNK2, JNK3 or SAP, inhibitors of the NF-κB signalling pathway as for example IKK2 kinase inhibitors, iNOS inhibitors, MRP4 inhibitors, leukotriene biosynthese inhibitors as for example 5-Lipoxygenase (5-LO) inhibitors, cPLA2 inhibitors, Leukotriene A4 Hydrolase inhibitors or FLAP inhibitors, MMP9-inhibitors, MMP12-inhibitors, non-steroidale antiinflammatory agents (NSAIDs), Cathepsin C (or DPPI/Dipeptidylaminopeptidase I) inhibitors, CRTH2 antagonists, DP1-receptor modulators, Thromboxane receptor antagonists, CCR3 antagonists, CCR4 antagonists, CCR1 antagonists, CCR5 antagonists, CCR6 antagonists, CCR7 antagonists, CCR8 antagonists, CCR9 antagonists, CCR30 antagonists, CXCR3 antagonists, CXCR4 antagonists, CXCR2 antagonists, CXCR1 antagonists, CXCR5 antagonists, CXCR6 antagonists, CX3CR3 antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergicreceptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Prostasin-inhibitors, Melanocortin receptor (MC1R, MC2R, MC3R, MC4R, MC5R) modulators, CGRP antagonists, Endothelin antagonists, TNFα antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immuno-therapeutic agents, compounds against swelling of the airways, compounds against cough, VEGF inhibitors, but also combinations of two or three active substances.

Preferred are betamimetics, anticholinergics, corticosteroids, PDE4-inhibitors, LTD4-antagonists, EGFR-inhibitors, Cathepsin C inhibitors, CRTH2 inhibitors, 5-LO-inhibitors, Histamine receptor antagonists and SYK-inhibitors, especially Cathepsin C inhibitors, but also combinations of two or three active substances, that is:

Betamimetics with corticosteroids, PDE4-inhibitors, CRTH2-inhibitors or LTD4-antagonists, Anticholinergics with betamimetics, corticosteroids, PDE4-inhibitors, CRTH2-inhibitors or LTD4-antagonists, Corticosteroids with PDE4-inhibitors, CRTH2-inhibitors or LTD4-antagonists PDE4-inhibitors with CRTH2-inhibitors or LTD4-antagonists CRTH2-inhibitors with LTD4-antagonists.

Pharmaceutical Compositions

Suitable preparations for administering the compounds of formula will be apparent to those with ordinary skill in the art and include for example tablets, pills, capsules, suppositories, lozenges, troches, solutions, syrups, elixirs, sachets, injectables, inhalatives and powders etc.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

Indications

The compounds of the invention and their pharmaceutically acceptable salts have activity as pharmaceuticals, in particular as inhibitors of neutrophil elastase, and thus may be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; alpha1-antitrypsin deficiency; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus; acute lung injury; acute respiratory distress syndrome;

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

5. allograft rejection: acute and chronic following, for example, transplantation of kidney, heart, liver, lung, bone marrow, skin or cornea or following blood transfusion; or chronic graft versus host disease;

6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome andSazary syndrome;

7. oncology: treatment of common cancers including prostate, breast, lung, ovarian, pancre-atic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, para-influenza; bacterial diseases such as tuberculosis and *mycobacterium avium*, leprosy; other infectious diseases, such as fungal diseases, *chlamydia, Candida, aspergillus,* cryptococcal meningitis, *Pneumocystis carnii,* cryptosporidiosis, histoplasmosis, toxoplasmosis, trypanosome infection and leishmaniasis and 9. other diseases: traumatic brain injury, abdominal aortic aneurism.

The present invention is directed to compounds of general formula 1 which are useful in the prevention and/or treatment of a disease and/or condition wherein the activity of inhibitors of neutrophil elastase is of therapeutic benefit, including but not limited to the treatment and/or prevention of asthma and allergic diseases, gastrointestinal inflammatory diseases, glomerulonephritis, eosinophilic diseases, chronic obstructive pulmonary disease, infection by pathogenic microbes, rheumatoid arthritis, neutrophilic diseases, cystic fibrosis (CF), non-cystic fibrosis, idiopathic pulmonary fibrosis, bronchiectasis, ANCA-associated vasculitis, lung cancer, bronchiectasis, emphysema, chronic bronchitis, acute lung injury (ALI), acute respiratory distress syndrome (ARDS), pulmonary hypertension, pulmonary arterial hypertension (PAH), Alpha-1-antitrypsin deficiency (AATD.), obesity and related inflammation, e.g. chronic adipose tissue inflammation, adipose inflammation, high-fat diet induced inflammation, insulin resistence, diabetes, fatty liver and liver steatosis.

A correlation between the biological activity and the medical indications is described in the literature e.g. "Henriksen, P. A. Current Opinion in Hematology (2014), 21(1), 23-28" Accordingly, the present invention relates to a compound of general formula 1 as a medicament.

In a further aspect of the present invention the present invention relates to methods for the treatment or prevention of above mentioned diseases and conditions, which method comprises the administration of an effective amount of a compound of general formula 1 to a human being.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For Example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

The actual pharmaceutically effective amount or therapeutic dosage will of course depend on factors known by those skilled in the art such as age and weight of the patient, route of administration and severity of disease. In any case the active ingredient will be administered at dosages and in a manner which allows a pharmaceutically effective amount to be delivered based upon patient's unique condition.

LIST OF ABBREVIATIONS

| | |
|---|---|
| ACN | acetonitrile |
| aq. | aqueous |
| BOC | tert. butyloxycarbonyle- |
| d | day |
| DCM | dichloromethane |
| DEA | diethylamine |
| DIPEA | n,n-diisopropylethylamine |
| DIPE | diisopropyl ether |
| DMAP | 4-dimethylaminopyridine |
| DMF | n,n-dimethylformamide |
| DMSO | dimethyl sulfoxide |
| EA | ethyl acetate |
| FA | formic acid |
| h | hour |
| HATU | o-(7-azabenzotriazol-1-yl)-N,N,N',N'-tetramethyluronium hexafluoro-phosphate |
| LiOH | lithium hydroxide |
| MeOH | methanol |
| MeTHF | methyl tetrahydrofuran |
| NaH | sodium hydride |
| PE | petrol ether |
| RT, r.t. | room temperature |
| rt | retention time |
| TBME | tert-butyl methyl ether |
| TBTU | o-(1H-benzo-1,2,3-triazol-1-yl)-N,N,N',N'-tetramethyluronium tetrafluoroborate |
| TEA | triethylamine |
| TFA | trifluoroacetic acid |
| THF | tetrahydrofuran |
| TSA | toluene sulfonic acid |

What we claim:

1. A compound of formula 1

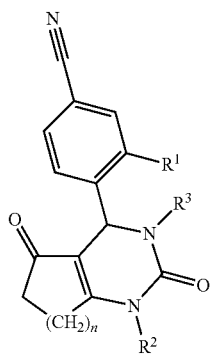

wherein
$R^1$ is selected from the group consisting of $CO-R^{1.1}$, $R^{1.11}$ and $-CH_2-R^{1.12}$ $R^{1.1}$ is selected from the group consisting of
—$NH_2$, —NH—$C_{1-4}$-alkyl, —NH—$R^{1.6}$, —NH—$CH_2$—$R^{1.6}$, —NH—$CH(CH_3)$—$R^{1.9}$, —NH—$CH_2$—$CH_2$—$R^{1.4}$, —NH—$CH_2$—$CH_2$—$CH_2$—$R^{1.7}$, —$N(CH_3)$—$CH_2$—$CH_2$—$CH_2$—$R^{1.8}$, —$N(C_{1-3}$-alkyl$)_2$, —$N(C_{3-6}$-cycloalkyl)($C_{1-3}$-alkyl), —$N(CH_3)$—$CH_2$—$CH_2$—$R^{1.5}$, —$N(CH_3)$—$CH_2$—$R^{1.10}$, —NH—$R^{1.2}$, $R^{1.3}$, —OH, —$OCH_3$ and —NH—$CH_2$—C≡CH, $R^{1.2}$ is selected from the group consisting of
$C_{3-6}$-cycloalkyl and 4- to 6 membered heterocyclic ring containing one, two, three or four heteroatoms independently selected from among N, O and S, each ring optionally substituted by one or two $C_{1-3}$ alkyl, —$NH2$, —OH or =O, $R^{1.3}$ denotes a 4- to 10-membered heterocyclic or heteroaryl ring, containing one, two, three or four heteroatoms independently selected from among N and O, each of the rings optionally substituted with one or two substituents independently selected from among morpholinyl, —$NHCOCH_3$, —$N(CH_3)COCH_3$, —$COCH_3$, —OH, —$NH_2$, —$N(CH_3)_2$ and $C_{1-3}$ alkyl, $R^{1.4}$, $R^{1.5}$ are independently selected from the group consisting of morpholinyl, —$NH_2$, —OH, F, —$N(CH_3)_2$, —O—$CH_3$ and —$SO_2$—$CH_3$, $R^{1.6}$, $R^{1.9}$, $R^{1.10}$ are independently selected from the group consisting of —CO-morpholinyl, —CN, —$CF_3$, —$CHF_2$, —$C(CH_3)_2OH$, —$C(CH_3)_2NH_2$ and —$C(CH_3)_2CN$ or are independently selected from the group consisting of phenyl and a 4- to 10-membered heterocyclic or heteroaryl ring, containing one to four heteroatoms independently selected from among N and O, each of the rings optionally substituted with $C_{1-3}$ alkyl or CN, $R^{1.7}$ is —OH or —O—$CH_3$, $R^{1.8}$ is —O—$CH_3$, $R^{1.11}$ denotes a 5- to 10-membered heterocyclic or 5- to 10-membered heteroaryl ring, containing one to four heteroatoms independently selected from among N, O and S, each of the rings optionally substituted with a group independently selected from among $C_{1-3}$ alkyl, $C_{1-3}$-cycloalkyl, OH, =O, —COO—$C_{1-4}$-alkyl, —O—$C_{1-3}$-alkyl, —O—$C_{1-3}$-cycloalkyl, —CN, halogen, —CO—$C_{1-3}$-alkyl, —CO—$C_{1-3}$-cycloalkyl and —$N(CH_3)_2$, $R^{1.12}$ is selected from the group consisting of, —NH—$R^{1.13}$, —$N(CH_3)$—$R^{1.13}$, and
a 5- to 6-membered N-containing heterocyclic ring, bound via N-atom to the —$CH_2$—, optionally containing additional to the N-atom one to 3 heteroatoms independently selected from among N, O and S, each of the rings optionally substituted with a group independently selected from among $C_{1-3}$ alkyl, $C_{1-3}$-cycloalkyl, OH, =O, —COO—$C_{1-4}$-alkyl, —O—$C_{1-3}$ alkyl, —O—$C_{1-3}$-cycloalkyl, —CN, halogen, —CO—$C_{1-3}$-alkyl and —CO—$C_{1-3}$-cycloalkyl, —$N(CH_3)_2$, $R^{1.13}$ denotes a group selected from among $C_{3-6}$-cycloalkyl, $C_{1-4}$-alkyl, each optionally substituted by a group selected from among halogen and OH, and a 6-membered heterocyclic ring, containing one to four heteroatoms independently selected from among N, O and S, optionally substituted by a group selected from among halogen, —OCH$_3$ and OH, n is 1 or 2, R$^2$ is phenyl or pyridinyl, each substituted with CF$_3$, —CHF$_2$, C$_{1-4}$ alkyl and halogen R$^3$ is selected from the group consisting of R$^{3.1}$, R$^{3.1}$—CO—, R$^{3.1}$—O—CO—, R$^{3.1}$SO$_2$—, R$^{3.1}$R$^{3.2}$N—CO— and R$^{3.1}$R$^{3.2}$N—CO—CH$_2$—, R$^{3.1}$ is selected from the group consisting of H, —C$_{1-4}$ alkyl, —C$_{3-6}$ cycloalkyl, -4-haloalkyl and —C$_{3-6}$-halocycloalkyl, each optionally substituted with one substituent independently selected from the group consisting of OH, CN, NH$_2$, (C$_{1-4}$-alkyl)NH—, (C$_{1-4}$-alkyl)(C$_{1-4}$-alkyl)N—, azetidinyl, pyrrolidinyl, piperidinyl, piperazinyl, N—C$_{1-4}$-alkyl-piperazinyl, C$_{1-4}$-alkoxy, oxetanyl, tetrahydrofuranyl and tetrahydropyranyl;

R$^{3.2}$ is selected from the group consisting of H and C$_{1-4}$-alkyl;

or, in case R$^3$ is selected from the group consisting of R$^{3.1}$R$^{3.2}$N—CO— and R$^{3.1}$R$^{3.2}$N—CO—CH$_2$—, R$^{3.2}$ and R$^{3.1}$ may form, together with the nitrogen atom to which they are bound, a ring independently selected from the group consisting of azetidine, pyrrolidine, piperidine, piperazine and N—C$_{1-4}$-alkyl-piperazine or a pharmaceutically acceptable salt thereof.

2. A compound of formula 1 according to claim 1, wherein R$^1$ is selected from the group consisting of —CO—R$^{1.1}$, R$^{1.11}$ and —CH$_2$—R$^{1.12}$, R$^{1.1}$ is selected from the group consisting of
—NH$_2$, —NH—C$_{1-4}$-alkyl, —NH—CH$_2$—R$^{1.6}$, —NH—CH(CH$_3$)—R$^{1.9}$, —NH—CH$_2$—CH$_2$—R$^{1.4}$, —NH—CH$_2$—CH$_2$—CH$_2$—R$^{1.7}$, —NH—CH$_2$—CH$_2$—CH$_2$—R$^{1.8}$, —N(C$_{1-3}$-alkyl)$_2$, —N(CH$_3$)—CH$_2$—CH$_2$—R$^{1.5}$, —N(CH$_3$)—CH$_2$—R$^{1.10}$, —NH—R$^{1.2}$, R$^{1.3}$, —OH, —OCH$_3$ and —NH—CH$_2$—C≡CH, R$^{1.2}$ is selected from the group consisting of
C$_{3-6}$-cycloalkyl and 4- to 6 membered heterocyclic ring containing one, two, three or four heteroatoms independently selected from among N, O and S, each ring optionally substituted by C$_{1-3}$ alkyl, —OH or =O, R$^{1.3}$ denotes a 4- to 6-membered heterocyclic or heteroaryl ring, containing one, two or three heteroatoms independently selected from among N and O, each of the rings optionally substituted with one or two substituents independently selected from among morpholinyl, —NHCOCH$_3$, —N(CH$_3$)COCH$_3$, —COCH$_3$, —OH, —NH$_2$, —N(CH$_3$)$_2$ and C$_{1-3}$ alkyl, R$^{1.4}$ is selected from the group consisting of
morpholinyl, —NH$_2$, —OH, F, —NH—CH$_3$, —N(CH$_3$)$_2$, —O—CH$_3$ and —SO$_2$—CH$_3$, R$^{1.5}$ is selected from the group consisting of
morpholinyl, —NH$_2$, —OH and —NH—CH$_3$, R$^{1.6}$, R$^{1.9}$, R$^{1.10}$ are independently selected from the group consisting of —CO-morpholinyl, —CN, —CF$_3$, CHF$_2$, —C(CH$_3$)$_2$OH and —C(CH$_3$)$_2$NH$_2$ or are independently selected from the group consisting of phenyl and a 4- to 6-membered heterocyclic or heteroaryl ring, containing one, to four heteroatoms independently selected from among N and O, each of the rings optionally substituted with C$_{1-3}$ alkyl or CN, R$^{1.7}$ is —OH or —O—CH$_3$, R$^{1.8}$ is —O—CH$_3$, R$^{1.11}$ denotes a 5- to 6-membered heterocyclic or 5- to 6-membered heteroaryl ring, containing one to four heteroatoms independently selected from among N, O and S, each of the rings optionally substituted with a group independently selected from among C$_{1-3}$ alkyl, =O and —COO—C$_{1-4}$-alkyl, R$^{1.12}$ is selected from the group consisting of
—NH—C$_{1-4}$-alkyl, —NH—R$^{1.13}$ and a 6-membered N-containing heterocyclic ring, bound via N-atom to the —CH$_2$—, optionally containing additional to the N-atom 1 to 3 heteroatoms independently selected from among N, O and S, R$^{1.13}$ denotes a 6-membered heterocyclic ring, containing one to four heteroatoms independently selected from among N, O and S, n is 1 or 2

R$^2$ is phenyl or pyridinyl, each substituted with CF$_3$ or CHF$_2$,

R$^3$ is H or methyl or a pharmaceutically acceptable salt thereof.

3. A compound of formula 1 according to claim 1, wherein R$^1$ is selected from the group consisting of
—CO—R$^{1.1}$, R$^{1.11}$ and —CH$_2$—R$^{1.12}$, R$^{1.1}$ is selected from the group consisting of
—NH$_2$, —NH—C$_{1-4}$-alkyl, —NH—R$^{1.6}$—NH—CH$_2$—R$^{1.6}$, —NH—CH(CH$_3$)—R$^{1.9}$, —NH—CH$_2$—CH$_2$—R$^{1.4}$, —NH—CH$_2$—CH$_2$—CH$_2$—R$^{1.7}$, —NH—CH$_2$—CH$_2$—CH$_2$—R$^{1.8}$, —N(CH$_3$)—CH$_2$—CH$_2$—CH$_2$—R$^{1.8}$, —N(CH$_3$)$_2$—N(CH$_3$)—CH$_2$—CH$_2$—R$^{1.5}$, —N(CH$_3$)—CH$_2$—R$^{1.10}$, —NH—R$^{1.2}$, R$^{1.3}$, —OH, —OCH$_3$ and —NH—CH$_2$—C≡CH, R$^{1.2}$ is selected from the group consisting of Formulas a.1 to a.14

a.1

a.2

a.3

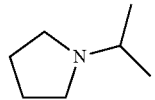

a.

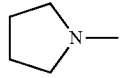

a.5

a.6

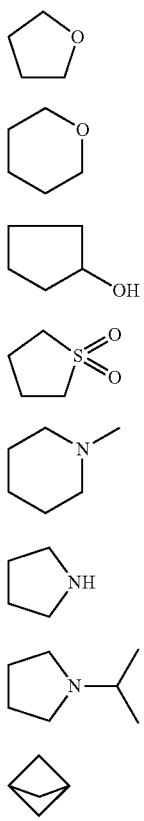
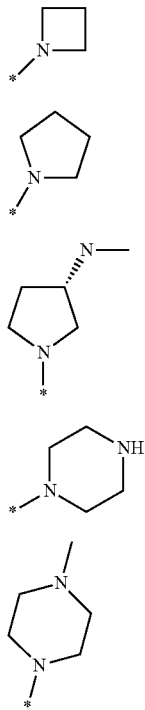
$R^{1.3}$ is selected from the group consisting of formulas b.1 to b.37
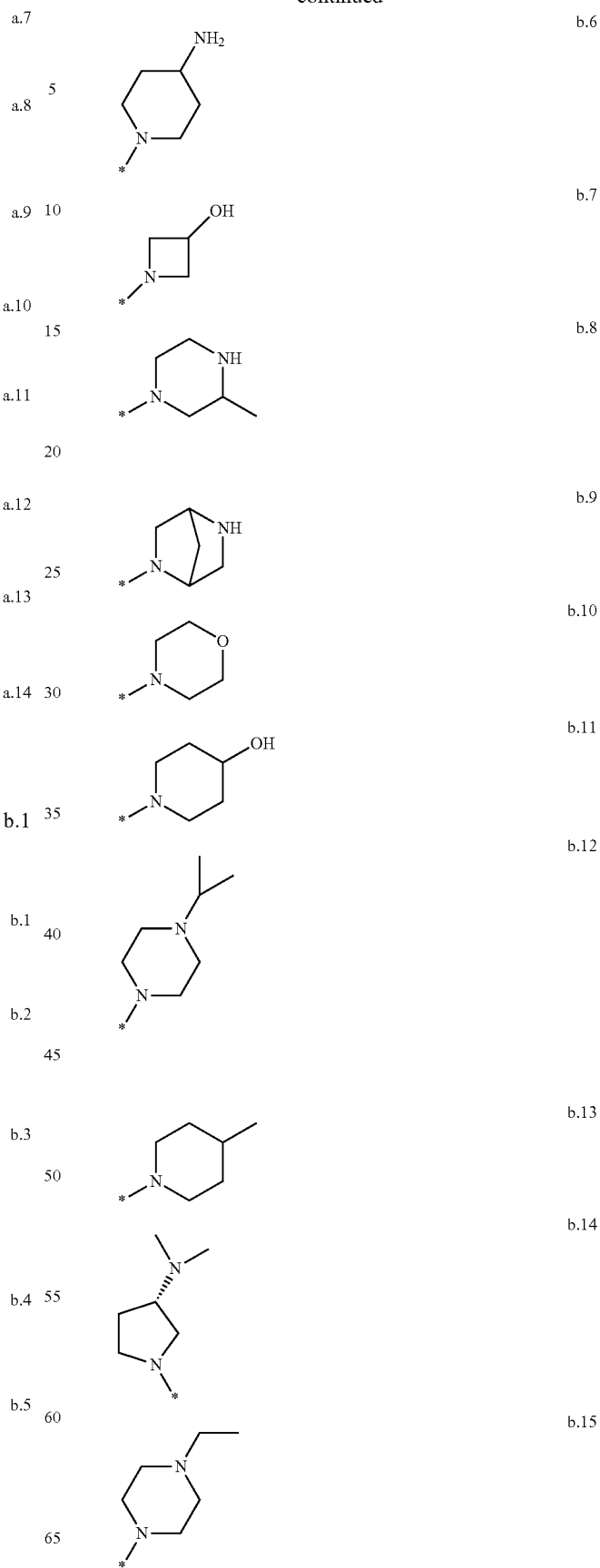

-continued
b.16 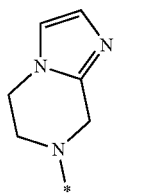
b.17 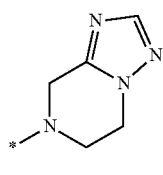
b.18 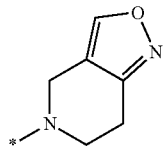
b.19 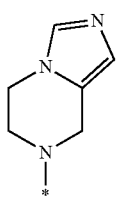
b.20 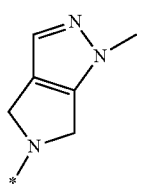
b.21 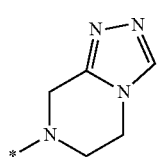
b.22 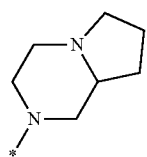
b.23 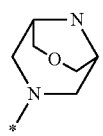
b.24 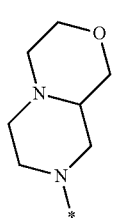
-continued
b.25 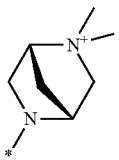
b.27 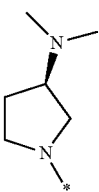
b.28 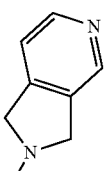
b.29 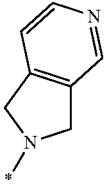
b.30 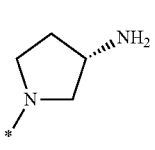
b.31 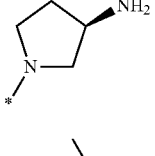
b.32 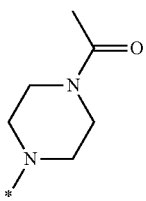
b.33 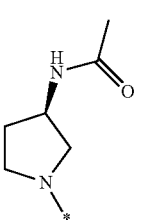

-continued b.34
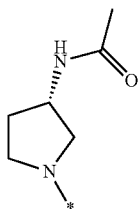

b.35
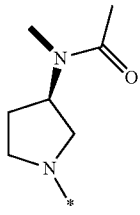

b.36
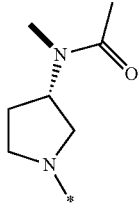

b.37
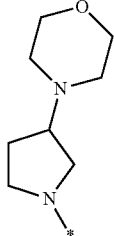

$R^{1.4}$ is selected from the group consisting of morpholinyl, —NH$_2$, —OH, F, —NH—CH$_3$, —N(CH$_3$)$_2$, —O—CH$_3$ and —SO$_2$—CH$_3$, $R^{1.5}$ is selected from the group consisting of morpholinyl, NH$_2$, —OH and —NH—CH$_3$ and —N(CH$_3$)$_2$, $R^{1.6}$ is selected from the group consisting of —CO-morpholinyl, —CN, —CF$_3$, CHF$_2$, —C(CH$_3$)$_2$OH, —C(CH$_3$)$_2$CN and —C(CH$_3$)$_2$NH$_2$
or is selected from the group consisting of formulas c.1 to c.12 c.1

c.2
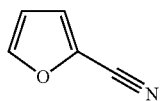

c.3

-continued c.4
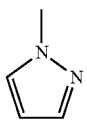

c.5
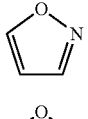

c.6
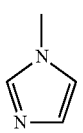

c.7
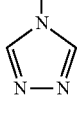

c.8
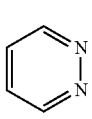

c.9
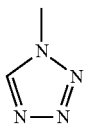

c.10
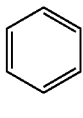

c.11
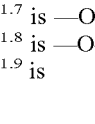

c.12

$R^{1.7}$ is —OH or —O—CH$_3$,
$R^{1.8}$ is —O—CH$_3$,
$R^{1.9}$ is

, $R^{1.10}$ is selected from the group consisting of formulas c.3, c4, c.5, c.7, c8, and c.9 as set forth above, $R^{1.11}$ denotes a 5- to 10-membered heterocyclic or 5- to 10-membered heteroaryl ring, containing one to four heteroatoms independently selected from among N, O and S, each of the rings optionally substituted with a group independently selected from among C$_{1-3}$ alkyl, =O, —COO—C$_{1-4}$-alkyl and —O—C$_{1-3}$ alkyl, n is 1 or 2
$R^2$ is phenyl or pyridinyl, each substituted with CF$_3$,
$R^3$ is H or methyl
or a pharmaceutically acceptable salt thereof.

4. A compound of formula 1 according to claim 1, wherein
$R^{1.1}$ is selected from the group consisting of
—NH₂, —NH—CH₃, —N(CH₃)₂, and $R^{1.3}$
$R^{1.3}$ is

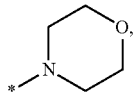 [SMILES: *N1CCOCC1]

n is 1
$R^2$ is phenyl, substituted with $CF_3$
or a pharmaceutically acceptable salt thereof.

5. A compound of formula 1 according to claim 1, wherein
$R^2$ is a residue of formula d.1 or d.2 d.1

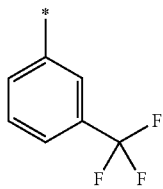

d.2

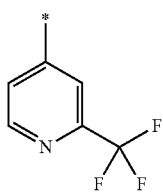

or a pharmaceutically acceptable salt thereof.

6. A compound of formula 1 according to any one of claims 1 to 5, wherein
$R^1$ is —CO—$R^{1.1}$,
or a pharmaceutically acceptable salt thereof.

7. A compound of formula 1 according to claim 1, selected from the group consisting of formulas 1.a to 1.q 1.a

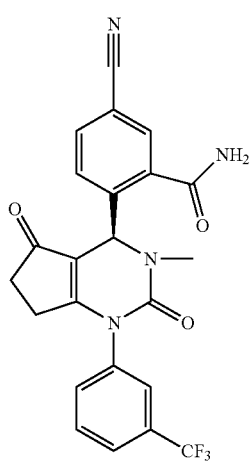

1.b

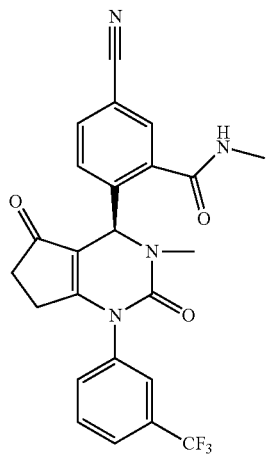

1.c

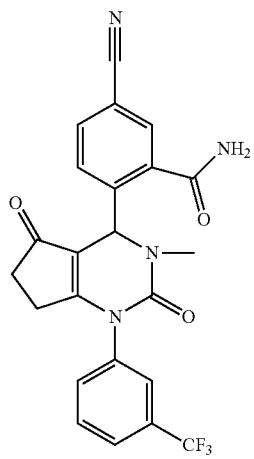

1.d

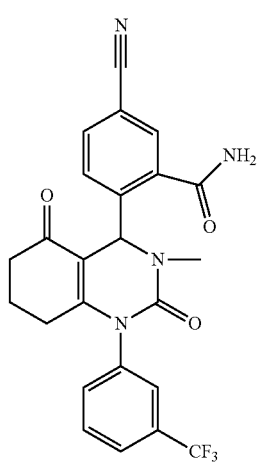

153
-continued
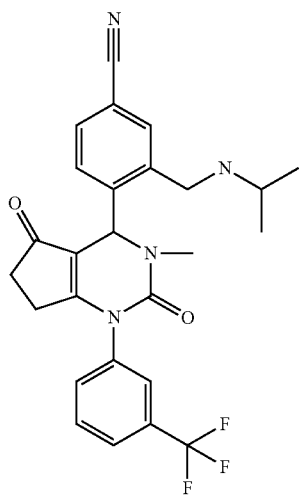
1.e
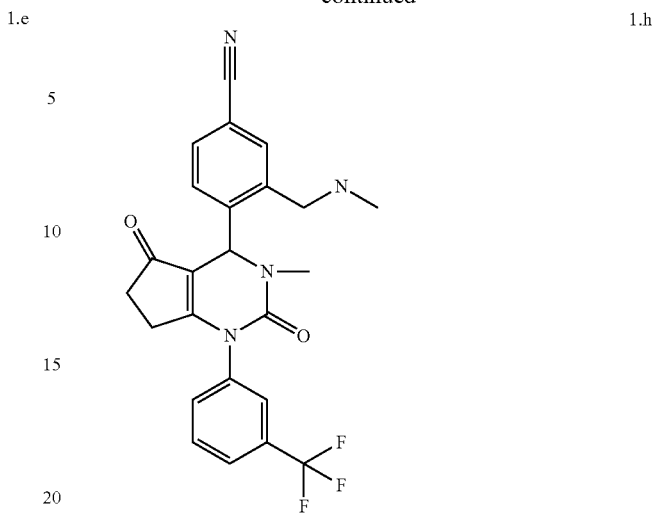
1.f
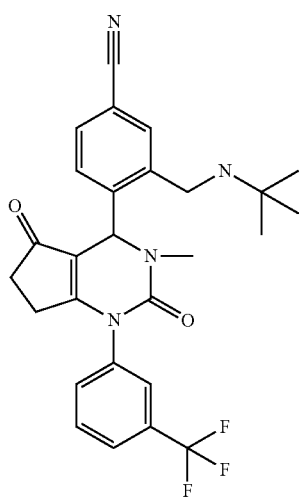
154
-continued
1.h
1.i
1.g
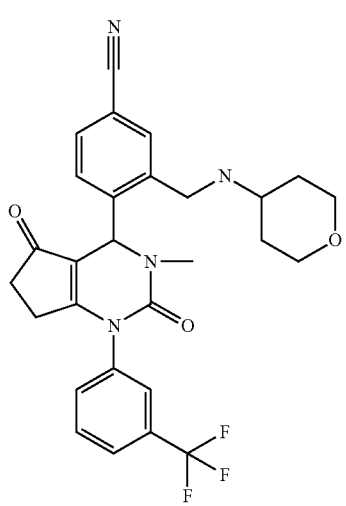
1.j
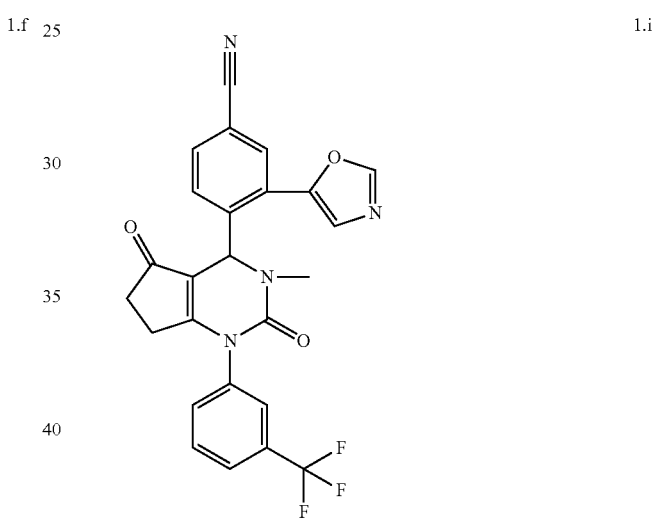
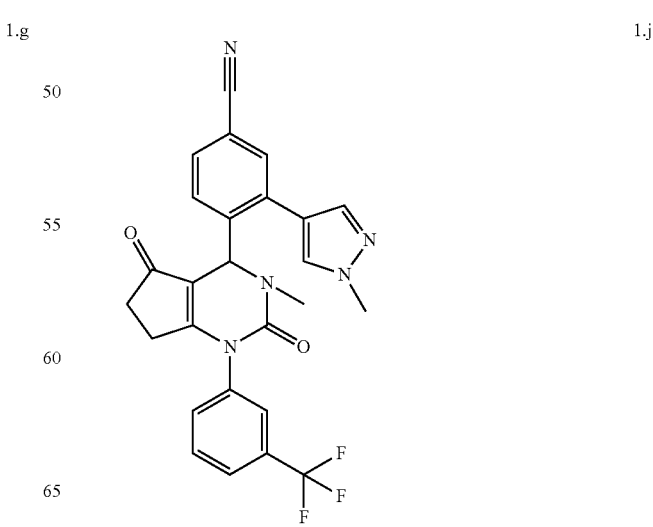

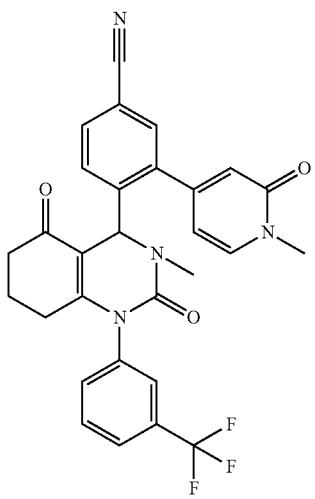
1.k
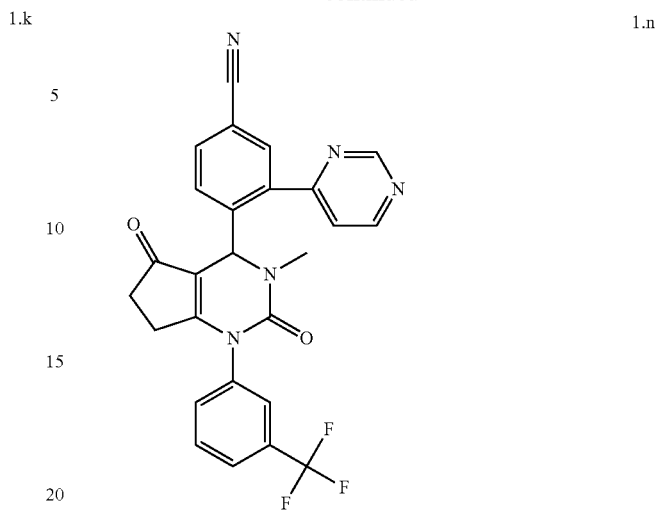
1.n
1.l
1.o
1.m
1.p

-continued

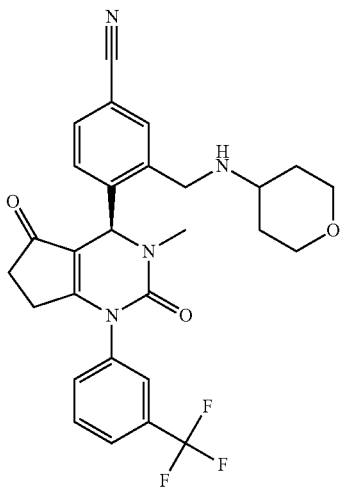

or a pharmaceutically acceptable salt thereof.

8. A compound of formula 1 according to claim 1, wherein $R^1$ is $R^{1.11}$, or a pharmaceutically acceptable salt thereof.

9. A compound of formula 1 according to claim 8, wherein $R^{1.11}$ is selected from the group consisting of f.1 to f.17, optionally substituted with one or two groups independently selected from among —$CH_3$, =O, —O—$C_{1-3}$-alkyl and —COO—$C_{1-4}$-alkyl f.1 

f.2 

f.3 

f.4 

f.5 

f.6 

f.7 

f.8 

-continued f.9 

f.10 

f.11 

f.12 

f.13 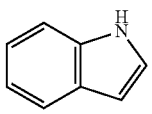

f.14 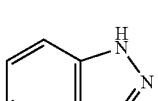

f.15 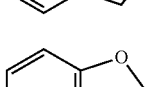

f.16 

f.17 

or a pharmaceutically acceptable salt thereof.

10. A compound of formula 1 according to claim 1, wherein $R^1$ is —$CH_2$—$R^{1.12}$ or a pharmaceutically acceptable salt thereof.

11. A compound of formula 1A according to claim 1,

1A

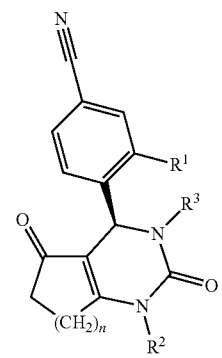

or a pharmaceutically acceptable salt thereof.

12. A pharmaceutical composition comprising a compound according to claim 1 and a pharmaceutically acceptable carrier.

13. A method of treating COPD which comprises administering to a host suffering from COPD an effective amount of a compound according to claim 1.

* * * * *